(12) United States Patent
Suto et al.

(10) Patent No.: US 9,353,149 B2
(45) Date of Patent: May 31, 2016

(54) COMPOUNDS, COMPOSITIONS AND METHODS FOR THE TREATMENT OF DISEASES THROUGH INHIBITING TGF-β ACTIVITY

(71) Applicants: Southern Research Institute, Birmingham, AL (US); THE UAB RESEARCH FOUNDATION, Birmingham, AL (US)

(72) Inventors: Mark J. Suto, Birmingham, AL (US); Joanne E. Murphy-Ullrich, Birmingham, AL (US)

(73) Assignee: Southern Research Institute, Birmingham, AL (US)

( * ) Notice: Subject to any disclaimer, the term of this patent is extended or adjusted under 35 U.S.C. 154(b) by 0 days.

(21) Appl. No.: 14/274,007

(22) Filed: May 9, 2014

(65) Prior Publication Data

US 2014/0336115 A1    Nov. 13, 2014

Related U.S. Application Data

(60) Provisional application No. 61/822,008, filed on May 10, 2013.

(51) Int. Cl.

| | |
|---|---|
| *C07K 5/08* | (2006.01) |
| *C07K 5/083* | (2006.01) |
| *C07K 5/00* | (2006.01) |
| *A61K 38/04* | (2006.01) |
| *A61K 38/06* | (2006.01) |
| *C07K 5/04* | (2006.01) |
| *A61K 38/00* | (2006.01) |

(52) U.S. Cl.
CPC .................. *C07K 5/081* (2013.01); *A61K 38/04* (2013.01); *A61K 38/06* (2013.01); *C07K 5/00* (2013.01); *C07K 5/04* (2013.01); *C07K 5/08* (2013.01); *C07K 5/0804* (2013.01); *A61K 38/00* (2013.01)

(58) Field of Classification Search
None
See application file for complete search history.

(56) References Cited

PUBLICATIONS

Medicherla et al., Anticancer Res. (2007) 27(6B), 4149-57.*
Thompson et al., Proceedings of the National Academy of Sciences (1970) 67(4), 1734-1740.*
Miura et al., The Journal of Biological Chemistry (1992) 267(20), 14405-14411.*
Thermo Electron technical bulletin, N-Terminal Acetylation and C-Terminal Amidation of Peptides (2004) available at http://www.greiner-bio-one.co.jp/products/peptides/acetylation_amidation.pdf.*
Schneider, "Tripeptides of Histidine", Hoppe-Seyler's Zeitschrift fuer Physiologische Chemie (1960) 321, 38-48.*

Adams, J. C. and J. Lawler (2004). "The thrombospondins." *Int J Biochem Cell Biol* 36(6): 961-968.
Adams, J. C. and J. Lawler (2011). "The thrombospondins." *Cold Spring Harbor perspectives in biology* 3(10): a009712.
Agah, A., T. R. Kyriakides, J. Lawler and P. Bornstein (2002). "The lack of thrombospondin-1 (TSP1) dictates the course of wound healing in double-TSP1/TSP2-null mice." *Am J Pathol* 161(3): 831-839.
Anderson, K. C. and R. D. Carrasco (2011). "Pathogenesis of myeloma." *Annual review of pathology* 6: 249-274.
Belmadani, S., J. Bernal, C. C. Wei, M. A. Pallero, L. Dell'italia, J. E. Murphy-Ullrich and K. H. Berecek (2007). "A thrombospondin-1 antagonist of transforming growth factor-beta activation blocks cardiomyopathy in rats with diabetes and elevated angiotensin II." *Am J Pathol* 171(3): 777-789.
Breitkopf, K., I. Sawitza, J. H. Westhoff, L. Wickert, S. Dooley and A. M. Gressner (2005). "Thrombospondin 1 acts as a strong promoter of transforming growth factor beta effects via two distinct mechanisms in hepatic stellate cells." *Gut* 54(5): 673-681.
Carron, J. A., C. A. Walsh, W. D. Fraser and J. A. Gallagher (1995). "Thrombospondin promotes resorption by osteoclasts in vitro." *Biochem Biophys Res Commun* 213(3): 1017-1025.
Cauchard, J. H., A. Berton, G. Godeau, W. Hornebeck and G. Bellon (2004). "Activation of latent transforming growth factor beta 1 and inhibition of matrix metalloprotease activity by a thrombospondin-like tripeptide linked to elaidic acid." *Biochemical pharmacology* 67(11): 2013-2022.
Chen, Y., A. Leask, D. J. Abraham, L. Kennedy, X. Shi-Wen, C. P. Denton, C. M. Black, L. S. Verjee and M. Eastwood (2011). "Thrombospondin 1 is a key mediator of transforming growth factor beta-mediated cell contractility in systemic sclerosis via a mitogen-activated protein kinase kinase (MEK)/extracellular signal-regulated kinase (ERK)-dependent mechanism." *Fibrogenesis & tissue repair* 4(1): 9.
Chen, Y., X. Wang, D. Weng, L. Tian, L. Lv, S. Tao and J. Chen (2009). "A TSP-1 synthetic peptide inhibits bleomycin-induced lung fibrosis in mice." *Experimental and Toxicologic Pathology* 61(1): 59-65.

(Continued)

*Primary Examiner* — Karlheinz R Skowronek
*Assistant Examiner* — Catherine Mader
(74) *Attorney, Agent, or Firm* — Ballard Spahr LLP

(57) ABSTRACT

The present disclosure relates to compounds, compositions and methods for the treatment of diseases through inhibiting the activity of the transforming growth factor beta (TGF-β). More specifically, the disclosed compounds, compositions and methods are useful in the treatment of certain cancers (e.g. multiple myeloma, hematologic malignancies), diseases associated with excessive TGF-β activity including fibrosis, dermal scarring, immune dysfunction, and bone loss by inhibiting the conversion of latent TGF-β to active TGF-β. A method of preventing the activation of TGF-β in pathology is also provided, comprising administering an amount of the compounds sufficient to inhibit conversion of latent TGF-β to active TGF-β by thrombospondin1 (TSP1), resulting in reduced TGF-β activity and reduced adverse effects such as fibrosis, bone loss, and immune dysfunction.

18 Claims, 2 Drawing Sheets

(56) References Cited

PUBLICATIONS

Chipev, C. C., R. Simman, G. Hatch, A. E. Katz, D. M. Siegel and M. Simon (2000). "Myofibroblast phenotype and apoptosis in keloid and palmar fibroblasts in vitro." *Cell Death Differ* 7(2): 166-176.

Connolly, E. C., E. F. Saunier, D. Quigley, M. T. Luu, A. De Sapio, B. Hann, J. M. Yingling and R. J. Akhurst (2011). "Outgrowth of drug-resistant carcinomas expressing markers of tumor aggression after long-term TbetaRI/II kinase inhibition with LY2109761." *Cancer research* 71(6): 2339-2349.

Crawford, S. E., V. Stellmach, J. E. Murphy-Ullrich, S. M. Ribeiro, J. Lawler, R. O. Hynes, G. P. Boivin and N. Bouck (1998). "Thrombospondin-1 is a major activator of TGF-beta1 in vivo." *Cell* 93(7): 1159-1170.

Daniel, C., K. Schaub, K. Amann, J. Lawler and C. Hugo (2007). "Thrombospondin-1 is an endogenous activator of TGF-beta in experimental diabetic nephropathy in vivo." *Diabetes* 56(12): 2982-2989.

Isufi, I., M. Seetharam, L. Zhou, D. Sohal, J. Opalinska, P. Pahanish and A. Verma (2007). "Transforming growth factor-beta signaling in normal and malignant hematopoiesis." *Journal of interferon & cytokine research : the official journal of the International Society for Interferon and Cytokine Research* 27(7): 543-552.

Jou, I. M., A. L. Shiau, S. Y. Chen, C. R. Wang, D. B. Shieh, C. S. Tsai and C. L. Wu (2005). "Thrombospondin 1 as an effective gene therapeutic strategy in collagen-induced arthritis." *Arthritis Rheum* 52(1): 339-344.

Kondou, H., S. Mushiake, Y. Etani, Y. Miyoshi, T. Michigami and K. Ozono (2003). "A blocking peptide for transforming growth factor-beta1 activation prevents hepatic fibrosis in vivo." *Journal of hepatology* 39(5): 742-748.

Kukreja, A., S. Radfar, B. H. Sun, K. Insogna and M. V. Dhodapkar (2009). "Dominant role of CD47-thrombospondin-1 interactions in myeloma-induced fusion of human dendritic cells: implications for bone disease." *Blood* 114(16): 3413-3421.

Lanz, T. V., Z. Ding, P. P. Ho, J. Luo, A. N. Agrawal, H. Srinagesh, R. Axtell, H. Zhang, M. Platten, T. Wyss-Coray and L. Steinman (2010). "Angiotensin II sustains brain inflammation in mice via TGF-beta." *The Journal of clinical investigation* 120(8): 2782-2794.

Liu, S., L. Shi and S. Wang (2007). "Overexpression of upstream stimulatory factor 2 accelerates diabetic kidney injury." *American journal of physiology. Renal physiology* 293(5): F1727-1735.

Longo, V., O. Brunetti, S. D'Oronzo, F. Dammacco and F. Silvestris (2012). "Therapeutic approaches to myeloma bone disease: An evolving story." *Cancer treatment reviews*.

Lu, A., M. Miao, T. R. Schoeb, A. Agarwal and J. E. Murphy-Ullrich (2011). "Blockade of TSP1-dependent TGF-beta activity reduces renal injury and proteinuria in a murine model of diabetic nephropathy." *The American journal of pathology* 178(6): 2573-2586.

Ludlow, A., K. O. Yee, R. Lipman, R. Bronson, P. Weinreb, X. Huang, D. Sheppard and J. Lawler (2005). "Characterization of integrin beta6 and thrombospondin-1 double-null mice." *J Cell Mol Med* 9(2): 421-437.

Matsumoto, T. and M. Abe (2011). "TGF-beta-related mechanisms of bone destruction in multiple myeloma." *Bone* 48(1): 129-134.

Miao, W. M., W. L. Seng, M. Duquette, P. Lawler, C. Laus and J. Lawler (2001). "Thrombospondin-1 type 1 repeat recombinant proteins inhibit tumor growth through transforming growth factor-beta-dependent and -independent mechanisms." *Cancer Res* 61(21): 7830-7839.

Mimura, Y., H. Ihn, M. Jinnin, Y. Asano, K. Yamane and K. Tamaki (2005). "Constitutive thrombospondin-1 overexpression contributes to autocrine transforming growth factor-beta signaling in cultured scleroderma fibroblasts." *Am J Pathol* 166(5): 1451-1463.

Morishima, Y., A. Nomura, Y. Uchida, Y. Noguchi, T. Sakamoto, Y. Ishii, Y. Goto, K. Masuyama, M. J. Zhang, K. Hirano, M. Mochizuki, M. Ohtsuka and K. Sekizawa (2001). "Triggering the induction of myofibroblast and fibrogenesis by airway epithelial shedding." *American journal of respiratory cell and molecular biology* 24(1): 1-11.

Murphy-Ullrich, J. E. and D. F. Mosher (1985). "Localization of thrombospondin in clots formed in situ." *Blood* 66(5): 1098-1104.

Murphy-Ullrich, J. E. and M. Poczatek (2000). "Activation of latent TGF-beta by thrombospondin-1: mechanisms and physiology." *Cytokine & growth factor reviews* 11(1-2): 59-69.

Myung, S. J., J. H. Yoon, G. Y. Gwak, W. Kim, J. I. Yang, S. H. Lee, J. J. Jang and H. S. Lee (2007). "Bile acid-mediated thrombospondin-1 induction in hepatocytes leads to transforming growth factor-beta-dependent hepatic stellate cell activation." *Biochem Biophys Res Commun* 353(4): 1091-1096.

Naito, T., T. Masaki, D. J. Nikolic-Paterson, C. Tanji, N. Yorioka and N. Kohno (2004). "Angiotensin II induces thrombospondin-1 production in human mesangial cells via p38 MAPK and JNK: a mechanism for activation of latent TGF-beta1." *American journal of physiology. Renal physiology* 286(2): F278-287.

Noonan, K., L. Marchionni, J. Anderson, D. Pardoll, G. D. Roodman and I. Borrello (2010). "A novel role of IL-17-producing lymphocytes in mediating lytic bone disease in multiple myeloma." *Blood* 116(18): 3554-3563.

Nor, J. E., L. Dipietro, J. E. Murphy-Ullrich, R. O. Hynes, J. Lawler and P. J. Polverini (2005). "Activation of Latent TGF-beta1 by Thrombospondin-1 is a Major Component of Wound Repair." *Oral biosciences & medicine : OBM* 2(2): 153-161.

Pierson, B. A., K. Gupta, W. S. Hu and J. S. Miller (1996). "Human natural killer cell expansion is regulated by thrombospondin-mediated activation of transforming growth factor-beta 1 and independent accessory cell-derived contact and soluble factors." *Blood* 87(1): 180-189.

Poczatek, M. H., C. Hugo, V. Darley-Usmar and J. E. Murphy-Ullrich (2000). "Glucose stimulation of transforming growth factor-beta bioactivity in mesangial cells is mediated by thrombospondin-1." *Am J Pathol* 157(4): 1353-1363.

Pohlers, D., A. Beyer, D. Koczan, T. Wilhelm, H. J. Thiesen and R. W. Kinne (2007). "Constitutive upregulation of the transforming growth factor-beta pathway in rheumatoid arthritis synovial fibroblasts." *Arthritis research & therapy* 9(3): R59.

Pour, L., H. Svachova, Z. Adam, M. Almasi, L. Buresova, T. Buchler, L. Kovarova, P. Nemec, M. Penka, J. Vorlicek and R. Hajek (2010). "Levels of angiogenic factors in patients with multiple myeloma correlate with treatment response." *Annals of hematology* 89(4): 385-389.

Prabhala, R. H., D. Pelluru, M. Fulciniti, H. K. Prabhala, P. Nanjappa, W. Song, C. Pai, S. Amin, Y. T. Tai, P. G. Richardson, I. M. Ghobrial, S. P. Treon, J. F. Daley, K. C. Anderson, J. L. Kutok, et al. (2010). "Elevated IL-17 produced by TH17 cells promotes myeloma cell growth and inhibits immune function in multiple myeloma." *Blood* 115(26): 5385-5392.

Prud'homme, G. J. (2007). "Pathobiology of transforming growth factor beta in cancer, fibrosis and immunologic disease, and therapeutic considerations." *Laboratory investigation; a journal of technical methods and pathology* 87(11): 1077-1091.

Raugi, G. J., J. E. Olerud and A. M. Gown (1987). "Thrombospondin in early human wound tissue." *J Invest Dermatol* 89(6): 551-554.

Reed, M. J., P. Puolakkainen, T. F. Lane, D. Dickerson, P. Bornstein and E. H. Sage (1993). "Differential expression of SPARC and thrombospondin 1 in wound repair: immunolocalization and in situ hybridization." *J Histochem Cytochem* 41(10): 1467-1477.

Sakai, K., Y. Sumi, H. Muramatsu, K. Hata, T. Muramatsu and M. Ueda (2003). "Thrombospondin-1 promotes fibroblast-mediated collagen gel contraction caused by activation of latent transforming growth factor beta-1." *J Dermatol Sci* 31(2): 99-109.

Sasaki, A., H. Naganuma, E. Satoh, T. Kawataki, K. Amagasaki and H. Nukui (2001). "Participation of thrombospondin-1 in the activation of latent transforming growth factor-beta in malignant glioma cells." *Neurologia medico-chirurgica* 41(5): 253-258; discussion 258-259.

Schultz-Cherry, S. and J. E. Murphy-Ullrich (1993). "Thrombospondin causes activation of latent transforming growth factor-β secreted by endothelial cells by a novel mechanism." *J Cell Biol* 122(4): 923-932.

(56) References Cited

OTHER PUBLICATIONS

Takeuchi, K., M. Abe, M. Hiasa, A. Oda, H. Amou, S. Kido, T. Harada, O. Tanaka, H. Miki, S. Nakamura, A. Nakano, K. Kagawa, K. Yata, S. Ozaki and T. Matsumoto (2010). "Tgf-Beta inhibition restores terminal osteoblast differentiation to suppress myeloma growth." *PloS one* 5(3): e9870.

Ueno, A., Y. Miwa, K. Miyoshi, T. Horiguchi, H. Inoue, I. Ruspita, K. Abe, K. Yamashita, E. Hayashi and T. Noma (2006). "Constitutive expression of thrombospondin 1 in MC3T3-E1 osteoblastic cells inhibits mineralization." *J Cell Physiol* 209(2): 322-332.

Urashima, M., A. Ogata, D. Chauhan, M. Hatziyanni, M. B. Vidriales, D. A. Dedera, R. L. Schlossman and K. C. Anderson (1996). "Transforming growth factor-beta1: differential effects on multiple myeloma versus normal B cells." *Blood* 87(5): 1928-1938.

Wahab, N. A., L. Schaefer, B. S. Weston, O. Yiannikouris, A. Wright, A. Babelova, R. Schaefer and R. M. Mason (2005). "Glomerular expression of thrombospondin-1, transforming growth factor beta and connective tissue growth factor at different stages of diabetic nephropathy and their interdependent roles in mesangial response to diabetic stimuli." *Diabetologia* 48(12): 2650-2660.

Wang, S., S. Shiva, M. H. Poczatek, V. Darley-Usmar and J. E. Murphy-Ullrich (2002). "Nitric oxide and cGMP-dependent protein kinase regulation of glucose-mediated thrombospondin 1-dependent transforming growth factor-beta activation in mesangial cells." *J Biol Chem* 277(12): 9880-9888.

Wang, S., J. Skorczewski, X. Feng, L. Mei and J. E. Murphy-Ullrich (2004). "Glucose up-regulates thrombospondin 1 gene transcription and transforming growth factor-beta activity through antagonism of cGMP-dependent protein kinase repression via upstream stimulatory factor 2." *J Biol Chem* 279(33): 34311-34322.

Xie, X. S., F. Y. Li, H. C. Liu, Y. Deng, Z. Li and J. M. Fan (2010). "LSKL, a peptide antagonist of thrombospondin-1, attenuates renal interstitial fibrosis in rats with unilateral ureteral obstruction." *Archives of pharmacal research* 33(2): 275-284.

Yang, K., J. L. Vega, M. Hadzipasic, J. P. Schatzmann Peron, B. Zhu, Y. Carrier, S. Masli, L. V. Rizzo and H. L. Weiner (2009). "Deficiency of thrombospondin-1 reduces Th17 differentiation and attenuates experimental autoimmune encephalomyelitis." *J Autoimmun.*

Yang, Y. L., L. Y. Chuang, J. Y. Guh, S. F. Liu, M. Y. Hung, T. N. Liao and Y. L. Huang (2004). "Thrombospondin-1 mediates distal tubule hypertrophy induced by glycated albumin." *The Biochemical journal* 379(Pt 1): 89-97.

Yee, K. O., M. Streit, T. Hawighorst, M. Detmar and J. Lawler (2004). "Expression of the type-1 repeats of thrombospondin-1 inhibits tumor growth through activation of transforming growth factor-beta." *Am J Pathol* 165(2): 541-552.

Yehualaeshet, T., R. O'Connor, A. Begleiter, J. E. Murphy-Ullrich, R. Silverstein and N. Khalil (2000). "A CD36 synthetic peptide inhibits bleomycin-induced pulmonary inflammation and connective tissue synthesis in the rat." *Am J Respir Cell Mol Biol* 23(2): 204-212.

Yehualaeshet, T., R. O'Connor, J. Green-Johnson, S. Mai, R. Silverstein, J. E. Murphy-Ullrich and N. Khalil (1999). "Activation of rat alveolar macrophage-derived latent transforming growth factor beta-1 by plasmin requires interaction with thrombospondin-1 and its cell surface receptor, CD36." *The American journal of pathology* 155(3): 841-851.

Yevdokimova, N., N. A. Wahab and R. M. Mason (2001). "Thrombospondin-1 is the key activator of TGF-beta1 in human mesangial cells exposed to high glucose." *J Am Soc Nephrol* 12(4): 703-712.

Young, G. D. and J. E. Murphy-Ullrich (2004). "Molecular interactions that confer latency to transforming growth factor-beta." *J Biol Chem* 279(36): 38032-38039.

Zamiri, P., S. Masli, N. Kitaichi, A. W. Taylor and J. W. Streilein (2005). "Thrombospondin plays a vital role in the immune privilege of the eye." *Invest Ophthalmol Vis Sci* 46(3): 908-919.

Zhou, Y., J. S. Hagood and J. E. Murphy-Ullrich (2004). "Thy-1 expression regulates the ability of rat lung fibroblasts to activate transforming growth factor-beta in response to fibrogenic stimuli." *The American journal of pathology* 165(2): 659-669.

Zhou, Y., M. H. Poczatek, K. H. Berecek and J. E. Murphy-Ullrich (2006). "Thrombospondin 1 mediates angiotensin II induction of TGF-beta activation by cardiac and renal cells under both high and low glucose conditions." *Biochem Biogthrs Res Commun* 339(2): 633-641.

\* cited by examiner

Figure 1: Compound No.1 (30 mg/kg) tibial bone loss in the SCID/CAG - hpse MM model

COMPOUNDS, COMPOSITIONS AND METHODS FOR THE TREATMENT OF DISEASES THROUGH INHIBITING TGF-β ACTIVITY

CROSS REFERENCE TO RELATED APPLICATIONS

The present application claims priority from U.S. provisional application Ser. No. 61/822,008 filed on May 10, 2013, entire disclosure of which is incorporated herein by reference.

FIELD OF THE INVENTION

The present disclosure relates to compounds, compositions and methods for the treatment of diseases through inhibiting the activity of the transforming growth factor beta (TGF-β). More specifically, the disclosed compounds, compositions and methods are useful in the treatment of certain cancers (e.g. multiple myeloma, hematologic malignancies), and diseases associated with excessive TGF-β activity including fibrosis, immune dysfunction, bone loss, and dermal scarring, by inhibiting the conversion of latent TGF-β to active TGF-β. A method of preventing the activation of TGF-β in pathology is also provided, comprising administering an amount of the compounds sufficient to inhibit conversion of latent TGF-β to active TGF-β by thrombospondin1 (TSP1), resulting in reduced TGF-β activity and reduced adverse effects such as fibrosis, bone loss, and immune dysfunctions such as rheumatoid arthritis and chronic renal allograft rejection.

BACKGROUND OF THE INVENTION

A. The Role of TGF-β in Multiple Myeloma (MM)

Multiple myeloma (MM) is a cancer of plasma cells and the second most common hematologic malignancy. There are ~75,000 people in the US with MM and 21,700 cases are diagnosed yearly. MM accounts for 20% of deaths from hematologic malignancies. Disease morbidity and mortality result from immune dysfunction with infection, anemia, and renal failure due to high immunoglobulin levels. Osteolytic bone disease is a significant complication of MM: not only is bone loss and fracture responsible for diminished quality of life, but the osteolytic bone environment also directly supports MM cell growth. MM progression is profoundly influenced by the bone marrow microenvironment. (Anderson and Carrasco 2011; Longo et al. 2012). Major advances in survival have come from novel therapies that target this microenvironment. Nonetheless, MM eventually becomes resistant to current therapies, indicating a significant need for new therapeutic approaches.

TGF-β plays multiple roles in MM progression. TGF-β is a growth factor, abundant in platelets and bone, which plays key roles in growth regulation, stimulation of the extracellular matrix (ECM) and cell adhesion, and in immune cell regulation. TGF-β signals through a hetero-tetrameric receptor complex to activate Smads and other pathways. TGF-β is expressed at high levels by both MM cells and by bone marrow stromal cells: TGF-β is not a tumor suppressor for MM cells as they are resistant to the direct suppressive effects of TGF-β due to receptor defects. (Urashima et al. 1996; Hayashi et al. 2004). Rather, TGF-β impacts MM by altering the tumor microenvironment through exacerbation of lytic bone disease, impairment of immune responses, stimulation of angiogenesis, and impairment of hematopoiesis. (Urashima et al. 1996; Dong and Blobe 2006; Isufi et al. 2007; Takeuchi et al. 2010; Matsumoto and Abe 2011; Longo et al. 2012).

Many aspects of the reduced quality of life for patients with MM such as osteolytic bone disease and immune dysfunction are a consequence of TGF-β action and agents to reduce TGF-β action will reduce morbidity. TGF-β increases interleukin 6 (IL-6) secretion by MM cells and associated bone marrow stromal cells. (Urashima et al. 1996). TGF-β is important in Th17 T cell development, which promotes MM growth and impairs normal immune function. (Prabhala et al. 2010). Furthermore, interleukin 17 (IL-17) producing lymphocytes mediate lytic bone disease in MM. (Noonan et al. 2010). TGF-β is a central regulator of ECM protein and integrin expression, which augments MM cell adhesion to bone ECM and bone marrow stromal cells, especially through up-regulation of integrin $\alpha_4\beta_1$ (Very Late Antigen-4 or VLA-4). In MM, TGF-β increases in vivo angiogenesis through vascular endothelial growth factor (VEGF) stimulation. (Hayashi et al. 2004). TGF-β receptor kinase inhibitors downregulate IL-6 and VEGF and reduce MM cell adhesion to bone marrow stromal cells and growth. (Hayashi et al. 2004). TGF-β stimulates early osteoblast proliferation, while inhibiting late osteoblast differentiation and mineralization to reduce bone formation. TGF-β also increases bone lytic activity by stimulating the secretion of the receptor activator of nuclear factor kappa-B ligand (RANKL), and enhancement of osteoclast survival. TGF-β is a therapeutic target in metastatic bone disease. (Longo et al. 2012). Similarly, in MM, TGF-β action is associated with lytic bone disease. (Matsumoto and Abe 2011). Moreover, TGF-β inhibition restores terminal osteoblast differentiation to suppress MM growth. (Takeuchi et al. 2010). Blockade of TGF-β reduces MM and bone disease in vitro and in vivo. (Urashima et al. 1996; Takeuchi et al. 2010). Blocking TGF-β activity in the tumor microenvironment enhances anti-tumor immunity, especially in hematologic malignancies. (Dong and Blobe 2006; Isufi et al. 2007; Flavell et al. 2010).

B. Strategies for Regulation of TGF-β Activity in MM

TGF-β is critical for homeostasis: genetic ablation of TGF-β, its receptors, or its signaling mediators results in developmental defects, inflammation, and increased carcinomas. Thus, it is therapeutically advantageous to target only adverse TGF-β activity in MM and spare homeostatic activity. Current anti-TGF-β therapeutics target the molecule itself or downstream signaling pathways and provide no mechanism for distinguishing between homeostatic and disease-related TGF-β activity, thereby increasing the potential for adverse effects. In fact, Smad 2 resistance and increased papilloma incidence in mice treated for 20 weeks with a TGF-β receptor kinase inhibitor have been identified (Connolly et al. 2011) and the 1D11 pan-specific anti-TGF-β neutralizing antibody shows epithelial hyperplasia and progression to carcinoma in some models. (Prud'homme 2007).

TGF-β is secreted as a biologically inactive growth factor and control of the conversion of latent TGF-β to a biologically active growth factor is a major regulatory node. Binding of the N-terminal latency associated peptide (LAP) prevents TGF-β binding to its receptors and this interaction must be disrupted for TGF-β signaling to occur. Latent TGF-β can be converted to the active form through multiple mechanisms that include proteolysis, binding to integrins, mechanical forces, modifications of the latent complex by viral enzymes or by reactive oxygen species, or by binding to the secreted and ECM protein TSP1. (Murphy-Ullrich and Poczatek 2000; Sweetwyne and Murphy-Ullrich 2012). The mechanism that regulates latent TGF-β activation can vary with tissue, cell type, and specific disease milieu. Blockade of the major activation mechanism in a particular disease typically attenuates adverse effects of TGF-β. Thus, it is important to identify the predominant mechanism of TGF-β activation in MM.

C. Thrombospondin 1 (TSP1) Activates Latent TGF-β

TSP1 is a complex multi-functional protein released from platelet α-granules, incorporated into the fibrin clot, and expressed by cell types that participate in wound healing responses in a temporally regulated manner. (Murphy-Ullrich and Mosher 1985; Raugi et al. 1987; Reed et al. 1993; DiPietro et al. 1996; Agah et al. 2002). TSP1 regulates multiple cellular events involved in tissue repair including hemostasis, cell adhesion, migration, proliferation, ECM expression and organization, and regulation of growth factor activity. (Adams and Lawler 2004; Adams and Lawler 2011). In addition to physiologic repair, TSP1 is also expressed at elevated levels in many tissues undergoing fibro-proliferative remodeling and blockade of specific actions of TSP1 or loss of TSP1 expression can attenuate pathologic tissue remodeling. (Poczatek et al. 2000; Hugo 2003; Daniel et al. 2007). TSP1 is a major regulator of latent TGF-β activation. (Murphy-Ullrich and Poczatek 2000). TSP1 also has TGF-β-independent functions in hemostasis, cell adhesion, migration, and growth factor regulation, e.g. regulation of epidermal growth factor (EGF), VEGF, and fibroblast growth factor (FGF). (Adams and Lawler 2011). TSP1 is an endogenous angiogenesis inhibitor via inhibition of VEGF and FGF signaling. TSP1 binding to Cluster of Differentiation 47 (CD47) and Cluster of Differentiation 36 (CD36) blocks nitric oxide signaling.

TSP1 is a secreted ECM protein that controls TGF-β activity by binding and activating latent TGF-β. (Murphy-Ullrich and Poczatek 2000; Sweetwyne and Murphy-Ullrich 2012). TSP1 binds to latent TGF-β to activate TGF-β at the cell surface or in the extracellular milieu. (Sweetwyne and Murphy-Ullrich 2012). Activation occurs through binding of the KRFK (-lysine-arginine-phenylalanine-lysine-) sequence in the TSP1 type 1 repeats (TSRs) to LSKL (-leucine-serine-lysine-leucine-) in the LAP of the latent complex, which disrupts LAP-mature domain interactions to expose the receptor binding sequences on the mature domain, rendering TGF-β capable of signaling. (Young and Murphy-Ullrich 2004). Peptide mimetics of sequences involved in TSP1-TGF-β binding competitively inhibit TSP1-TGF-β activation and studies with these peptides have established TSP1 as a primary regulator of TGF-β bioactivity in different diseases. (Sweetwyne and Murphy-Ullrich 2012). The tetrapeptide LSKL, which competitively blocks TSP-LAP binding, has been used in rodent models to inhibit TSP1-TGF-β activation and attenuate disease. Dose dependent intraperitoneal injection (i.p.) of LSKL improves end organ function in murine diabetic nephropathy and rat cardiomyopathy by blocking TGF-β signaling in target tissues. (Belmadani et al. 2007; Lu et al. 2011). Animals necropsied after 15 weeks of treatment with 30 mg/kg i.p. LSKL, 3 times weekly, showed no inflammation, no tumors in all major organs, and no impairment of wound healing. (Lu et al. 2011).

D. TSP1 and MM

Roles in Immune and Bone Dysfunction

TSP1 is increased in the bone marrow plasma of MM patients. (Kukreja et al. 2009; Pour et al. 2010). TSP1 is increased in the MM microenvironment by factors associated with MM progression, e.g., insulin-like growth factor 1 (IGF-1), IL-6, and TGF-β. TSP1 binds to syndecan-1 (CD138), CD47, and integrins, suggesting that TSP1 bound to the MM cells could locally activate TGF-β.

Immune Cell Regulation:

TSP1 null mice have reduced Th17 T cell differentiation due to decreased IL-17 levels and decreased TGF-β dependent Th17 T cell differentiation, suggesting a role of TSP1 in the TGF-β immune dysregulation in MM. TSP1-TGF-β activation also controls Th17 T cell development in a mouse model of tubule-interstitial fibrosis (UUO). IL-6, a critical factor in TGF-β stimulation of Th17 T cells, regulates TSP1 expression in a cell-type specific manner. TSP1-bound to CD36 on stimulated U937 monocytes stimulates expression and release of IL-6 and also activates latent TGF-β secreted by the monocytes.

Bone Cell Regulation:

TSP1 is expressed in long and flat bones. TSP1 inhibits matrix mineralization of MC3T3-E1 osteoblast precursor cells and it is highly expressed during early osteogenesis. (Ueno et al. 2006). TSP1 in a mixture of platelet proteins inhibits bone nodule formation. IGF-1, a cytokine linked to MM progression, increases TSP1 synthesis by MC3T3-E1 cells and TSP1 increases growth responses of MC3T3 cells to IGF-1 and insulin-like growth factor-binding protein 5 (IGFBP5). It has been shown that MSC genes (MSCs) express TSP1 and that TSP1-TGF-β activation blocks osteogenic differentiation of MSCs. (K. Bailey DuBose et al. 2012). TSP1 also plays a role in osteoclast-mediated bone resorption. Antibody to TSP1 blocks osteoclast mediated bone resorption in vitro. (Kukreja et al. 2009). TSP1 added to dentine slices increased bone resorption through binding to CD36. (Carron et al. 1995). TSP1 binding to macrophage CD36 is required for TSP1-TGF-β activation by bleomycin-treated alveolar macrophages and could similarly regulate activation in osteoclasts.

Dendritic Cells:

MM cells fuse with immature dendritic cells to form osteoclast-like cells which promote bone resorption and MM cell proliferation. (Kukreja et al. 2009). TSP1-binding to CD47 on MM cells is required for osteoclast-like trans-differentiation of immature dendritic cells. (Kukreja et al. 2009). Myeloma-dendritic cell fusion upregulates TSP1 expression. (Kukreja et al. 2009). These data implicate TSP1 in MM catabolic bone disease through TGF-β dependent and independent mechanisms.

E. Biological Roles of TSP1-Dependent TGF-β Activation

In vitro studies have shown that TSP1 activates latent TGF-β secreted by multiple cell types including endothelial cells, mesangial cells, hepatic stellate cells and skin, lung, and cardiac fibroblasts, T cells, and macrophages. (Schultz-Cherry and Murphy-Ullrich 1993; Yehualaeshet et al. 1999; Murphy-Ullrich and Poczatek 2000; Poczatek et al. 2000; Yevdokimova et al. 2001; Zhou et al. 2004; Breitkopf et al. 2005; Mimura et al. 2005; Zhou et al. 2006; Yang et al. 2009). Peptides such as LSKL or WxxW which block TSP1 binding to the latent complex and antibodies which block TSP1-dependent TGF-β activation such as monoclonal antibody 133 (Mab 133) have been used to establish the involvement of endogenous TSP1 in TGF-β activation in a number of disease conditions and physiologic processes. The following Table 1 provides an overview:

TABLE 1

Diseases associated with TSP1 regulation of TGF-β activation

| Disease | Organ/Tissue | In vitro | In vivo model | TSP1 antagonist | References |
|---|---|---|---|---|---|
| Diabetes | Kidney | Mesangial cells in high glucose; glycated albumin | Mice, STZ and Akita, TSP1 null; USF2 transgenic | GGWSHW LSKL Mab 133 | (Poczatek et al. 2000) (Yevdokimova et al. 2001) (Yang et al. 2004; Wahab et al. 2005; Daniel et al. 2007; Liu et al. 2007; Lu et al. 2011) |
| Diabetes/Hypertension | Heart | Rat cardiac fibroblasts; mesangial cells | Rats, STZ with aortic coarctation | LSKL Mab 133 | (Naito et al. 2004) (Zhou et al. 2006) (Belmadani et al. 2007) |
| Mesangial Proliferative glomerulo-nephritis | Kidney | | Rats, Anti-Thy-1 antibody injury | LSKL, AAWSHW Anti-sense oligonucleotides | (Daniel et al. 2004) (Daniel et al. 2003) |
| Chronic Kidney Disease | Kidney | | Rat, UUO | LSKL | (Xie et al. 2010) |
| Bleomycin-induced lung fibrosis | lung | Lung fibroblasts (bleomycin, IL-4) | Rats, mice Bleomycin-treated | LSKL, WSxW in vitro; CD36 binding peptides in vivo | (Zhou et al. 2004) (Yehualaeshet et al. 2000; Chen et al. 2009) |
| Asthma airway remodeling | lung | airway epithelium-fibroblast co-cultures | | LSKL | (Morishima et al. 2001) |
| Liver fibrosis | liver | | Rat, DMN-induced | LSKL | (Kondou et al. 2003) |
| | | Hepatic stellate cells: PDGF, TNF-α | | LSKL | (Breitkopf et al. 2005) |
| | | Hepatocytes, bile acid | | LSKL | (Myung et al. 2007) |
| Scleroderma | skin | Scleroderma fibroblasts | | Anti-sense oligos, Mab 133, GGWSHW | (Mimura et al. 2005) |
| Systemic Sclerosis | Fibroblast contractility | LSKL, siRNA | | | (Chen et al. 2011) |
| Autoimmune disease | Dermis | Dendritic cells; Human peripheral blood T cells | | Mab133, LSKL | (Derks et al. 2007) |
| | Eye | RPE | | Anti-TSP antibody, TSP1 (−/−) | (Futagami et al. 2007) (Zamiri et al. 2005) |
| | | NK cells | | Anti-TGF-β antibody | (Pierson et al. 1996) |
| | MS/Brain inflammation Th17 in EAE | | EAE model of MS with Ang II EAE MOG peptide/TSP1 knockout | LSKL, candesartan TSP1 (−/−) | (Lanz et al. 2010) (Yang et al. 2009) |
| Rheumatoid Arthritis | Synovium | RA synovial fibroblasts | Rats, Collagen-induced arthritis | Adenoviral TSP1 | (Jou et al. 2005) (Pohlers et al. 2007) |
| Wound healing | Skin | Dermal fibroblast cultures | Mouse, excisional wound healing; | TSP1 (−/−); KRFK, KFK-fatty acid | (Cauchard et al. 2004; Nor et al. 2005) |
| Cancer | | glioma | | Antibodies to TSP1 | (Sasaki et al. 2001) |
| | | Tamoxifen, MCF7, T47D mammary carcinoma | | WSHW, anti-CD47, anti-αvβ3 antibody | (Harpel et al. 2001) |
| | | | Mice, subcutaneous B16F10 melanoma | RFK-$2^{nd}$ TSR | (Miao et al. 2001) |

TABLE 1-continued

Diseases associated with TSP1 regulation of TGF-β activation

| Disease | Organ/Tissue | In vitro | In vivo model | TSP1 antagonist | References |
|---------|--------------|----------|---------------|-----------------|------------|
|         |              |          | Mice, A431 squamous cell carcinoma | RFK-TSR | (Yee et al. 2004) |
|         |              | Tumor stoma collagen and nanoparticle delivery | HSTS26T fibrosarcoma, Mu89 melanoma | losartan | (Diop-Frimpong et al. 2011) |

Initial evidence for an in vivo role of TSP1 in latent TGF-β activation was shown by the ability of the KRFK peptide administered in the perinatal period to partially rescue the abnormal TSP-1 null phenotype, in particular airway epithelial hyperplasia and pancreatic islet hyperplasia/acinar hypoplasia. (Crawford et al. 1998). Furthermore, treatment of wild type mice with the LSKL blocking peptide in the perinatal period replicated features of the TSP1 knockout phenotype in the airways and pancreas. Double knockout of both $\beta_6$ integrin and TSP1 results in a phenotype distinct from either single knockout that is characterized by severe inflammation, cardiac degeneration, and epithelial hyperplasia, suggesting both separate and synergistic roles in regulating latent TGF-β activation. (Ludlow et al. 2005). However, it is likely that the primary role for TSP1 in controlling TGF-β activation is during injury, under stress, and in pathologic conditions, rather than during development. The expression of TSP1 is induced by factors associated with systemic diseases with fibrotic end organ involvement including high glucose, reactive oxygen species, and angiotensin II. (Yevdokimova et al. 2001; Wang et al. 2002; Wang et al. 2004; Zhou et al. 2006). Indeed there is evidence from studies utilizing TSP1 antagonist peptides and diabetic TSP1 knockout mice that TSP1 is a major factor in the development of fibrotic end organ complications in diabetes. (Belmadani et al. 2007; Daniel et al. 2007; Lu et al. 2011). Treatment with i.p. injections of LSKL, but not LSAL (leucine-serine-alanine-leucine) control peptide, reduced cardiac fibrosis, Smad phosphorylation, and improved left ventricular function. (Belmadani et al. 2007). Similarly, treatment of Akita mice, a model of type 1 diabetes, with i.p. LSKL reduced urinary TGF-β activity and renal phospho-Smad 2/3 levels and improved markers of tubulointerstitial injury and podocyte function. (Lu et al., 2011). Interestingly, several studies have shown that TSP1 is involved in alveolar macrophage-dependent TGF-β activation in mouse and rat models of bleomycin-induced pulmonary fibrosis and treatment with either TSP1 or CD36 antagonist peptides can ameliorate lung fibrosis and reduce active TGF-β. (Chen et al., 2009; Yehualaeshet et al., 2000).

F. TSP1-Dependent TGF-β Activation in Wound Healing

One of the roles of TSP1 in dermal wound healing appears to be regulating the activation of latent TGF-β. The phenotype of excisional wound healing in the TSP1 null mouse is consistent with a decrease in local TGF-β activation (Agah et al. 2002) and is characterized by a delay in macrophage recruitment and capillary angiogenesis and a persistence of granulation tissue, neovascularization, and inflammation. (Nor et al. 2005). Topical treatment of TSP1 null wounds with the KRFK activating peptide largely rescued the TSP1 null wound phenotype. (Nor et al. 2005). TGF-β levels in these wounds were increased following KRFK treatment and the effects of the KRFK peptide were blocked by a pan-specific anti-TGF-β antibody. While these data suggest that TSP1 plays a role in local activation of TGF-β during wounding, the studies of Agah et al., concluded that the decreased active and total TGF-β in the wounds of TSP1 or TSP1/TSP2 null mice is indirect and primarily due to defects in macrophage recruitment to wounds (a major source of TGF-β in wounds) leading to an overall reduction in TGF-β rather than a defect in activation. (Agah et al. 2002). Despite this controversy, it is clear that TSP1 has the potential to modify the wound healing process. Subcutaneous implantation of TSP1 soaked sponges increased levels of active TGF-β, gel contraction and fibroblast migration. (Sakai et al. 2003). Overexpression of TSP1 in keloids and in scleroderma correlates with increased TGF-β activity. (Chipev et al. 2000; Mimura et al. 2005; Chen et al. 2011). Others have used a derivative of the KRFK sequence, KFK (lysine-phenylalanine-lysine) coupled to a fatty acyl moiety to locally activate TGF-β and increase TIMP-1, which reduces MMP-induced elastin and collagen degradation when applied to dermal fibroblast cultures. (Cauchard et al. 2004). Systemic administration of the LSKL blocking peptide did not reduce Smad signaling or impair dermal wound healing in diabetic mice, although, these studies did not address the effects of direct LSKL administration to the wounds and it is not known if local dermal levels of LSKL following systemic intraperitoneal peptide administration are sufficient to alter local TGF-β activation. (Lu et al. 2011).

Peptides comprising the amino acid sequence LSKL, including the tetrapeptide LSKL, for inhibiting TGF-β activity and the use of these peptides and certain functional derivatives thereof for the treatment of kidney disease are described in U.S. Pat. No. 6,384,189 and U.S. Pat. No. 6,458,767. It is desirable to employ small molecules such as, e.g., LSKL because they are easier to synthesize and, thus, less costly. However, it has been found that LSKL has a plasma stability half-life of only 2.1 minutes, that is, the plasma concentration of LSKL is reduced by half in about 2 minutes. Accordingly, there is a need for small molecules which affect the activation of TGF-β and which also have an extended plasma stability half-life.

SUMMARY OF THE INVENTION

It has surprisingly been found that the compounds disclosed herein effectively inhibit the activity of TGF-β. Additionally, it has surprisingly been found that the plasma stability half-life of compounds disclosed herein is significantly longer than that of LSKL. Accordingly, the compounds disclosed herein, and compositions comprising them, are particularly suited to modulate TGF-β activity and for treating diseases associated with a dysregulation of TGF-β.

In a first aspect, the present disclosure pertains to a compound of formula (I)

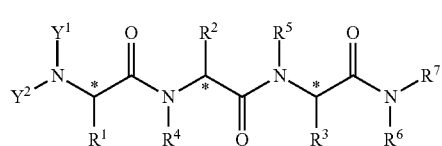

wherein * designates a chiral center of R or S configuration when the carbon atom so marked carries at most one hydrogen substituent, $Y^1$, $R^4$, $R^5$, and $R^6$, are identical or different and are hydrogen, $C_1$-$C_4$-alkyl which is optionally substituted by $C_3$-$C_6$-cycloalkyl or aryl, or are $C_3$-$C_6$-cycloalkyl;

$Y^2$ is hydrogen, $C_1$-$C_4$-alkyl which is optionally substituted by $C_3$-$C_6$-cycloalkyl or aryl, or is $C_3$-$C_6$-cycloalkyl or $COR^a$;

$R^a$ is hydrogen, $C_1$-$C_4$-alkyl, $C_3$-$C_6$-cycloalkyl, or optionally substituted aryl;

$R^1$ is hydrogen, $C_1$-$C_6$-alkyl, $C_1$-$C_4$-alkyl which is substituted by hydroxyl or $OR^b$, or
is optionally substituted $C_3$-$C_6$-cycloalkyl or optionally substituted 5- or 6-membered heterocyclyl;

$R^b$ is $C_1$-$C_6$-alkyl, $C_3$-$C_6$-cycloalkyl, or optionally substituted 5- or 6-membered heterocyclyl;

$R^2$ is $C_1$-$C_6$-alkyl which is substituted by 5- or 6-membered heterocyclyl or $NR^cR^d$; or
is $C_3$-$C_6$-cycloalkyl which is optionally substituted by $C_1$-$C_4$-alkyl, 5- or 6-membered heterocyclyl or $NR^cR^d$;

$R^c$ is hydrogen or $C_1$-$C_4$-alkyl; and $R^d$ is hydrogen, $C_1$-$C_4$-alkyl, $C_3$-$C_6$-cycloalkyl or $C(=O)$ $C_1$-$C_4$-alkyl; preferably $R^d$ is hydrogen, $C_1$-$C_4$-alkyl or $C_3$-$C_6$-cycloalkyl; or $R^c$ and $R^d$ together with the nitrogen to which they are bonded form an optionally substituted 5- or 6-membered heterocycle;

$R^3$ is optionally substituted $C_1$-$C_6$-alkyl, or optionally substituted $C_3$-$C_6$-cycloalkyl; and $R^7$ is hydrogen, $C_1$-$C_6$-alkyl, $C_1$-$C_4$-alkyl which is substituted by $C_3$-$C_6$-cycloalkyl or aryl, or is optionally substituted $C_3$-$C_6$-cycloalkyl;

and to derivatives thereof selected from the group consisting of pharmaceutically acceptable salts, prodrugs, deuterated forms, radio-actively labeled forms, stereo isomers, solvates and combinations thereof.

In a second aspect, the present disclosure pertains to the compound according to the foregoing first aspect which is represented by formula (II)

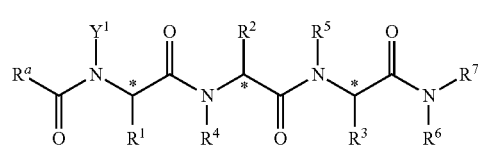

wherein
$R^a$ is $C_1$-$C_4$-alkyl, $C_3$-$C_6$-cycloalkyl, or optionally substituted aryl;
and to derivatives thereof selected from the group consisting of pharmaceutically acceptable salts, prodrugs, deuterated forms, radio-actively labeled forms, stereo isomers, solvates and combinations thereof.

In a third aspect, the present disclosure pertains to the compound according to either one of the foregoing aspects which is represented by formula (III)

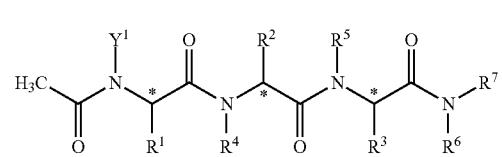

wherein
$R^2$ is $C_1$-$C_6$-alkyl which is substituted by 5- or 6-membered heterocyclyl or $NR^cR^d$;

$R^c$ is hydrogen; and $R^d$ is hydrogen, $C_1$-$C_4$-alkyl, $C_3$-$C_6$-cycloalkyl or $C(=O)$ $C_1$-$C_4$-alkyl; preferably $R^d$ is hydrogen, $C_1$-$C_4$-alkyl or $C_3$-$C_6$-cycloalkyl; or $R^c$ and $R^d$ together with the nitrogen to which they are bonded form an optionally substituted 5- or 6-membered heterocycle;

and to derivatives thereof selected from the group consisting of pharmaceutically acceptable salts, prodrugs, deuterated forms, radio-actively labeled forms, stereo isomers, solvates and combinations thereof.

In a fourth aspect, the present disclosure pertains to the compounds and derivatives according to either one of the foregoing aspects, wherein $R^1$ is $C_1$-$C_4$-alkyl which is substituted by hydroxyl.

In a fifth aspect, the present disclosure pertains to the compounds and derivatives according to either one of the foregoing aspects, wherein $R^3$ is $C_1$-$C_6$-alkyl which is optionally substituted by $C_3$-$C_6$-cycloalkyl or aryl, or is $C_3$-$C_6$-cycloalkyl.

In a sixth aspect, the present disclosure pertains to the compounds and derivatives selected form the group consisting of

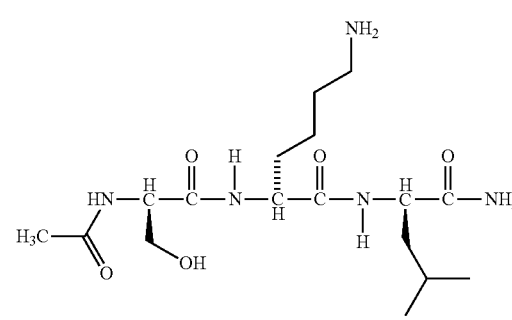

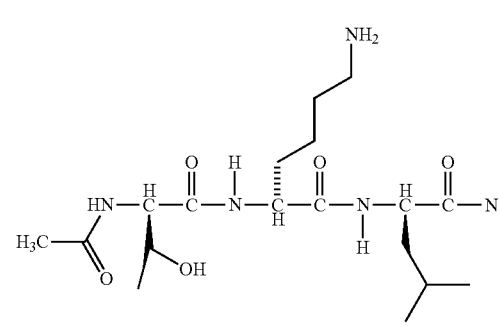

-continued

13
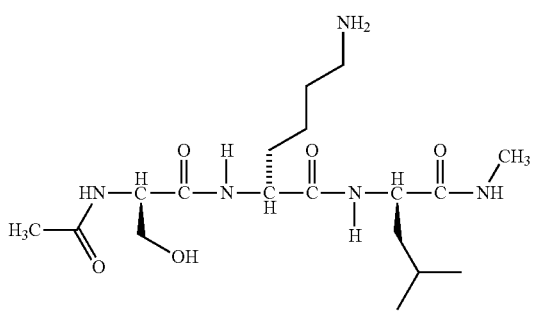

14
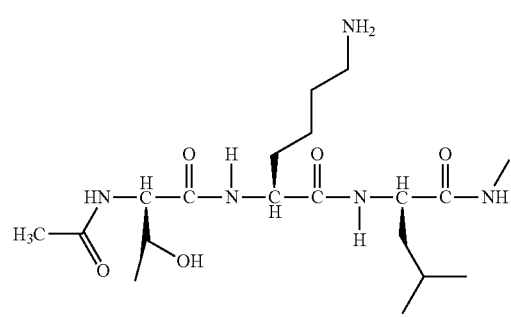

37
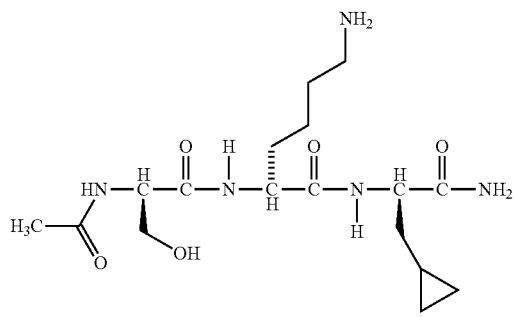

95
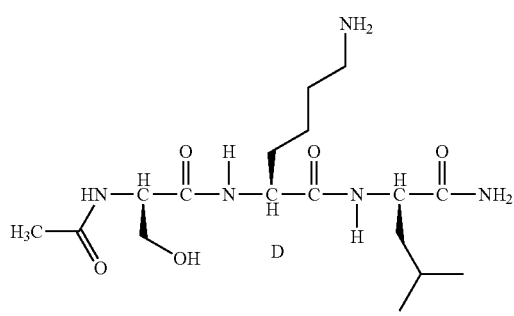

96
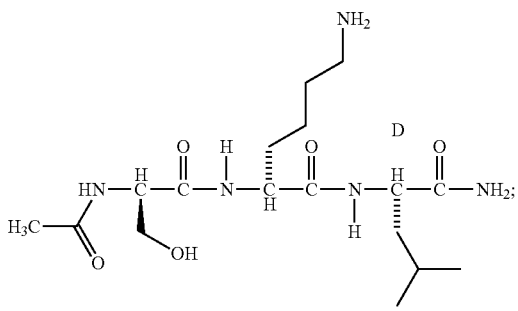

or a derivative thereof selected from the group consisting of pharmaceutically acceptable salts, prodrugs, deuterated forms, radio-actively labeled forms, stereo isomers, solvates and combinations thereof.

In a seventh aspect, the present disclosure pertains to a pharmaceutical composition comprising a compound or derivative according to any one of the foregoing aspects, and a pharmaceutically acceptable carrier.

In an eighth aspect, the present disclosure pertains to a method of treating a patient suffering from a disease or dysfunction associated with abnormal and increased TGF-β activity, which comprises administering to the patient an effective amount of at least one compound of formula (I.a)

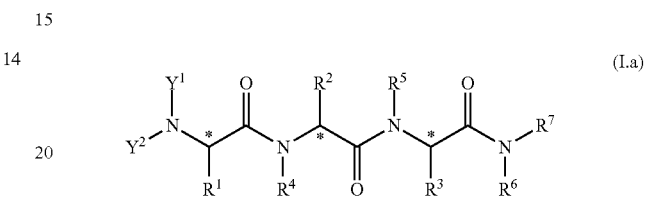
(I.a)

wherein * designates a chiral center of R or S configuration when the carbon atom so marked carries at most one hydrogen substituent, $Y^1, R^4, R^5$, and $R^6$, are identical or different and are hydrogen, $C_1$-$C_4$-alkyl which is optionally substituted by $C_3$-$C_6$-cycloalkyl or aryl, or are $C_3$-$C_6$-cycloalkyl;

$Y^2$ is hydrogen, $C_1$-$C_4$-alkyl which is optionally substituted by $C_3$-$C_6$-cycloalkyl or aryl, or is $C_3$-$C_6$-cycloalkyl or $COR^a$;

$R^a$ is hydrogen, $C_1$-$C_4$-alkyl, $C_3$-$C_6$-cycloalkyl, or optionally substituted aryl;

$R^1$ is hydrogen, $C_1$-$C_6$-alkyl, $C_1$-$C_4$-alkyl which is substituted by hydroxyl or $OR^b$, or
is optionally substituted $C_3$-$C_6$-cycloalkyl or optionally substituted 5- or 6-membered heterocyclyl;

$R^b$ is $C_1$-$C_6$-alkyl, $C_3$-$C_6$-cycloalkyl, or optionally substituted 5- or 6-membered heterocyclyl;

$R^2$ is $C_1$-$C_6$-alkyl which is optionally substituted by 5- or 6-membered heterocyclyl or $NR^cR^d$; or
is $C_3$-$C_6$-cycloalkyl which is optionally substituted by $C_1$-$C_4$-alkyl, 5- or 6-membered heterocyclyl or $NR^cR^d$;

$R^c$ is hydrogen or $C_1$-$C_4$-alkyl; and $R^d$ is hydrogen, $C_1$-$C_4$-alkyl, $C_3$-$C_6$-cycloalkyl or C(=O)$C_1$-$C_4$-alkyl; preferably $R^d$ is hydrogen, $C_1$-$C_4$-alkyl or $C_3$-$C_6$-cycloalkyl; or $R^c$ and $R^d$ together with the nitrogen to which they are bonded form an optionally substituted 5- or 6-membered heterocycle;

$R^3$ is optionally substituted $C_1$-$C_6$-alkyl, or optionally substituted $C_3$-$C_6$-cycloalkyl; and $R^7$ is hydrogen, $C_1$-$C_6$-alkyl, $C_1$-$C_4$-alkyl which is substituted by $C_3$-$C_6$-cycloalkyl or aryl, or is optionally substituted $C_3$-$C_6$-cycloalkyl;

or a derivative thereof selected from the group consisting of pharmaceutically acceptable salts, prodrugs, deuterated forms, radio-actively labeled forms, stereo isomers, solvates and combinations thereof.

In a ninth aspect, the present disclosure pertains to the method according to the foregoing eighth aspect, wherein $R^2$ is $C_1$-$C_6$-alkyl which is substituted by 5- or 6-membered heterocyclyl or $NR^cR^d$; or
is $C_3$-$C_6$-cycloalkyl which is optionally substituted by $C_1$-$C_4$-alkyl, 5- or 6-membered heterocyclyl, or $NR^cR^d$;

$R^c$ is hydrogen or $C_1$-$C_4$-alkyl; and $R^d$ is hydrogen, $C_1$-$C_4$-alkyl, $C_3$-$C_6$-cycloalkyl or C(=O)$C_1$-$C_4$-alkyl; preferably $R^d$ is hydrogen, $C_1$-$C_4$-alkyl or $C_3$-$C_6$-cycloalkyl; or $R^c$ and $R^d$ together with the nitrogen to which they are bonded form an optionally substituted 5- or 6-membered heterocycle.

In a tenth aspect, the present disclosure pertains to the method according to either one of the foregoing aspects eight and nine, wherein the at least one compound is represented by formula (II.a)

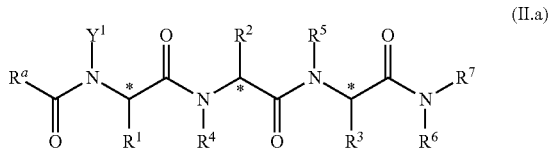

wherein $R^a$ is $C_1$-$C_4$-alkyl, $C_3$-$C_6$-cycloalkyl, or optionally substituted aryl;

or a derivative thereof selected from the group consisting of pharmaceutically acceptable salts, prodrugs, deuterated forms, radio-actively labeled forms, stereo isomers, solvates and combinations thereof.

In an eleventh aspect, the present disclosure pertains to the method according to either one of the foregoing aspects eight to ten, wherein the at least one compound is represented by formula (III.a)

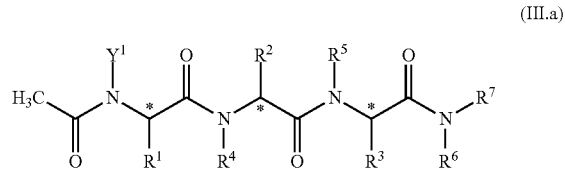

wherein $R^2$ is $C_1$-$C_6$-alkyl which is substituted by 5- or 6-membered heterocyclyl or $NR^cR^d$;

$R^c$ is hydrogen; and $R^d$ is hydrogen, $C_1$-$C_4$-alkyl, $C_3$-$C_6$-cycloalkyl or C(=O)$C_1$-$C_4$-alkyl; preferably $R^d$ is hydrogen, $C_1$-$C_4$-alkyl or $C_3$-$C_6$-cycloalkyl; or $R^c$ and $R^d$ together with the nitrogen to which they are bonded form an optionally substituted 5- or 6-membered heterocycle;

or a derivative thereof selected from the group consisting of pharmaceutically acceptable salts, prodrugs, deuterated forms, radio-actively labeled forms, stereo isomers, solvates and combinations thereof.

In a twelfth aspect, the present disclosure pertains to the method according to either one of the foregoing aspects eight to eleven, wherein $R^1$ is $C_1$-$C_4$-alkyl which is substituted by hydroxyl.

In a thirteenth aspect, the present disclosure pertains to the method according to either one of the foregoing aspects eight to twelve, wherein $R^3$ is $C_1$-$C_6$-alkyl which is optionally substituted by $C_3$-$C_6$-cycloalkyl or aryl, or is $C_3$-$C_6$-cycloalkyl.

In a fourteenth aspect, the present disclosure pertains to the method according to either one of the foregoing aspects eight to thirteen, wherein the disease or dysfunction associated with abnormal and increased TGF-β is a cancer.

In a fifteenth aspect, the present disclosure pertains to the method according to the foregoing fourteenth aspect, wherein the cancer is multiple myeloma or a hematologic malignancy.

In a sixteenth aspect, the present disclosure pertains to the method according to either one of the foregoing aspects eight to thirteen, wherein the disease or dysfunction associated with abnormal and increased TGF-β is a fibrotic condition.

In a seventeenth aspect, the present disclosure pertains to the method in accordance with the foregoing sixteenth aspect, wherein the fibrotic condition is found in the liver, the lung, the cardiac muscle, the kidney, the skin, or the eye.

In an eighteenth aspect, the present disclosure pertains to the method in accordance with the foregoing seventeenth aspect, wherein the fibrotic condition is glaucoma.

In a nineteenth aspect, the present disclosure pertains to the method according to either one of the foregoing aspects eight to thirteen, wherein the disease or dysfunction associated with abnormal and increased TGF-β is an immune dysfunction.

In a twentieth aspect, the present disclosure pertains to the method in accordance with the foregoing nineteenth aspect, wherein the immune dysfunction is rheumatoid arthritis or chronic renal allograft rejection.

In a twenty-first aspect, the present disclosure pertains to the method according to either one of the foregoing aspects nine to fourteen, wherein the disease or dysfunction associated with abnormal and increased TGF-β is bone loss.

In a twenty-second aspect, the present disclosure pertains to a method of reducing the activation of TGF-β in a patient adversely affected by abnormal and increased TGF-β activity, which comprises administering to the patient at least one compound of formula (I.a)

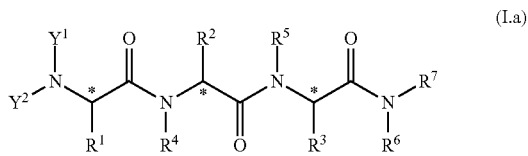

wherein * designates a chiral center of R or S configuration when the carbon atom so marked carries at most one hydrogen substituent, $Y^1$, $R^4$, $R^5$, and $R^6$, are identical or different and are hydrogen, $C_1$-$C_4$-alkyl which is optionally substituted by $C_3$-$C_6$-cycloalkyl or aryl, or are $C_3$-$C_6$-cycloalkyl;

$Y^2$ is hydrogen, $C_1$-$C_4$-alkyl which is optionally substituted by $C_3$-$C_6$-cycloalkyl or aryl, or is $C_3$-$C_6$-cycloalkyl or $COR^a$;

$R^a$ is hydrogen, $C_1$-$C_4$-alkyl, $C_3$-$C_6$-cycloalkyl, or optionally substituted aryl;

$R^1$ is hydrogen, $C_1$-$C_6$-alkyl, $C_1$-$C_4$-alkyl which is substituted by hydroxyl or $OR^b$, or is optionally substituted $C_3$-$C_6$-cycloalkyl or optionally substituted 5- or 6-membered heterocyclyl;

$R^b$ is $C_1$-$C_6$-alkyl, $C_3$-$C_6$-cycloalkyl, or optionally substituted 5- or 6-membered heterocyclyl;

$R^2$ is $C_1$-$C_6$-alkyl which is optionally substituted by 5- or 6-membered heterocyclyl or $NR^cR^d$; or is $C_3$-$C_6$-cycloalkyl which is optionally substituted by $C_1$-$C_4$-alkyl, 5- or 6-membered heterocyclyl or $NR^cR^d$;

$R^c$ is hydrogen or $C_1$-$C_4$-alkyl; and

R$^d$ is hydrogen, C$_1$-C$_4$-alkyl, C$_3$-C$_6$-cycloalkyl or C(=O) C$_1$-C$_4$-alkyl; preferably R$^d$ is hydrogen, C$_1$-C$_4$-alkyl or C$_3$-C$_6$-cycloalkyl; or R$^c$ and R$^d$ together with the nitrogen to which they are bonded form an optionally substituted 5- or 6-membered heterocycle;

R$^3$ is optionally substituted C$_1$-C$_6$-alkyl, or optionally substituted C$_3$-C$_6$-cycloalkyl; and R$^7$ is hydrogen, C$_1$-C$_6$-alkyl, C$_1$-C$_4$-alkyl which is substituted by C$_3$-C$_6$-cycloalkyl or aryl, or is optionally substituted C$_3$-C$_6$-cycloalkyl;

or a derivative thereof selected from the group consisting of pharmaceutically acceptable salts, prodrugs, deuterated forms, radio-actively labeled forms, stereo isomers, solvates and combinations thereof, wherein the at least one compound or derivative is administered in an amount sufficient to reduce or inhibit the activation of latent TGF-β by thrombospondin1 (TSP1).

In a twenty-third aspect, the present disclosure pertains to the method according to the foregoing twenty-two aspect, wherein R$^2$ is C$_1$-C$_6$-alkyl which is substituted by 5- or 6-membered heterocyclyl or NR$^c$R$^d$; or is C$_3$-C$_6$-cycloalkyl which is optionally substituted by C$_1$-C$_4$-alkyl, 5- or 6-membered heterocyclyl, or NR$^c$R$^d$;

R$^c$ is hydrogen or C$_1$-C$_4$-alkyl; and

R$^d$ is hydrogen, C$_1$-C$_4$-alkyl, C$_3$-C$_6$-cycloalkyl or C(=O) C$_1$-C$_4$-alkyl; preferably R$^d$ is hydrogen, C$_1$-C$_4$-alkyl or C$_3$-C$_6$-cycloalkyl; or R$^c$ and R$^d$ together with the nitrogen to which they are bonded form an optionally substituted 5- or 6-membered heterocycle.

In a twenty-fourth aspect, the present disclosure pertains to the method according to either one of the foregoing aspects twenty-two and twenty-three, wherein the at least one compound is represented by formula (II.a)

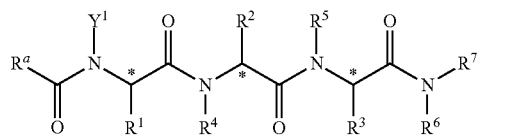

(II.a)

wherein
R$^a$ is C$_1$-C$_4$-alkyl, C$_3$-C$_6$-cycloalkyl, or optionally substituted aryl;

or a derivative thereof selected from the group consisting of pharmaceutically acceptable salts, prodrugs, deuterated forms, radio-actively labeled forms, stereo isomers, solvates and combinations thereof.

In a twenty-fifth aspect, the present disclosure pertains to the method according to either one of the foregoing aspects twenty-two to twenty-four, wherein the at least one compound is represented by formula (III.a)

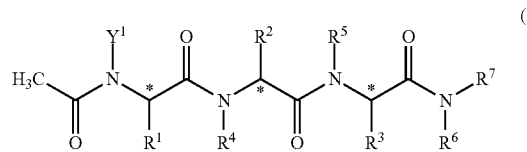

(III.a)

wherein
R$^2$ is C$_1$-C$_6$-alkyl which is substituted by 5- or 6-membered heterocyclyl or NR$^c$R$^d$;

R$^c$ is hydrogen; and

R$^d$ is hydrogen, C$_1$-C$_4$-alkyl, C$_3$-C$_6$-cycloalkyl or C(=O) C$_1$-C$_4$-alkyl; preferably R$^d$ is hydrogen, C$_1$-C$_4$-alkyl or C$_3$-C$_6$-cycloalkyl; or R$^c$ and R$^d$ together with the nitrogen to which they are bonded form an optionally substituted 5- or 6-membered heterocycle;

or a derivative thereof selected from the group consisting of pharmaceutically acceptable salts, prodrugs, deuterated forms, radio-actively labeled forms, stereo isomers, solvates and combinations thereof.

In a twenty-sixth aspect, the present disclosure pertains to the method according to either one of the foregoing aspects twenty-two to twenty-fiver, wherein R$^1$ is C$_1$-C$_4$-alkyl which is substituted by hydroxyl.

In a twenty-seventh aspect, the present disclosure pertains to the method according to either one of the foregoing aspects twenty-two to twenty-six, wherein R$^3$ is C$_1$-C$_6$-alkyl which is optionally substituted by C$_3$-C$_6$-cycloalkyl or aryl, or is C$_3$-C$_6$-cycloalkyl.

In a twenty-eighth aspect, the present disclosure pertains to the method according to either one of the foregoing aspects eight or twelve to twenty-two wherein the at least one compound or derivative is selected form the group consisting of

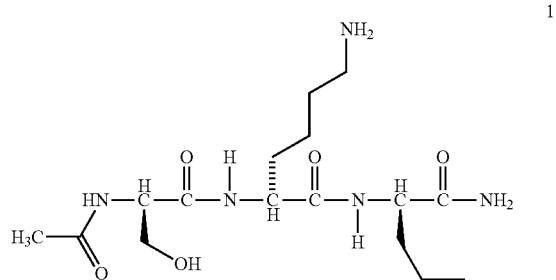

1

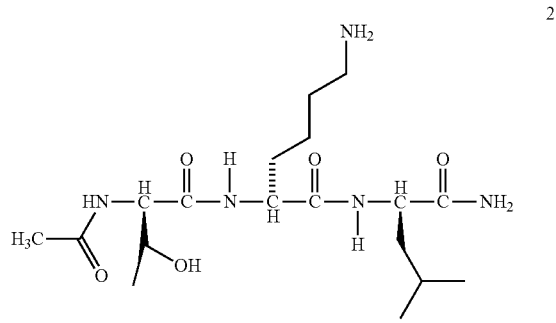

2

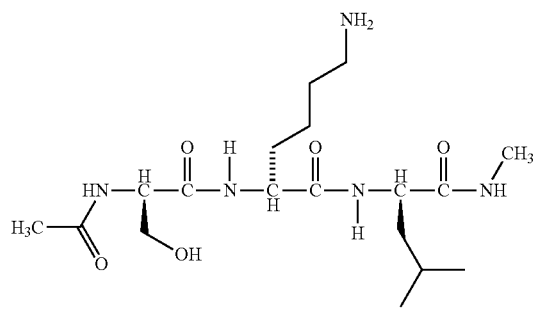

13

-continued

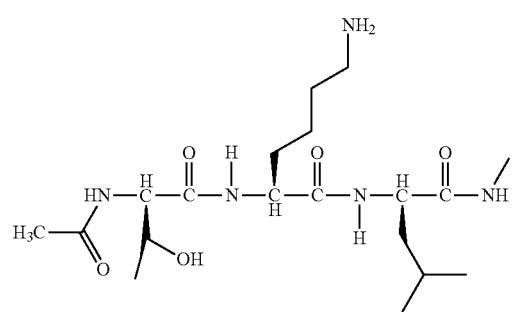

14

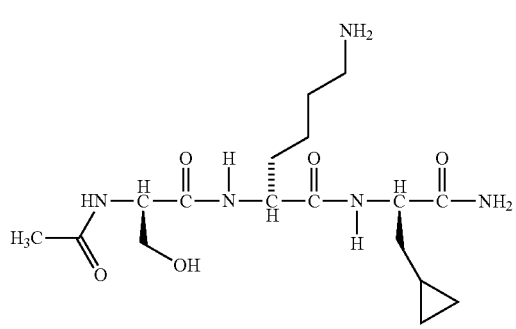

37

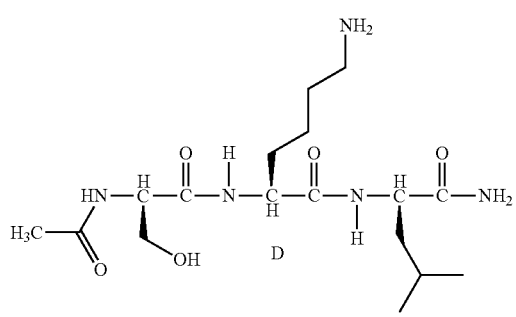

95

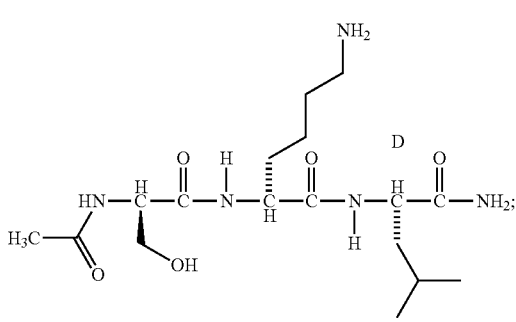

96 or a derivative thereof selected from the group consisting of pharmaceutically acceptable salts, prodrugs, deuterated forms, radio-actively labeled forms, stereo isomers, solvates and combinations thereof.

BRIEF DESCRIPTION OF THE DRAWINGS

FIG. 2 also shows the effect of combinations of Compound 1 with dexamethasone or bortezomib. Male SCID mice were injected via tail vein with 1.7 million human CAG-heparanase myeloma cells. Twelve days later treatments were started and continued for 24 days. Mice were treated with sterile saline or Compound 1 at a dose of 0.3 mg/kg/day delivered by osmotic pump. Other groups were treated with 1 mg/kg dexamethasone i.p. once per week or 1 mg/kg bortezomib 2×/week i.p. or Compound 1 in combination with dexamethasone or bortezomib.

DETAILED DESCRIPTION OF THE INVENTION

Figure 1:
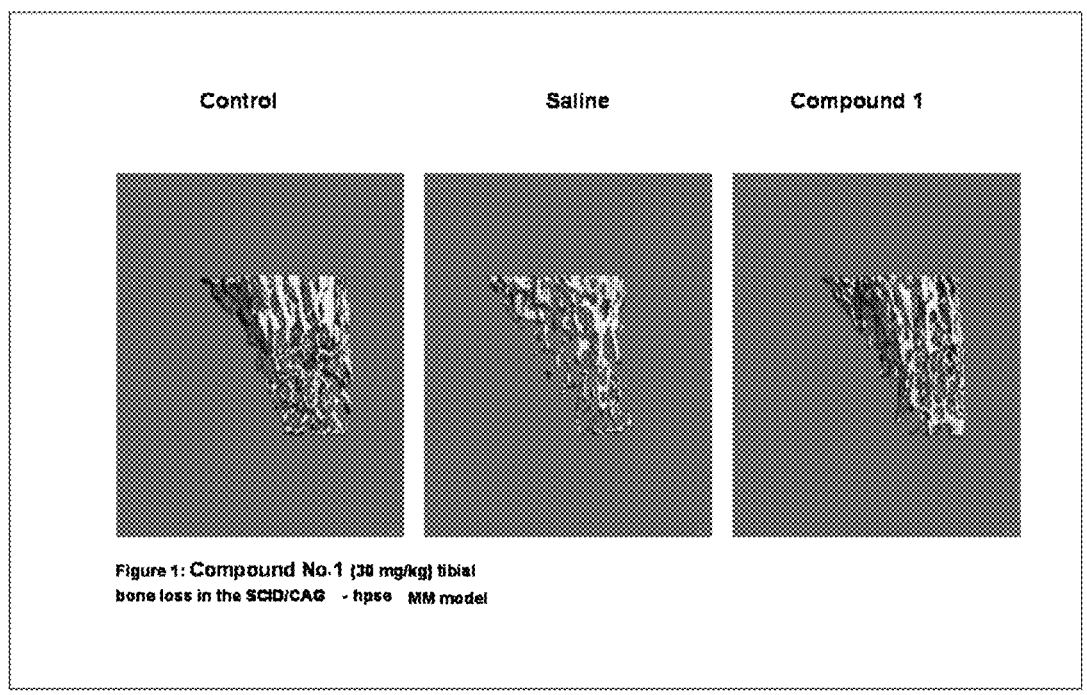
FIG. 1 shows effectiveness of Compound 1 at a 30 mg/kg dose in reducing tibial bone loss in the SCID/CAG-hpse MM model.
Figure 2:
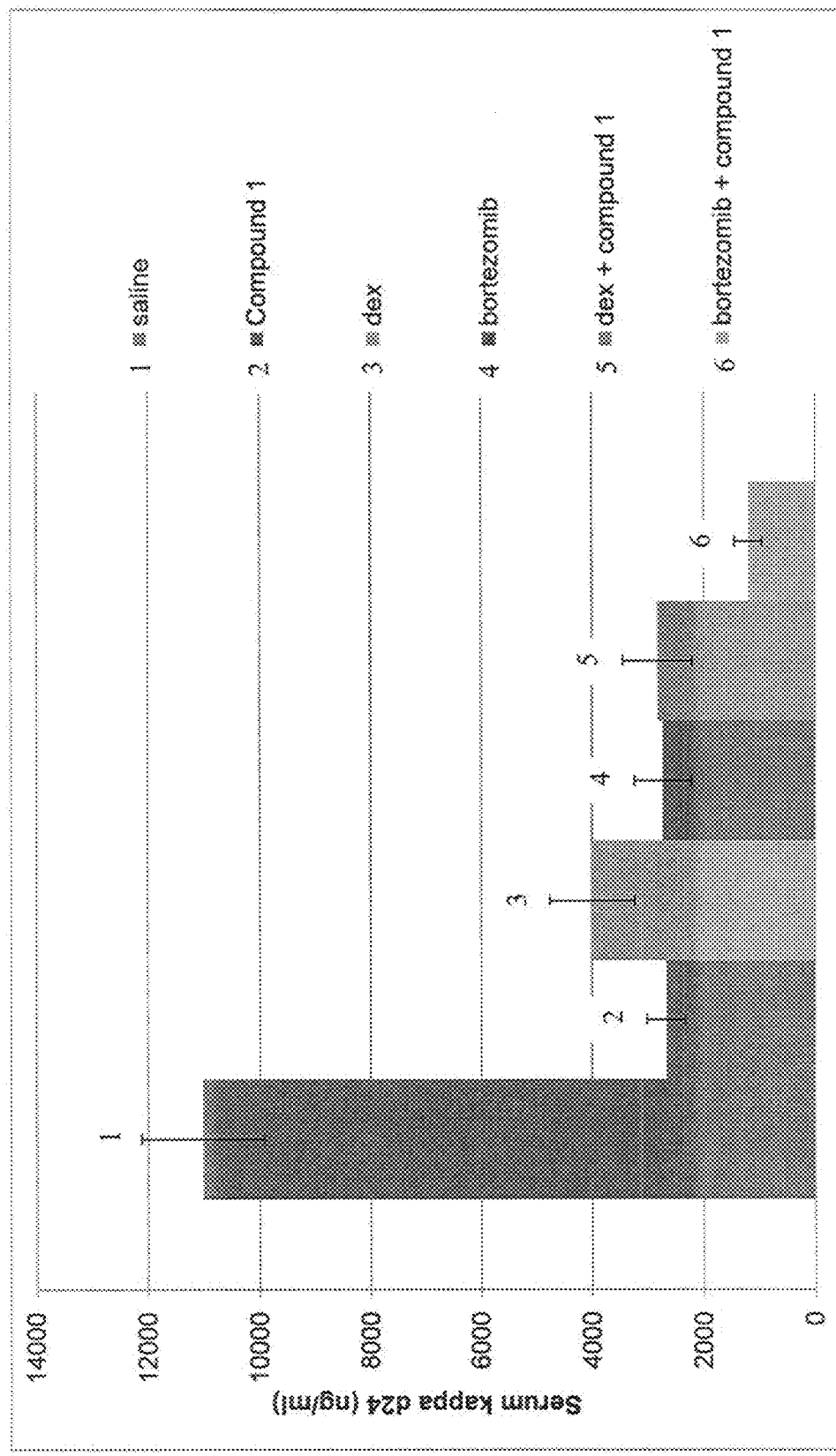
FIG. 2 is graph illustrating the effect of a compound according to the present disclosure (Compound 1) on male SCID mice injected with human CAG-heparanase myeloma cells as compared to sterile saline, dexamethasone and bortezomib, as measured by serum kappa d24 levels.

A detailed description of embodiments of the present invention is disclosed herein; however, it is to be understood that the disclosed embodiments are merely exemplary of the invention and that the invention may be embodied in various and alternative forms of the disclosed embodiments. Therefore, specific structural and functional details which are addressed in the embodiments disclosed herein are not to be interpreted as limiting, but merely as a basis for the claims and as a representative basis for teaching one skilled in the art to variously employ the present invention.

Unless specifically stated otherwise, all technical terms used herein have the meaning as commonly understood by those skilled in the art.

Alkyl as used herein specifies a saturated hydrocarbon radical of a general formula $C_nH_{2n+1}$ in which n is a positive integer. Correspondingly, $C_1$-$C_4$-alkyl represents alkyl groups in which n is an integer from 1 to 4 and $C_1$-$C_6$-alkyl represents alkyl groups in which n is an integer from 1 to 6. Those having ordinary skill in the art will appreciate that alkyl groups in which n is an integer of at least 3 may be straight-chained or branched. Illustrative examples of $C_1$-$C_4$-alkyl and $C_1$-$C_6$-alkyl groups include methyl, ethyl, n-propyl, iso-propyl, n-butyl, iso-butyl, sec-butyl, tert-butyl, n-pentyl, 1-methyl-butyl, 2-methyl-butyl, 3-methyl-butyl, 1,1-dimethyl-propyl, 1,2-dimethyl-propyl, 2,2-dimethyl-propyl, 1-ethyl-propyl, n-hexyl, 1-methyl-pentyl, 2-methyl-pentyl, 3-methyl-pentyl, 4-methyl-pentyl, 1,1-dimethyl-butyl, 1,2-dimethyl-butyl, 1,3-dimethyl-butyl, 2,3-dimethyl-butyl, 3,3-dimethyl-butyl, 1-ethyl-butyl, 2-ethyl-butyl, 1,1,2-trimethyl-propyl and 1,2,2-trimethyl-propyl.

Cycloalkyl as used herein specifies a saturated cyclic hydrocarbon radical of a general formula $C_nH_{2n-1}$ in which n is a positive integer of at least 3. Correspondingly, $C_3$-$C_6$-cycloalkyl represents cycloalkyl groups in which n is an integer from 3 to 6. Illustrative examples of $C_3$-$C_6$-cycloalkyl groups are cyclopropyl, cyclobutyl, cyclopentyl and cyclohexyl.

Aryl as used herein specifies monocyclic or polycyclic aromatic hydrocarbon radicals such as phenyl, naphtyl, biphenyl, anthracenyl, phenynthrenyl and the like.

Heterocyclyl as used herein specifies a saturated, partially unsaturated, or aromatic cyclic radical of at least 3 ring members having at least 2 carbon ring members and at least one ring member selected from the group of nitrogen, oxygen and sulfur. Those having ordinary skill in the art will appreciate that multiple oxygen and/or sulfur ring members are located in non-adjacent ring positions. The cyclic radicals are bonded via a carbon ring member in the absence of a nitrogen ring member. If one or more nitrogen ring members are present the radicals also may be bonded via one of those nitrogen ring members. Illustrative 5- and 6-membered heterocycles include 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 2-isoxazolidinyl, 3-isoxazolidinyl, 4-isoxazolidinyl, 5-isoxazolidinyl, 2-isothiazolidinyl, 3-isothiazolidinyl, 4-isothiazolidinyl, 5-isothiazolidinyl, 1(2)-pyrazolidinyl, 3-pyrazolidinyl, 4-pyrazolidinyl, 5-pyrazolidinyl, 2-oxazolidinyl, 3-oxazolidinyl, 4-oxazolidinyl, 5-oxazolidinyl, 2-thiazolidinyl, 3-thiazolidinyl, 4-thiazolidinyl, 5-thiazolidinyl, 1(3)-imidazolidinyl, 2-imidazolidinyl, 4-imidazolidinyl, 1,2,4-oxadiazolidin-1-yl, 1,2,4-oxadiazolidin-3-yl, 1,2,4-oxadiazolidin-5-yl, 1,3,4-oxadiazolidin-1-yl, 1,3,4-oxadiazolidin-2-yl, 1,2,4-thiadiazolidin-1-yl, 1,2,4-thiadiazolidin-3-yl, 1,2,4-thiadiazolidin-5-yl, 1,3,4-thiadiazolidin-1-yl, 1,3,4-thiadiazolidin-2-yl, 1,2,4-triazolidin-1-yl, 1,2,4-triazolidin-3-yl, 1,3,4-triazolidin-1-yl, 1,3,4-triazolidin-2-yl, 2,3-dihydrofuran-2-yl, 2,3-dihydrofuran-3-yl, 2,3-dihydrofuran-4-yl, 2,3-dihydrofuran-5-yl, 2,5-dihydrofuran-2-yl, 2,5-dihydrofuran-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-1-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-1-yl, 2,5-dihydropyrrol-2-yl, 2,5-dihydropyrrol-3-yl, 2,3-dihydroisoxazol-2-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisoxazol-2-yl, 2,5-dihydroisoxazol-3-yl, 2,5-dihydroisoxazol-4-yl, 2,5-dihydroxazol-5-yl, 2,3-dihydroisothiazol-2-yl, 2,3-dihydroisothiazol-3-yl, 2,3-dihydroisothiazol-4-yl, 2,3-dihydroisothiazol-5-yl, 4,5-dihydroisothiazol-3-yl, 4,5-dihydroisothiazol-4-yl, 4,5-dihydroisothiazol-5-yl, 2,5-dihydroisothiazol-2-yl, 2,5-dihydroisothiazol-3-yl, 2,5-dihydroisothiazol-4-yl, 2,5-dihydroisothiazol-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrothiazol-2-yl, 2,3-dihydrothiazol-3-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-1(3)-yl, 2,3-dihydroimidazol-2-yl, 2,3-dihydroimidazol-4-yl, 2,3-dihydroimidazol-5-yl, 4,5-dihydroimidazol-1(3)-yl, 4,5-dihydroimidazol-2-yl, 4,5-dihydroimidazol-4-yl, 4,5-dihydroimidazol-5-yl, 2,5-dihydroimidazol-1(3)-yl, 2,5-dihydroimidazol-2-yl, 2,5-dihydroimidazol-4-yl, 2,5-dihydroimidazol-5-yl, 2-morpholinyl, 3-morpholinyl, 4-morpholinyl, 1-piperidinyl, 2-piperidinyl, 3-piperidinyl, 4-piperidinyl, 1,2,3,4-tetrahydropyridazin-1-yl, 1,2,3,4-tetrahydropyridazin-2-yl, 1,2,3,4-tetrahydropyridazin-3-yl, 1,2,3,4-tetrahydropyridazin-4-yl, 1,2,3,4-tetrahydropyridazin-5-yl, 1,2,3,4-tetrahydropyridazin-6-yl, 1,2,3,4-tetrahydropyrimidin-1-yl, 1,2,3,4-tetrahydropyrimidin-2-yl, 1,2,3,4-tetrahydropyrimidin-3-yl, 1,2,3,4-tetrahydropyrimidin-4-yl, 1,2,3,4-tetrahydropyrimidin-5-yl, 1,2,3,4-tetrahydropyrimidin-6-yl, 1,2,3,4-tetrahydropyrazin-1-yl, 1,2,3,4-tetrahydropyrazin-2-yl, 1,2,3,4-tetrahydropyrazin-3-yl, 1,2,3,4-tetrahydropyrazin-4-yl, 1,2,3,4-tetrahydropyrazin-5-yl, 1,2,3,4-tetrahydropyrazin-6-yl, 1,2,3,4-tetrahydro-1,3,5-triazin-1-yl, 1,2,3,4-tetrahydro-1,3,5-triazin-2-yl, 1,2,3,4-tetrahydro-1,3,5-triazin-3-yl, 1,2,3,4-tetrahydro-1,3,5-triazin-4-yl, 1,2,3,4-tetrahydro-1,3,5-triazin-5-yl, 1,2,3,4-tetrahydro-1,3,5-triazin-6-yl, 1,2,3,4-tetrahydro-1,2,4-triazin-1-yl, 1,2,3,4-tetrahydro-1,2,4-triazin-2-yl, 1,2,3,4-tetrahydro-1,2,4-triazin-3-yl, 1,2,3,4-tetrahydro-1,2,4-triazin-4-yl, 1,2,3,4-tetrahydro-1,2,4-triazin-5-yl, 1,2,3,4-tetrahydro-1,2,4-triazin-6-yl, 1,3-dithian-2-yl, 2-tetrahydropyranyl, 3-tetrahydropyranyl, 4-tetrahydropyranyl, 2-tetrahydrothiopyranyl, 3-tetrahydrothiopyranyl, 4-tetrahydrothiopyranyl, 1,3-dioxolan-2-yl, 1,3-dioxolan-4-yl, 3,4,5,6-tetrahydropyridin-1-yl, 3,4,5,6-tetrahydropyridin-2-yl, 3,4,5,6-tetrahydropyridin-3-yl, 3,4,5,6-tetrahydropyridin-4-yl, 3,4,5,6-tetrahydropyridin-5-yl, 3,4,5,6-tetrahydropyridin-6-yl, 2,3-dihydro-1,4-thiazin-2-yl, 2,3-dihydro-1,4-thiazin-3-yl, 2,3-dihydro-1,4-thiazin-4-yl, 2,3-dihydro-1,4-thiazin-5-yl, 2,3-dihydro-1,4-thiazin-6-yl, 3,4-dihydro-1,3-oxazin-2-yl, 3,4-dihydro-1,3-oxazin-3-yl, 3,4-dihydro-1,3-oxazin-4-yl, 3,4-dihydro-1,3-oxazin-5-yl, 3,4-dihydro-1,3-oxazin-6-yl, 2,3-dihydro-1,4-oxazin-2-yl, 2,3-dihydro-1,4-oxazin-3-yl, 2,3-dihydro-1,4-oxazin-4-yl, 2,3-dihydro-1,4-oxazin-5-yl, 2,3-dihydro-1,4-oxazin-6-yl, 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 1,2,4-triazol-1-yl, 1,2,4-triazol-3-yl, 1,3,4-triazol-1-yl, 1,3,4-triazol-2-yl, tetrazol-5-yl, tetrazol-1-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,2,4-triazin-3-yl, 1,2,4-triazin-5-yl, 1,2,4-triazin-6-yl, 1,3,5-triazin-2-yl, 1,2,4,5-tetrazin-3-yl and the like.

The designation "optionally substituted" is used herein to indicate that the radical so characterized is unsubstituted or substituted, i.e., one or more of the hydrogen of such groups may be replaced by a corresponding number of radicals different from hydrogen.

Unless specifically indicated otherwise, the designation "optionally substituted" with regard to alkyl groups indicates that one or more of the hydrogen of such groups may be replaced by a corresponding number of radicals each independently selected from: halogen (i.e., fluoride, chloride, bromide and iodide), hydroxyl (OH), $C_1$-$C_6$-alkoxy (O—$C_1$-$C_6$-alkyl), amino ($NH_2$), $C_1$-$C_6$-alkylamino (NH($C_1$-$C_6$-alkyl)), di-($C_1$-$C_6$-alkyl)amino [N($C_1$-$C_6$-alkyl)$_2$ wherein the alkyl groups are identical or different], $C_1$-$C_6$-alkylcarbonylamino (NH—CO—$C_1$-$C_6$-alkyl), N—$C_1$-$C_6$-alkyl-N—$C_1$-$C_6$-alkylcarbonylamino [N(CO—$C_1$-$C_6$-alkyl)($C_1$-$C_6$-alkyl) wherein the alkyl groups are identical or different], $C_3$-$C_6$-cycloalkyl, $C_3$-$C_6$-cycloalkoxy (O—$C_3$-$C_6$-cycloalkyl), $C_3$-$C_6$-cycloalkylamino (NH—$C_3$-$C_6$-cycloalkyl), N—$C_1$-$C_6$-alkyl-N—$C_3$-$C_6$-cycloalkylamino (N($C_1$-$C_6$-alkyl)($C_3$-$C_6$-cycloalkyl)), N—$C_1$-$C_6$-alkylcarbonyl-N—$C_3$-$C_6$-cycloalkylamino [N(CO—$C_1$-$C_6$-alkyl)($C_3$-$C_6$-cycloalkyl)], di-($C_3$-$C_6$-cycloalkyl)amino [N($C_3$-$C_6$-cycloalkyl)$_2$ wherein the cycloalkyl groups are identical or different], aryl, aryloxy (O-aryl), arylamino (NH-aryl), N—$C_1$-$C_6$-alkyl-N-arylamino [N($C_1$-$C_6$-alkyl)(aryl)], N—$C_1$-$C_6$-alkylcarbonyl-N-arylamino [N(CO—$C_1$-$C_6$-alkyl)(aryl)], heterocyclyl, heterocyclyloxy (O-heterocyclyl), heterocyclylamino (NH-heterocyclyl), N—$C_1$-$C_6$-alkyl-N-heterocyclylamino [N($C_1$-$C_6$-alkyl)(heterocyclyl)], N—$C_1$-$C_6$-alkylcarbonyl-N-heterocyclylamino [N(CO—$C_1$-$C_6$-alkyl)(heterocyclyl)], and the like.

Unless specifically indicated otherwise, the designation "optionally substituted" with regard to cycloalkyl, aryl and heterocyclyl groups indicates that one or more of the hydrogen of such groups may be replaced by a corresponding number of radicals each independently selected from: halogen (i.e., fluoride, chloride, bromide and iodide), hydroxyl (OH), $C_1$-$C_6$-alkyl, $C_1$-$C_6$-alkoxy (O—$C_1$-$C_6$-alkyl), amino ($NH_2$), $C_1$-$C_6$-alkylamino (NH($C_1$-$C_6$-alkyl)), di-($C_1$-$C_6$-alkyl)amino [N($C_1$-$C_6$-alkyl)$_2$ wherein the alkyl groups are identical or different], $C_1$-$C_6$-alkylcarbonylamino (NH—CO—$C_1$-$C_6$-alkyl), N—$C_1$-$C_6$-alkyl-N—$C_1$-$C_6$-alkylcarbonylamino [N(CO—$C_1$-$C_6$-alkyl)($C_1$-$C_6$-alkyl) wherein the alkyl groups are identical or different], $C_3$-$C_6$-cycloalkyl, $C_3$-$C_6$-cycloalkoxy (O—$C_3$-$C_6$-cycloalkyl), $C_3$-$C_6$-cycloalkylamino (NH—$C_3$-$C_6$-cycloalkyl), N—$C_1$-$C_6$-alkyl-N—$C_3$-$C_6$-cycloalkylamino (N($C_1$-$C_6$-alkyl)($C_3$-$C_6$-cycloalkyl)), N—$C_1$-$C_6$-alkylcarbonyl-N—$C_3$-$C_6$-cycloalkylamino [N(CO—$C_1$-$C_6$-alkyl)($C_3$-$C_6$-cycloalkyl)], di-($C_3$-$C_6$-cycloalkyl)amino [N($C_3$-$C_6$-cycloalkyl)$_2$ wherein the cycloalkyl groups are identical or different], aryl, aryloxy (O-aryl), arylamino (NH-aryl), N—$C_1$-$C_6$-alkyl-N-arylamino [N($C_1$-$C_6$-alkyl)(aryl)], N—$C_1$-$C_6$-alkylcarbonyl-N-arylamino [N(CO—$C_1$-$C_6$-alkyl)(aryl)], heterocyclyl, heterocyclyloxy (O-heterocyclyl), heterocyclylamino (NH-heterocyclyl), N—$C_1$-$C_6$-alkyl-N-heterocyclylamino [N($C_1$-$C_6$-alkyl)(heterocyclyl)], N—$C_1$-$C_6$-alkylcarbonyl-N-heterocyclylamino [N(CO—$C_1$-$C_6$-alkyl)(heterocyclyl)], and the like.

The expression "pharmaceutically acceptable salts" as used herein refers to derivatives of the disclosed compounds wherein the parent compound is modified by making acid or base salts thereof. The compounds of this disclosure form acid addition salts with a wide variety of organic and inorganic acids and includes the physiologically acceptable salts which are often used in pharmaceutical chemistry. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkonic acids, hydroxyalkanoic and hydroxyalkandioic acids, aromatic acids, aliphatic and aromatic sulfonic acids may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like.

The expression "prodrugs" as used herein refers to derivatives of the disclosed compounds which are rapidly transformed in vivo to yield the parent compound represented by one of the formulae (I), (I.a), (II), (II.a), (III) and (III.a), for example, by hydrolysis in blood. The expression in particular includes compounds of formulae (I), (I.a), (II), (II.a), (III) and (III.a) in which hydroxyl or amino functionalities are modified using alkoxy, acyloxy, amino acids, mono- or polyphosphate, etc. groups as the prodrug forming moieties. For instance, a hydroxymethyl position may form mono-, di- or triphosphates and again these phosphates can act as prodrugs. The manufacture of such prodrugs is known in the art and is discussed in various literature sources (e.g., Alexander et al., J. Med. Chem. 1988, 31, 318; Aligas-Martin et al., US 2003/0212071, ¶134).

The expression "deuterated forms" as used herein refers to derivatives of the disclosed compounds in which one or more hydrogen are replaced by a corresponding number of deuterium ($^2H$).

The expression "radio-actively labeled forms" as used herein refers to derivatives of the disclosed compounds, including the salts and prodrugs thereof, in which at least one of the following replacements has been made:
  i) one or more hydrogen are replaced by a corresponding number of tritium ($^3H$).
  ii) one or more carbon-12 ($^{12}C$) are replaced by a corresponding number of carbon-11, carbon-13 ($^{13}C$), and/or carbon-14 ($^{14}C$);
  iii) one or more hydrogen and/or fluorine-19 ($^{19}F$) are replaced by a corresponding number of fluorine-18 ($^{18}F$);
  iv) one or more acidic hydrogen and/or sodium-23 ($^{23}Na$) are replaced by a corresponding number of sodium-22 ($^{22}Na$);
  v) one or more phosphorous-31 ($^{31}P$) are replaced by a corresponding number of phosphorous-32 ($^{32}P$);
  vi) one or more sulfur-32 ($^{32}S$) are replaced by a corresponding number of sulfur-35 ($^{35}S$);
  vii) one or more hydrogen and/or iodine-127 ($^{127}I$) are replaced by a corresponding number of iodine-125 ($^{125}I$) and/or iodine-131 ($^{131}I$).

Those having ordinary skill will appreciate that labeling introduced using fluorine, sodium, phosphorous, sulfur, or iodine atoms, can be achieved via selection of a suitable salt or prodrug form of the compound.

The expression "stereo isomers" as used herein refers to compounds represented by the same two-dimensional structural formula, i.e., having the same constitution, but differing in their three-dimensional orientation. Unless specifically indicated otherwise, the two-dimensional structural formulae shown herein are intended to represent all optical isomers and stereo-isomers at the various asymmetrically substituted atoms of the molecule, i.e., all enantiomeric forms and diastereomeric forms of the compounds. Those having ordinary skill will appreciate that such enantiomeric or diastereomeric forms of the compounds disclosed herein may be prepared as such, or may be obtained by separating stereo isomer mixtures using crystallization, chromatography, or the like.

The expression "solvates" as used herein refers to adducts of the compound formed by the interaction with a solvent. Solvates are usually crystalline solid adducts containing solvent molecules within the crystal structure, in either stoichiometric or nonstoichiometric proportions. Those having ordinary skill in the art will appreciate that solvates include hydrates.

The derivatives of the compounds of the present disclosure in particular also include combinations of the modifications and particular forms addressed hereinabove. That is, the compound may be in form of its pharmaceutically acceptable salt, and/or in form of a prodrug, and/or in deuterated form, and/or in radio-actively labeled form, and/or in form of one or more specific optical isomers, and/or in form of a solvate.

The expression "compound (A)" and the plural thereof as used herein collectively refers to compounds of formulae (I), (I.a), (II), (II.a), (III), and (III.a), and the derivatives thereof. Thus, unless specifically indicated otherwise, the description of a particular embodiment of compound (A) is to be understood as a description of the corresponding particular embodiments of the compounds of formulae (I), (I.a), (II), (II.a), (III), and (III.a), and the derivatives thereof, to the extent the embodiment falls within the realm of the respective formula and derivatives as outlined above. For example, the description of particular embodiments of compounds (A) in which $Y^1$ denotes hydrogen or methyl means that each of the compounds of formulae (I), (I.a), (II), (II.a), (III), and (III.a), and each of the derivatives thereof, in which $Y^1$ denotes hydrogen or methyl, constitutes a particular embodiment.

The expression "compound (A')" and the plural thereof as used herein collectively refers to compounds of formulae (I), (I.a), (II), (II.a), (III), and (III.a). Thus, unless specifically indicated otherwise, the description of a particular embodiment of compound (A') is to be understood as a description of the corresponding particular embodiments of the compounds of formulae (I), (I.a), (II), (II.a), (III), and (III.a), to the extent the embodiment falls within the realm of the respective formula as outlined above. For example, the description of particular embodiments of compounds (A') in which $Y^1$ denotes hydrogen or methyl means that each of the compounds of formulae (I), (I.a), (II), (II.a), (III), and (III.a), in which $Y^1$ denotes hydrogen or methyl, constitutes a particular embodiment.

The term "comprising" (and its grammatical variations) as used herein is used in the inclusive sense of "having" or "including" and not in the exclusive sense of "consisting of." The terms "a" and "the" as used herein are understood to encompass the plural as well as the singular.

All documents (patent literature and non-patent literature) cited in this specification are herein incorporated by reference, and for any and all purposes, as if each individual document was specifically and individually indicated to be incorporated by reference. In the event of an inconsistency between the present disclosure and any one of the documents incorporated herein by reference, the present disclosure controls.

$Y^1$ of the compounds (A) generally represents hydrogen, $C_1$-$C_4$-alkyl which is optionally substituted by $C_3$-$C_6$-cycloalkyl or aryl, or represents $C_3$-$C_6$-cycloalkyl. Additionally, when the compound (A) is a prodrug, $Y^1$ may be a prodrug-forming moiety.

In some of the embodiments of the compounds (A) disclosed herein, $Y^1$ represents hydrogen, $C_1$-$C_3$-alkyl, cyclopropyl-$C_1$-$C_2$-alkyl, phenyl-$C_1$-$C_2$-alkyl, cyclopropyl, cyclopentyl, or cyclohexyl.

In other embodiments of the compounds (A), $Y^1$ of the compounds represents hydrogen or $C_1$-$C_3$-alkyl, or represents hydrogen, methyl or ethyl.

In particular embodiments of the compounds (A), $Y^1$ of the compounds represents hydrogen or methyl.

$Y^2$ of the compounds (A) generally represents hydrogen, $C_1$-$C_4$-alkyl which is optionally substituted by $C_3$-$C_6$-cycloalkyl or aryl, or represents $C_3$-$C_6$-cycloalkyl or $COR^a$ with $R^a$ being hydrogen, $C_1$-$C_4$-alkyl, $C_3$-$C_6$-cycloalkyl, or optionally substituted aryl. Additionally, when the compound (A) is a prodrug, $Y^2$ may be a prodrug-forming moiety.

In some of the embodiments of the compounds (A) disclosed herein, $Y^2$ represents hydrogen, $C_1$-$C_3$-alkyl, cyclopropyl-$C_1$-$C_2$-alkyl, phenyl-$C_1$-$C_2$-alkyl, cyclopropyl, cyclopentyl, cyclohexyl.

In other embodiments of the compounds (A), $Y^2$ of the compounds represents hydrogen or $C_1$-$C_3$-alkyl, or represents hydrogen, methyl or ethyl.

In particular embodiments of the compounds (A), $Y^2$ of the compounds represents hydrogen or methyl.

In alternative embodiments of the compounds (A) disclosed herein, $Y^2$ represents $C_1$-$C_4$-alkyl, or $COR^a$.

In particular alternative embodiments, $Y^2$ of the compounds (A) represents $C_1$-$C_3$-alkyl, or represents methyl, ethyl, or $COR^a$.

In the foregoing embodiments of the compounds (A) in which $Y^2$ represents $COR^a$ the radical $R^a$ particularly represents, $C_1$-$C_4$-alkyl, cyclopropyl, cyclopentyl, cyclohexyl, or optionally substituted phenyl. Among these embodiments, the optional substituents of the phenyl group particularly include 1-5 halogen (e.g., fluoride, chloride, bromide and iodide), and/or 1-3 substituents independently selected from the group of: $C_1$-$C_4$-alkyl (e.g., methyl, ethyl, iso-propyl, tert-butyl), $C_1$-$C_4$-alkoxy (e.g., methoxy, ethoxy, iso-propyloxy, tert-butyloxy), amino, $C_1$-$C_4$-alkylamino (e.g., methylamino, ethylamino, iso-propylamino, tert-butylamino), and di-($C_1$-$C_4$-alkyl)amino (e.g., N,N-dimethylamino, N-ethyl-N-methylamino, N,N-diethylamino, N-iso-propyl-N-methylamino, N-ethyl-N-isopropylamino, N,N-di(iso-propyl)amino, N,N-di(tert-butyl)amino, N-methyl-N-tert-butylamino, N-ethyl-N-tert-butylamino, and the like).

In further embodiments, $Y^2$ of the compounds (A) represents $COR^a$. In some of the particular aspects of these embodiments the radical $R^a$ represents $C_1$-$C_4$-alkyl, cyclopentyl, cyclohexyl, or optionally substituted phenyl. In embodiments in which $R^a$ denotes a substituted phenyl, the substituents of the phenyl group particularly include 1-5 halogen (e.g., fluoride, chloride, bromide and iodide), and/or 1-3 substituents independently selected from the group of: $C_1$-$C_2$-alkyl, $C_1$-$C_2$-alkoxy, amino, $C_1$-$C_2$-alkylamino, and di-($C_1$-$C_2$-alkyl)amino as mentioned in general and in particular herein above.

In particular embodiments of the compounds (A) in which $Y^2$ represents $COR^a$ and the radical $R^a$ represents $C_1$-$C_4$-alkyl, or optionally substituted phenyl. Among these embodiments, the optional substituents of the phenyl group particularly include 1-3 substituents independently selected from the group of: halogen (fluoride, chloride, bromide and iodide), $C_1$-$C_4$-alkyl and $C_1$-$C_4$-alkoxy. In a particular aspect of these embodiments, $Y^2$ represents $COR^a$ and the radical $R^a$ represents $C_1$-$C_4$-alkyl.

$R^1$ of the compounds (A) generally represents hydrogen, $C_1$-$C_6$-alkyl, $C_1$-$C_4$-alkyl which is substituted by hydroxyl or $OR^b$, or represents optionally substituted $C_3$-$C_6$-cycloalkyl or optionally substituted 5- or 6-membered heterocyclyl, with $R^b$ being $C_1$-$C_6$-alkyl, $C_3$-$C_6$-cycloalkyl, or optionally substituted 5- or 6-membered heterocyclyl. Additionally, when the compound (A) is a prodrug, $R^b$ may be a prodrug forming moiety.

In some of the embodiments of the compounds (A) disclosed herein, $R^1$ represents hydrogen, $C_1$-$C_6$-alkyl or optionally substituted $C_3$-$C_6$-cycloalkyl. In particular embodiments, $R^1$ represents hydrogen, $C_1$-$C_4$-alkyl or an optionally substituted cyclopropyl, cyclopentyl or cyclohexyl group. When $R^1$ represents an optionally substituted cycloalkyl group, the optional substituents particularly include 1-5 halogen, and/or 1-3 substituents independently selected from the group of: $C_1$-$C_4$-alkyl, hydroxyl, $C_1$-$C_4$-alkoxy, amino, $C_1$-$C_4$-alkylamino, and di-($C_1$-$C_4$-alkyl)amino as mentioned in general and in particular herein above. In alternative embodiments, the optional substituents of the cycloalkyl group include, in particular, 1-3 substituents independently selected from the group of: halogen (fluoride and chloride), $C_1$-$C_4$-alkyl, hydroxyl and $C_1$-$C_4$-alkoxy.

In further embodiments of the compounds (A) disclosed herein, $R^1$ represents optionally substituted $C_3$-$C_6$-cycloalkyl as mentioned in general and in particular hereinabove, or represents an optionally substituted 5- or 6-membered heterocycle. When $R^1$ represents an optionally substituted heterocycle, the optional substituents particularly include 1-5 halogen, and/or 1-3 substituents independently selected from the group of: $C_1$-$C_4$-alkyl, hydroxyl, $C_1$-$C_4$-alkoxy, amino, $C_1$-$C_4$-alkylamino, and di-($C_1$-$C_4$-alkyl)amino as mentioned in general and in particular herein above. In alternative embodiments, the optional substituents of the cycloalkyl group include, in particular, 1-3 substituents independently selected from the group of: halogen (fluoride and chloride), $C_1$-$C_4$-alkyl, hydroxyl and $C_1$-$C_4$-alkoxy.

The heterocyclic moieties of the optionally substituted 5- or 6-membered heterocycle represented by $R^1$ particularly are saturated or partially unsaturated, non-aromatic rings formed by 3-5 carbon ring members and one or two heteroatoms selected from the group of two nitrogen atoms and one oxygen atom. Illustrative ring structures include in particular 2-tetrahydrofuranyl, 3-tetrahydrofuranyl, 1-pyrrolidinyl, 2-pyrrolidinyl, 3-pyrrolidinyl, 2-isoxazolidinyl, 3-isoxazolidinyl, 4-isoxazolidinyl, 5-isoxazolidinyl, 1(2)-pyrazolidinyl, 3-pyrazolidinyl, 4-pyrazolidinyl, 5-pyrazolidinyl, 2-oxazolidinyl, 3-oxazolidinyl, 4-oxazolidinyl, 5-oxazolidinyl, 1(3)-imidazolidinyl, 2-imidazolidinyl, 4-imidazolidinyl, 2,3-dihydrofuran-2-yl, 2,3-dihydrofuran-3-yl, 2,3-dihydrofuran-4-yl, 2,3-dihydrofuran-5-yl, 2,5-dihydrofuran-2-yl, 2,5-dihydrofuran-3-yl, 2,3-dihydropyrrol-1-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-1-yl, 2,5-dihydropyrrol-2-yl, 2,5-dihydropyrrol-3-yl, 2,3-dihydroisoxazol-2-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisoxazol-2-yl, 2,5-dihydroisoxazol-3-yl, 2,5-dihydroisoxazol-4-yl, 2,5-dihydroxazol-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydroimidazol-1(3)-yl, 2,3-dihydroimidazol-2-yl, 2,3-dihydroimidazol-4-yl, 2,3-dihydroimidazol-5-yl, 4,5-dihydroimidazol-1(3)-yl, 4,5-dihydroimidazol-2-yl, 4,5-dihydroimidazol-4-yl, 4,5-dihydroimidazol-5-yl, 2,5-dihydroimidazol-1(3)-yl, 2,5-dihydroimidazol-2-yl, 2,5-dihydroimidazol-4-yl, 2,5-dihydroimidazol-5-yl, 2-morpholinyl, 3-morpholinyl, 4-morpholinyl, 1-piperidinyl, 2-piperidinyl, 3-piperidinyl, 4-piperidinyl, 1,2,3,4-tetrahydropyridazin-1-yl, 1,2,3,4-tetrahydropyridazin-2-yl, 1,2,3,4-tetrahydropyridazin-3-yl, 1,2,3,4-tetrahydropyridazin-4-yl, 1,2,3,4-tetrahydropyridazin-5-yl, 1,2,3,4-tetrahydropyridazin-6-yl, 1,2,3,4-tetrahydropyrimidin-1-yl, 1,2,3,4-tetrahydropyrimidin-2-yl, 1,2,3,4-tetrahydropyrimidin-3-yl, 1,2,3,4-tetrahydropyrimidin-4-yl, 1,2,3,4-tetrahydropyrimidin-5-yl, 1,2,3,4-tetrahydropyrimidin-6-yl, 1,2,3,4-tetrahydropyrazin-1-yl, 1,2,3,4-tetrahydropyrazin-2-yl, 1,2,3,4-tetrahydropyrazin-3-yl, 1,2,3,4-tetrahydropyrazin-4-yl, 1,2,3,4-tetrahydropyrazin-5-yl, 1,2,3,4-tetrahydropyrazin-6-yl, 2-tetrahydropyranyl, 3-tetrahydropyranyl, 4-tetrahydropyranyl, 2-tetrahydrothiopyranyl, 3-tetrahydrothiopyranyl, 4-tetrahydrothiopyranyl, 1,3-dioxolan-2-yl, 1,3-dioxolan-4-yl, 3,4,5,6-tetrahydropyridin-1-yl, 3,4,5,6-tetrahydropyridin-2-yl, 3,4,5,6-tetrahydropyridin-3-yl, 3,4,5,6-tetrahydropyridin-4-yl, 3,4,5,6-tetrahydropyridin-5-yl, 3,4,5,6-tetrahydropyridin-6-yl, 3,4-dihydro-1,3-oxazin-2-yl, 3,4-dihydro-1,3-oxazin-3-yl, 3,4-dihydro-1,3-oxazin-4-yl, 3,4-dihydro-1,3-oxazin-5-yl, 3,4-dihydro-1,3-oxazin-6-yl, 2,3-dihydro-1,4-oxazin-2-yl, 2,3-dihydro-1,4-oxazin-3-yl, 2,3-dihydro-1,4-oxazin-4-yl, 2,3-dihydro-1,4-oxazin-5-yl, 2,3-dihydro-1,4-oxazin-6-yl, and the like.

In particular embodiments, the heterocyclic moieties of $R^1$ are saturated rings formed by 3-5 carbon ring members, one or two nitrogen ring members, and optionally one oxygen ring member.

In further particular embodiments disclosed herein, $R^1$ of the compounds (A) represents $C_3$-$C_6$-cycloalkyl or $C_1$-$C_4$-alkyl each of which is substituted by hydroxyl or $OR^b$ with $R^b$ being $C_1$-$C_6$-alkyl, $C_3$-$C_6$-cycloalkyl, or optionally substituted 5- or 6-membered heterocyclyl as mentioned in general and in particular hereinabove. In these embodiments, a cycloalkyl group in the position of $R^1$ is substituted by at least one hydroxyl or $OR^b$ group and may further be substituted by one or more $C_1$-$C_4$-alkyl groups. In one aspect of these embodiments, $R^1$ represents methyl, ethyl, propyl, butyl, isobutyl, cyclopentyl or cyclohexyl, in each case at least substituted by one hydroxyl or $OR^b$ radical and $R^b$ is $C_1$-$C_4$-alkyl, cyclopentyl or cyclohexyl. In another aspect of these embodiments, $R^1$ represents methyl, ethyl, propyl, butyl, isobutyl, cyclopentyl or cyclohexyl, in each case at least substituted by one hydroxyl and optionally 1-2 $OR^b$ radicals. In a further aspect of these embodiments, the alkyl and cycloalkyl moieties of $R^1$ are substituted by one hydroxyl group.

In yet further embodiments, $R^1$ of the compounds (A) represents $C_1$-$C_4$-alkyl which is substituted by hydroxyl. In a particular aspect of these embodiments, the alkyl group is straight-chained or is branched once. Illustrative alkyl structures include methyl, ethyl, propyl, iso-propyl, butyl, iso-butyl and sec-butyl. In a further particular aspect of these embodiments, the hydroxyl substituent is bonded to the alkyl carbon which links $R^1$ to the remainder of the formula, or is bonded to the adjacent alkyl carbon. Illustrative hydroxyl substituted alkyl structures of this aspect include hydroxyl-methyl, 1-hydroxy-ethyl, 1-hydroxy-propyl, 2-hydroxy-propyl, 1-hydroxy-1-methylethyl, 2-hydroxy-1-methylethyl, 1-hydroxy-butyl, 2-hydroxy-butyl, 1-hydroxy-1-methylpropyl, 2-hydroxy-1-methylpropyl, 1-hydroxy-2-methylpropyl and 2-hydroxy-2-methylpropyl. In another particular aspect of these embodiments, the hydroxyl substituent is bonded to the alkyl carbon which links $R^1$ to the remainder of the formula. Illustrative hydroxyl substituted alkyl structures of this aspect include hydroxyl-methyl, 1-hydroxy-ethyl, 1-hydroxy-propyl, 1-hydroxy-1-methylethyl, 1-hydroxy-butyl, 1-hydroxy-1-methylpropyl and 1-hydroxy-2-methylpropyl.

$R^2$ of the compounds (A) generally represents $C_1$-$C_6$-alkyl which is substituted by 5- or 6-membered heterocyclyl or $NR^cR^d$; or represents $C_3$-$C_6$-cycloalkyl which is optionally substituted by $C_1$-$C_4$-alkyl, 5- or 6-membered heterocyclyl or $NR^cR^d$; with $R^c$ being hydrogen or $C_1$-$C_4$-alkyl; and $R^d$ being hydrogen, $C_1$-$C_4$-alkyl or $C_3$-$C_6$-cycloalkyl; or with $R^c$ and $R^d$ together with the nitrogen to which they are bonded forming an optionally substituted 5- or 6-membered heterocycle. Additionally, when the compound (A) is a prodrug, $R^c$ and/or $R^d$ may be a prodrug forming moiety.

In some embodiments of the compounds (A) $R^2$ is a $C_1$-$C_6$-alkyl which is optionally substituted by 5- or 6-membered heterocyclyl or $NR^cR^d$. In a particular aspect of these embodiments, the alkyl group is substituted and the respective substituent is linked to a terminal carbon atom, or adjacent to a terminal carbon, of the alkyl group. In a further particular aspect of these embodiments, alkyl groups in the position of $R^2$ are straight-chained or include at most 2, preferably at most 1, branching position.

The 5- or 6-membered heterocyclyl substituents of the alkyl groups generally consist of carbon ring members and at least one hetero atom ring member selected from the group of nitrogen, oxygen and sulfur. The heterocycles may be saturated, partially unsaturated or aromatic, and may be bonded to the alkyl group via a carbon or nitrogen ring member.

In some particular embodiments, the heterocycles are saturated or partially unsaturated, non-aromatic rings formed by 3-5 carbon ring members and one or two heteroatoms selected from the group of two nitrogen atoms and one oxygen atom. Illustrative ring structures include in particular 2-tetrahydrofuranyl, 3-tetrahydrofuranyl, 1-pyrrolidinyl, 2-pyrrolidinyl, 3-pyrrolidinyl, 2-isoxazolidinyl, 3-isoxazolidinyl, 4-isoxazolidinyl, 5-isoxazolidinyl, 1(2)-pyrazolidinyl, 3-pyrazolidinyl, 4-pyrazolidinyl, 5-pyrazolidinyl, 2-oxazolidinyl, 3-oxazolidinyl, 4-oxazolidinyl, 5-oxazolidinyl, 1(3)-imidazolidinyl, 2-imidazolidinyl, 4-imidazolidinyl, 2,3-dihydrofuran-2-yl, 2,3-dihydrofuran-3-yl, 2,3-dihydrofuran-4-yl, 2,3-dihydrofuran-5-yl, 2,5-dihydrofuran-2-yl, 2,5-dihydrofuran-3-yl, 2,3-dihydropyrrol-1-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-1-yl, 2,5-dihydropyrrol-2-yl, 2,5-dihydropyrrol-3-yl, 2,3-dihydroisoxazol-2-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisoxazol-2-yl, 2,5-dihydroisoxazol-3-yl, 2,5-dihydroisoxazol-4-yl, 2,5-dihydroxazol-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydroimidazol-1(3)-yl, 2,3-dihydroimidazol-2-yl, 2,3-dihydroimidazol-4-yl, 2,3-dihydroimidazol-5-yl, 4,5-dihydroimidazol-1(3)-yl, 4,5-dihydroimidazol-2-yl, 4,5-dihydroimidazol-4-yl, 4,5-dihydroimidazol-5-yl, 2,5-dihydroimidazol-1(3)-yl, 2,5-dihydroimidazol-2-yl, 2,5-dihydroimidazol-4-yl, 2,5-dihydroimidazol-5-yl, 2-morpholinyl, 3-morpholinyl, 4-morpholinyl, 1-piperidinyl, 2-piperidinyl, 3-piperidinyl, 4-piperidinyl, 1,2,3,4-tetrahydropyridazin-1-yl, 1,2,3,4-tetrahydropyridazin-2-yl, 1,2,3,4-tetrahydropyridazin-3-yl, 1,2,3,4-tetrahydropyridazin-4-yl, 1,2,3,4-tetrahydropyridazin-5-yl, 1,2,3,4-tetrahydropyridazin-6-yl, 1,2,3,4-tetrahydropyrimidin-1-yl, 1,2,3,4-tetrahydropyrimidin-2-yl, 1,2,3,4-tetrahydropyrimidin-3-yl, 1,2,3,4-tetrahydropyrimidin-4-yl, 1,2,3,4-tetrahydropyrimidin-5-yl, 1,2,3,4-tetrahydropyrimidin-6-yl, 1,2,3,4-tetrahydropyrazin-1-yl, 1,2,3,4-tetrahydropyrazin-2-yl, 1,2,3,4-tetrahydropyrazin-3-yl, 1,2,3,4-tetrahydropyrazin-4-yl, 1,2,3,4-tetrahydropyrazin-5-yl, 1,2,3,4-tetrahydropyrazin-6-yl, 2-tetrahydropyranyl, 3-tetrahydropyranyl, 4-tetrahydropyranyl, 2-tetrahydrothiopyranyl, 3-tetrahydrothiopyranyl, 4-tetrahydrothiopyranyl, 1,3-dioxolan-2-yl, 1,3-dioxolan-4-yl, 3,4,5,6-tetrahydropyridin-1-yl, 3,4,5,6-tetrahydropyridin-2-yl, 3,4,5,6-tetrahydropyridin-3-yl, 3,4,5,6-tetrahydropyridin-4-yl, 3,4,5,6-tetrahydropyridin-5-yl, 3,4,5,6-tetrahydropyridin-6-yl, 3,4-dihydro-1,3-oxazin-2-yl, 3,4-dihydro-1,3-oxazin-3-yl, 3,4-dihydro-1,3-oxazin-4-yl, 3,4-dihydro-1,3-oxazin-5-yl, 3,4-dihydro-1,3-oxazin-6-yl, 2,3-dihydro-1,4-oxazin-2-yl, 2,3-dihydro-1,4-oxazin-3-yl, 2,3-dihydro-1,4-oxazin-4-yl, 2,3-dihydro-1,4-oxazin-5-yl, 2,3-dihydro-1,4-oxazin-6-yl, and the like.

In other particular embodiments, the heterocycles are aromatic rings formed by 2-5 carbon ring members, at least one nitrogen ring member and, in the case of 5-membered heterocycles, optionally one oxygen ring member. Illustrative ring structures include in particular 1-pyrrolyl, 2-pyrrolyl, 3-pyrrolyl, 3-isoxazolyl, 4-isoxazolyl, 5-isoxazolyl, 1-pyrazolyl, 3-pyrazolyl, 4-pyrazolyl, 5-pyrazolyl, 2-oxazolyl, 4-oxazolyl, 5-oxazolyl, 1-imidazolyl, 2-imidazolyl, 4-imidazolyl, 1,2,4-oxadiazol-3-yl, 1,2,4-oxadiazol-5-yl, 1,3,4-oxadiazol-2-yl, 1,2,4-triazol-1-yl, 1,2,4-triazol-3-yl, 1,3,4-triazol-1-yl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,2,4-triazin-3-yl, 1,2,4-triazin-5-yl, 1,2,4-triazin-6-yl, 1,3,5-triazin-2-yl, and the like.

The radical $R^c$ of the $NR^cR^d$ substituents generally is hydrogen or $C_1$-$C_4$-alkyl. In some of the particular embodiments of the compounds (A), $R^c$ is hydrogen, methyl or ethyl, or is hydrogen or methyl. Additionally, when the compound (A) is a prodrug, one or both of $R^c$ and $R^d$ may be a prodrug forming moiety.

The radical $R^d$ of the $NR^cR^d$ substituents generally is hydrogen, $C_1$-$C_4$-alkyl $C_3$-$C_6$-cycloalkyl or C(=O)$C_1$-$C_4$-alkyl. In some of the particular embodiments of the compounds (A), $R^d$ is hydrogen, methyl or ethyl, or is hydrogen or methyl. In other particular embodiments, $R^d$ is $C_1$-$C_4$-alkyl $C_3$-$C_6$-cycloalkyl or C(=O)$C_1$-$C_4$-alkyl, or is methyl, ethyl, iso-propyl, cyclopropyl, cyclophenyl, cyclohexyl or C(=O) $CH_3$.

In further embodiments, the $NR^cR^d$ substituent represents an optionally substituted 5- or 6-membered heterocycle which is bonded to the alkyl group via the nitrogen.

In some embodiments, the heterocycles formed by $NR^cR^d$ are saturated or partially unsaturated, non-aromatic rings formed by the nitrogen atom to which $R^c$ and $R^d$ are bonded, 3-5 carbon ring members and, optionally, one or two further heteroatoms selected from the group of nitrogen and oxygen. Illustrative ring structures include in particular 1-pyrrolidinyl, 2-isoxazolidinyl, 1(2)-pyrazolidinyl, 3-oxazolidinyl, 4-oxazolidinyl, 5-oxazolidinyl, 1(3)-imidazolidinyl, 2,3-dihydropyrrol-1-yl, 2,5-dihydropyrrol-1-yl, 2,3-dihydroisoxazol-2-yl, 2,5-dihydroisoxazol-2-yl, 2,3-dihydropyrazol-1-yl, 2,3-dihydropyrazol-2-yl, 4,5-dihydropyrazol-1-yl, 2,3-dihydrooxazol-3-yl, 2,3-dihydroimidazol-1(3)-yl, 4,5-dihydroimidazol-1(3)-yl, 2,5-dihydroimidazol-1(3)-yl, 4-morpholinyl, 1-piperidinyl, 1,2,3,4-tetrahydropyridazin-1-yl, 1,2,3,4-tetrahydropyridazin-2-yl, 1,2,3,4-tetrahydropyrimidin-1-yl, 1,2,3,4-tetrahydropyrimidin-3-yl, 1,2,3,4-tetrahydropyrazin-1(4)-yl, 3,4,5,6-tetrahydropyridin-1-yl, 3,4-dihydro-1,3-oxazin-3-yl, 2,3-dihydro-1,4-oxazin-3-yl, and the like.

In other embodiments, the heterocycles formed by $NR^cR^d$ are aromatic 5-membered rings formed by the nitrogen atom to which $R^c$ and $R^d$ are bonded, 2-4 carbon ring members and optionally one or two further nitrogen ring members. Illustrative structures include in particular 1-pyrrolyl, 1-pyrazolyl, 1-imidazolyl, 1,2,3-triazol-1-yl and 1,2,4-triazol-1-yl.

The 5- or 6-membered heterocyclyl substituents of the alkyl groups, as well as the heterocycles formed by the $NR^cR^d$ substituents, are optionally substituted. The optional substituents particularly include 1-5 halogen, and/or 1-3 substituents independently selected from the group of: $C_1$-$C_4$-alkyl, hydroxyl, $C_1$-$C_4$-alkoxy, amino, $C_1$-$C_4$-alkylamino, and di- ($C_1$-$C_4$-alkyl)amino as mentioned in general and in particular herein above. In alternative embodiments, the optional substituents of the heterocyclyl group include, in particular, 1-3 substituents independently selected from the group of: halogen (fluoride and chloride), $C_1$-$C_4$-alkyl, hydroxyl and $C_1$-$C_4$-alkoxy.

In further embodiments, $R^2$ of the compounds (A) is a $C_3$-$C_6$-cycloalkyl which is optionally substituted by $C_1$-$C_4$-alkyl, 5- or 6-membered heterocyclyl or $NR^cR^d$. In one particular aspect of these embodiments, the cycloalkyl group is substituted. In another particular aspect of these embodiments, the cycloylkyl group is substituted by 5- or 6-membered heterocyclyl or $NR^cR^d$, and further is optionally substituted by 1-3 $C_1$-$C_4$-alkyl groups. Such optional alkyl groups are in particular methyl and/or ethyl groups and may be bonded to any position of the cycloalkyl ring. The 5- or 6-membered heterocyclyl or $NR^cR^d$ substituents of the cycloalkyl group are preferably bonded to a ring position which is removed from the carbon ring member which links $R^2$ to the remainder of the formula by at least one carbon ring member of the cycloylkyl moiety. For example, in embodiments in which the cycloylkyl moiety is cyclopentyl, the 5- or 6-membered heterocyclyl substituent or the $NR^cR^d$ substituent is bonded in 2- or 3-position. Correspondingly, in embodiments in which the cycloylkyl moiety is cyclohexyl, the 5- or 6-membered heterocyclyl substituent or the $NR^cR^d$ substituent is bonded in 2-, 3- or 4-position. In particular embodiments, the 5- or 6-membered heterocyclyl substituent or the $NR^cR^d$ substituent is bonded in the position furthest removed from the carbon ring member which links $R^2$ to the remainder of the formula.

The 5- or 6-membered heterocyclyl and $NR^cR^d$ substituents of the cycloalkyl groups are in general and in particular the same as those of the alkyl groups discussed hereinabove.

$R^3$ of the compounds (A) generally represents optionally substituted $C_1$-$C_6$-alkyl, or optionally substituted $C_3$-$C_6$-cycloalkyl.

In some of the embodiments, the alkyl groups represented by $R^3$ are unsubstituted and the cycloalkyl groups are optionally substituted by 1-3 radicals independently selected from the group of halogen (fluoride, chloride, and bromide), $C_1$-$C_4$-alkyl and $C_1$-$C_4$-alkoxy.

In other embodiments, the alkyl groups in the position of $R^3$ are branched and/or substituted. Illustrative substituents include halogen (i.e., fluoride, chloride, bromide and iodide), hydroxyl, $C_1$-$C_4$-alkoxy, amino, $C_1$-$C_4$-alkylamino, di-($C_1$-$C_4$-alkyl)amino (the alkyl groups being identical or different), $C_1$-$C_6$-alkylcarbonylamino, N—$C_1$-$C_4$-alkyl-N—$C_1$-$C_6$-alkylcarbonylamino (the alkyl groups being identical or different), $C_3$-$C_6$-cycloalkyl, aryl, or heterocyclyl. In one particular aspect of these embodiments, the alkyl groups are branched or are substituted by one of the foregoing substituents. In a further particular aspect of these embodiments the alkyl groups are unbranched and carry 1-3 substituents independently selected from: halogen, hydroxyl, $C_1$-$C_4$-alkoxy, amino, $C_1$-$C_4$-alkylamino, di-($C_1$-$C_4$-alkyl)amino (the alkyl groups being identical or different), $C_1$-$C_6$-alkylcarbonylamino, $C_3$-$C_6$-cycloalkyl, and aryl. In a further particular aspect of these embodiments the alkyl groups are unbranched and carry an aryl or heterocyclyl substituent at or near a terminal carbon of the alkyl group. The aryl substituent of the alkyl group in this aspect is in particular a phenyl group which is optionally substituted by 1-3 radicals independently selected from the group of halogen (fluoride, chloride, bromide and iodide), $C_1$-$C_4$-alkyl and $C_1$-$C_4$-alkoxy. The heterocyclyl substituent of the alkyl group in this aspect is in particular a 5- or 6-membered heterocycle or a heterocyclic moiety corresponding to $NR^cR^d$ as in general and in particular mentioned hereinabove as substituents of the alkyl group represented by $R^2$. The respective heterocycle or heterocyclic moiety is optionally substituted by 1-3 radicals independently selected from the group of halogen (fluoride, chloride, bromide and iodide), $C_1$-$C_4$-alkyl and $C_1$-$C_4$-alkoxy.

In alternative embodiments, the cycloalkyl groups in the position of $R^3$ are substituted. Illustrative substituents include halogen (i.e., fluoride, chloride, bromide and iodide), $C_1$-$C_4$-alkyl, hydroxyl, $C_1$-$C_4$-alkoxy, amino, $C_1$-$C_4$-alkylamino, di-($C_1$-$C_4$-alkyl)amino (the alkyl groups being identical or different), $C_1$-$C_6$-alkylcarbonylamino, N—$C_1$-$C_4$-alkyl-N—$C_1$-$C_6$-alkylcarbonylamino (the alkyl groups being identical or different), $C_3$-$C_6$-cycloalkyl, aryl, or heterocyclyl. In one particular aspect of these embodiments, the cycloalkyl groups carry 1-3 substituents independently selected from: halogen, hydroxyl, $C_1$-$C_4$-alkoxy, amino, $C_1$-$C_4$-alkylamino, di-($C_1$-$C_4$-alkyl)amino (the alkyl groups being identical or different), $C_1$-$C_6$-alkylcarbonylamino, $C_3$-$C_6$-cycloalkyl, and aryl. In a further particular aspect of these embodiments the cycloalkyl groups carry an aryl or heterocyclyl substituent at a position removed from the carbon member which links $R^3$ to the remainder of the formula. The aryl substituent of the cycloalkyl group in this aspect is in particular a phenyl group which is optionally substituted by 1-3 radicals independently selected from the group of halogen (fluoride, chloride, bromide and iodide), $C_1$-$C_4$-alkyl and $C_1$-$C_4$-alkoxy. The heterocyclyl substituent of the cycloalkyl group in this aspect is in particular a 5- or 6-membered heterocycle or a heterocyclic moiety corresponding to $NR^cR^d$ as in general and in particular mentioned hereinabove as substituents of the alkyl group represented by $R^2$. The respective heterocycle or heterocyclic moiety is optionally substituted by 1-3 radicals independently selected from the group of halogen (fluoride, chloride, bromide and iodide), $C_1$-$C_4$-alkyl and $C_1$-$C_4$-alkoxy.

In yet further embodiments, $R^3$ of the compounds (A) represents $C_1$-$C_6$-alkyl which is optionally substituted by $C_3$-$C_6$-cycloalkyl or aryl, or is $C_3$-$C_6$-cycloalkyl.

In one aspect of these embodiments, $R^3$ is unsubstituted straight-chained or branched $C_1$-$C_6$-alkyl, in particular branched $C_3$-$C_6$-alkyl, or is cyclopentyl or cyclohexyl.

In another aspect of these embodiments, $R^3$ is $C_1$-$C_6$-alkyl which is substituted by $C_3$-$C_6$-cycloalkyl (in particular cyclopropyl, cyclopentyl or cyclohexyl) or aryl (in particular phenyl).

The cycloalkyl or aryl substituent of the alkyl group in these embodiments is optionally substituted and is preferably bonded to a terminal carbon of the alkyl group, or to a carbon adjacent to the terminal carbon. In particular aspects of these embodiments, the cycloalkyl or aryl substituent of the alkyl group is optionally substituted by 1-3 radicals independently selected from the group of halogen (fluoride, chloride, bromide, and iodide), $C_1$-$C_4$-alkyl and $C_1$-$C_4$-alkoxy.

$R^4$ of the compounds (A) generally represents hydrogen, $C_1$-$C_4$-alkyl which is optionally substituted by $C_3$-$C_6$-cycloalkyl or aryl, or represents $C_3$-$C_6$-cycloalkyl. Additionally, when the compound (A) is a prodrug, $R^4$ may be a prodrug forming moiety.

In some of the embodiments of the compounds (A) disclosed herein $R^4$ represents hydrogen, $C_1$-$C_3$-alkyl, cyclopropyl-$C_1$-$C_2$-alkyl, phenyl-$C_1$-$C_2$-alkyl, cyclopropyl, cyclopentyl, or cyclohexyl.

In other embodiments, $R^4$ of the compounds (A) represents hydrogen or $C_1$-$C_3$-alkyl, or represents hydrogen, methyl or ethyl.

In particular embodiments, $R^4$ of the compounds (A) represents hydrogen or methyl.

$R^5$ of the compounds (A) generally represents hydrogen, $C_1$-$C_4$-alkyl which is optionally substituted by $C_3$-$C_6$-cycloalkyl or aryl, or represents $C_3$-$C_6$-cycloalkyl. Additionally, when the compound (A) is a prodrug, $R^5$ may be a prodrug forming moiety.

In some of the embodiments of the compounds (A) disclosed herein $R^5$ represents hydrogen, $C_1$-$C_3$-alkyl, cyclopropyl-$C_1$-$C_2$-alkyl, phenyl-$C_1$-$C_2$-alkyl, cyclopropyl, cyclopentyl, or cyclohexyl.

In other embodiments, $R^5$ of the compounds (A) represents hydrogen or $C_1$-$C_3$-alkyl, or represents hydrogen, methyl or ethyl.

In particular embodiments, $R^5$ of the compounds (A) represents hydrogen or methyl.

$R^6$ of the compounds (A) generally represents hydrogen, $C_1$-$C_4$-alkyl which is optionally substituted by $C_3$-$C_6$-cycloalkyl or aryl, or represents $C_3$-$C_6$-cycloalkyl. Additionally, when the compound (A) is a prodrug, $R^6$ may be a prodrug forming moiety.

In some of the embodiments of the compounds (A) disclosed herein $R^6$ represents hydrogen, $C_1$-$C_3$-alkyl, cyclopropyl-$C_1$-$C_2$-alkyl, phenyl-$C_1$-$C_2$-alkyl, cyclopropyl, cyclopentyl, or cyclohexyl.

In other embodiments, $R^6$ of the compounds (A) represents hydrogen or $C_1$-$C_3$-alkyl, or represents hydrogen, methyl or ethyl.

In particular embodiments, $R^6$ of the compounds (A) represents hydrogen or methyl.

$R^7$ of the compounds (A) generally represents hydrogen, $C_1$-$C_6$-alkyl, $C_1$-$C_4$-alkyl which is substituted by $C_3$-$C_6$-cycloalkyl or aryl, or is optionally substituted $C_3$-$C_6$-cycloalkyl. Additionally, when the compound (A) is a prodrug, $R^7$ may be a prodrug forming moiety.

In certain embodiments, $R_6$ of the compounds (A) represents hydrogen, $C_1$-$C_3$-alkyl, cyclopropyl-$C_1$-$C_2$-alkyl, phenyl-$C_1$-$C_2$-alkyl, cyclopropyl, cyclopentyl, or cyclohexyl.

In other embodiments, $R^6$ of the compounds (A) represents hydrogen or $C_1$-$C_3$-alkyl, or represents hydrogen, methyl or ethyl.

In particular embodiments, $R^6$ of the compounds (A) represents hydrogen or methyl.

In some of the embodiments of the compounds (A) disclosed herein, $R^7$ is hydrogen or unsubstituted $C_1$-$C_6$-alkyl. In particular aspects of these embodiments, $R^7$ is hydrogen or $C_1$-$C_4$-alkyl, or is hydrogen, methyl or ethyl.

In further embodiments, $R^7$ represents hydrogen, $C_1$-$C_3$-alkyl, cyclopropyl-$C_1$-$C_2$-alkyl, phenyl-$C_1$-$C_2$-alkyl, cyclopropyl, cyclopentyl, or cyclohexyl.

In other embodiments, $R^7$ of the compounds (A) represents hydrogen or $C_1$-$C_3$-alkyl, or represents hydrogen, methyl or ethyl.

In particular embodiments, $R^7$ of the compounds (A) represents hydrogen or methyl.

Those having ordinary skill in the art will appreciate that compounds (A) in which any two or more of the radicals $Y^1$-$Y^2$ and $R^1$-$R^7$, or all of the radicals $Y^1$-$Y^2$ and $R^1$-$R^7$, reflect the embodiments described in general and in particular hereinbefore, also constitute particular embodiments of compounds (A) and are within the present disclosure.

Accordingly, the particular embodiments of the compounds (I) and (I.a), and the corresponding derivatives thereof, include structures which meet one or more of the following conditions (i) to (vi):
i) $Y^1$, $R^4$, $R^5$, and $R^6$, are identical or different and are hydrogen or $C_1$-$C_4$-alkyl; and/or
ii) $Y^2$ is hydrogen, $C_1$-$C_4$-alkyl or $COR^a$; and/or
iii) $R^1$ is $C_1$-$C_4$-alkyl which is substituted by hydroxyl or $OR^b$; and/or
iv) $R^2$ is $C_1$-$C_6$-alkyl which is substituted by 5- or 6-membered heterocyclyl or $NR^cR^d$; and/or
v) $R^3$ is $C_1$-$C_6$-alkyl which is optionally substituted by $C_3$-$C_6$-alkyl or aryl, or is $C_3$-$C_6$-cycloalkyl; and/or
vi) $R^7$ is hydrogen, $C_1$-$C_6$-alkyl, $C_1$-$C_4$-alkyl which is substituted by aryl.

Additionally, the particular embodiments of the compounds (I) and (I.a), and the corresponding derivatives thereof, include structures which meet one or more of the following conditions (i) to (vi):
i) $Y^1$, $R^4$, $R^5$, and $R^6$, are identical or different and are hydrogen, methyl or ethyl; and/or
ii) $Y^2$ is $COR^a$ and $R^a$ is $C_1$-$C_4$-alkyl, $C_3$-$C_6$-cycloalkyl, or phenyl which is optionally substituted by 1-3 radicals independently selected from the group of halogen (fluoride, chloride, bromide and iodide), $C_1$-$C_4$-alkyl and $C_1$-$C_4$-alkoxy; and/or
iii) $R^1$ is $C_1$-$C_4$-alkyl which is substituted by hydroxyl; and/or
iv) $R^2$ is $C_1$-$C_6$-alkyl which is substituted by amino, $C_1$-$C_4$-alkylamino, di-($C_1$-$C_4$-alkyl)amino (the alkyl groups being identical or different), $C_3$-$C_6$-cycloalkylamino, or an optionally substituted heterocycle selected from the group of tetrahydrofuranyl, pyrrolidinyl, isoxazolidinyl, pyrazolidinyl, oxazolidinyl, imidazolidinyl, 2,3-dihydrofuranyl, 2,5-dihydrofuranyl, 2,3-dihydropyrrolyl, 2,5-dihydropyrrolyl, 2,3-dihydroisoxazolyl, 4,5-dihydroisoxazolyl, 2,5-dihydroisoxazolyl, 2,5-dihydroisoxazolyl, 2,3-dihydropyrazolyl, 4,5-dihydropyrazolyl, 2,3-dihydrooxazolyl, 4,5-dihydrooxazolyl, 2,5-dihydrooxazolyl, 2,3-dihydroimidazolyl, 4,5-dihydroimidazolyl, 2,5-dihydroimidazolyl, morpholinyl, piperidinyl, 1,2,3,4-tetrahydropyridazinyl, 1,2,3,4-tetrahydropyrimidinyl, 1,2,3,4-tetrahydropyrazinyl, tetrahydropyranyl, 3,4,5,6-tetrahydropyridinyl, 3,4-dihydro-1,3-oxazinyl, 2,3-dihydro-1,4-oxazinyl, and 2,3-dihydro-1,4-oxazinyl, and the optional substituents are 1-3 radicals independently selected from the group of halogen (fluoride, chloride, bromide and iodide), $C_1$-$C_4$-alkyl and $C_1$-$C_4$-alkoxy; and/or
v) $R^3$ is $C_1$-$C_6$-alkyl which is optionally substituted by cyclopropyl, cyclopentyl or phenyl; and/or
vi) $R^7$ is hydrogen, $C_1$-$C_6$-alkyl, or benzyl.

Further, the particular embodiments of the compounds (I) and (I.a), and the corresponding derivatives thereof, include structures which meet one or more of the following conditions (i) to (vi):
i) $Y^1$, $R^4$, $R^5$, and $R^6$, are identical or different and are hydrogen, or methyl; and/or
ii) $Y^2$ is $COR^a$ and $R^a$ is $C_1$-$C_4$-alkyl, or phenyl which is optionally substituted by 1-3 radicals independently selected from the group of halogen (fluoride, chloride, bromide and iodide), $C_1$-$C_4$-alkyl and $C_1$-$C_4$-alkoxy; and/or
iii) $R^1$ is $C_1$-$C_4$-alkyl which is substituted by hydroxyl; and/or
iv) $R^2$ is $C_1$-$C_6$-alkyl which is substituted by amino, $C_1$-$C_4$-alkylamino, di-($C_1$-$C_4$-alkyl)amino (the alkyl groups being identical or different), $C_3$-$C_6$-cycloalkylamino, or an optionally substituted heterocycle selected from the group of pyrrolidinyl, isoxazolidinyl, pyrazolidinyl, oxazolidinyl, imidazolidinyl, 2,3-dihydropyrrolyl, 2,5-dihydropyrrolyl, 2,3-dihydroisoxazolyl, 4,5-dihydroisoxazolyl, 2,5-dihydroisoxazolyl, 2,5-dihydroisoxazolyl, 2,3-dihydropyrazolyl, 4,5-dihydropyrazolyl, 2,3-dihydrooxazolyl, 4,5-dihydrooxazolyl, 2,5-dihydrooxazolyl, 2,3-dihydroimidazolyl, 4,5-dihydroimidazolyl, 2,5-dihydroimidazolyl, morpholinyl, piperidinyl, 1,2,3,4-tetrahydropyridazinyl, 1,2,3,4-tetrahydropyrimidinyl, 1,2,3,4-tetrahydropyrazinyl, 3,4,5,6-tetrahydropyridinyl, 3,4-dihydro-1,3-oxazinyl, 2,3-dihydro-1,4-oxazinyl, and 2,3-dihydro-1,4-oxazinyl, and the optional substituents are 1-3 radicals independently selected from the group of halogen (fluoride, chloride, bromide and iodide), $C_1$-$C_4$-alkyl and $C_1$-$C_4$-alkoxy; and/or
v) $R^3$ is $C_1$-$C_6$-alkyl which is optionally substituted by cyclopropyl, cyclopentyl or phenyl; and/or
vi) $R^7$ is hydrogen, $C_1$-$C_4$-alkyl, or benzyl.

Correspondingly, the particular embodiments of the compounds (II) and (II.a), and the derivatives thereof, include structures which meet one or more of the following conditions (i) to (v):
  $Y^1$, $R^4$, $R^5$, and $R^6$, are identical or different and are hydrogen or $C_1$-$C_4$-alkyl; and/or
  ii) $R^1$ is $C_1$-$C_4$-alkyl which is substituted by hydroxyl or $OR^b$; and/or
  iii) $R^2$ is $C_1$-$C_6$-alkyl which is substituted by 5- or 6-membered heterocyclyl or $NR^cR^d$; and/or
  iv) $R^3$ is $C_1$-$C_6$-alkyl which is optionally substituted by $C_3$-$C_6$-alkyl or aryl, or is $C_3$-$C_6$-cycloalkyl; and/or
  v) $R^7$ is hydrogen, $C_1$-$C_6$-alkyl, $C_1$-$C_4$-alkyl which is substituted by aryl.

Additionally, the particular embodiments of the compounds (II) and (II.a), and the derivatives thereof, include structures which meet one or more of the following conditions (i) to (v):
  i) $Y^1$, $R^4$, $R^5$, and $R^6$, are identical or different and are hydrogen, methyl or ethyl; and/or
  ii) $R^1$ is $C_1$-$C_4$-alkyl which is substituted by hydroxyl; and/or
  iii) $R^2$ is $C_1$-$C_6$-alkyl which is substituted by amino, $C_1$-$C_4$-alkylamino, di-($C_1$-$C_4$-alkyl)amino (the alkyl groups being identical or different), $C_3$-$C_6$-cycloalkylamino, or an optionally substituted heterocycle selected from the group of tetrahydrofuranyl, pyrrolidinyl, isoxazolidinyl, pyrazolidinyl, oxazolidinyl, imidazolidinyl, 2,3-dihydrofuranyl, 2,5-dihydrofuranyl, 2,3-dihydropyrrolyl, 2,5-dihydropyrrolyl, 2,3-dihydroisoxazolyl, 4,5-dihydroisoxazolyl, 2,5-dihydroisoxazolyl, 2,5-dihydroisoxazolyl, 2,3-dihydropyrazolyl, 4,5-dihydropyrazolyl, 2,3-dihydrooxazolyl, 4,5-dihydrooxazolyl, 2,5-dihydrooxazolyl, 2,3-dihydroimidazolyl, 4,5-dihydroimidazolyl, 2,5-dihydroimidazolyl, morpholinyl, piperidinyl, 1,2,3,4-tetrahydropyridazinyl, 1,2,3,4-tetrahydropyrimidinyl, 1,2,3,4-tetrahydropyrazinyl, tetrahydropyranyl, 3,4,5,6-tetrahydropyridinyl, 3,4-dihydro-1,3-oxazinyl, 2,3-dihydro-1,4-oxazinyl, and 2,3-dihydro-1,4-oxazinyl, and the optional substituents are 1-3 radicals independently selected from the group of halogen (fluoride, chloride, bromide and iodide), $C_1$-$C_4$-alkyl and $C_1$-$C_4$-alkoxy; and/or
  iv) $R^3$ is $C_1$-$C_6$-alkyl which is optionally substituted by cyclopropyl, cyclopentyl or phenyl; and/or
  v) $R^7$ is hydrogen, $C_1$-$C_6$-alkyl, or benzyl.

Further, the particular embodiments of the compounds (II) and (II.a), and the derivatives thereof, include structures which meet one or more of the following conditions (i) to (v):
  i) $Y^1$, $R^4$, $R^5$, and $R^6$, are identical or different and are hydrogen, or methyl; and/or
  ii) $R^1$ is $C_1$-$C_4$-alkyl which is substituted by hydroxyl; and/or
  iii) $R^2$ is $C_1$-$C_6$-alkyl which is substituted by amino, $C_1$-$C_4$-alkylamino, di-($C_1$-$C_4$-alkyl)amino (the alkyl groups being identical or different), $C_3$-$C_6$-cycloalkylamino, or an optionally substituted heterocycle selected from the group of pyrrolidinyl, isoxazolidinyl, pyrazolidinyl, oxazolidinyl, imidazolidinyl, 2,3-dihydropyrrolyl, 2,5-dihydropyrrolyl, 2,3-dihydroisoxazolyl, 4,5-dihydroisoxazolyl, 2,5-dihydroisoxazolyl, 2,5-dihydroisoxazolyl, 2,3-dihydropyrazolyl, 4,5-dihydropyrazolyl, 2,3-dihydrooxazolyl, 4,5-dihydrooxazolyl, 2,5-dihydrooxazolyl, 2,3-dihydroimidazolyl, 4,5-dihydroimidazolyl, 2,5-dihydroimidazolyl, morpholinyl, piperidinyl, 1,2,3,4-tetrahydropyridazinyl, 1,2,3,4-tetrahydropyrimidinyl, 1,2,3,4-tetrahydropyrazinyl, 3,4,5,6-tetrahydropyridinyl, 3,4-dihydro-1,3-oxazinyl, 2,3-dihydro-1,4-oxazinyl, and 2,3-dihydro-1,4-oxazinyl, and the optional substituents are 1-3 radicals independently selected from the group of halogen (fluoride, chloride, bromide and iodide), $C_1$-$C_4$-alkyl and $C_1$-$C_4$-alkoxy; and/or
  iv) $R^3$ is $C_1$-$C_6$-alkyl which is optionally substituted by cyclopropyl, cyclopentyl or phenyl; and/or
  v) $R^7$ is hydrogen, $C_1$-$C_4$-alkyl, or benzyl.

Similarly, the particular embodiments of the compounds (III) and (III.a), and the derivatives thereof, include structures which meet one or more of the following conditions (i) to (v):
  i) $Y^1$, $R^4$, $R^5$, and $R^6$, are identical or different and are hydrogen or $C_1$-$C_4$-alkyl; and/or
  ii) $R^1$ is $C_1$-$C_4$-alkyl which is substituted by hydroxyl or $OR^b$; and/or
  iii) $R^2$ is $C_1$-$C_6$-alkyl which is substituted by 5- or 6-membered heterocyclyl or $NR^cR^d$; and/or
  iv) $R^3$ is $C_1$-$C_6$-alkyl which is optionally substituted by $C_3$-$C_6$-alkyl or aryl, or is $C_3$-$C_6$-cycloalkyl; and/or
  v) $R^7$ is hydrogen, $C_1$-$C_6$-alkyl, $C_1$-$C_4$-alkyl which is substituted by aryl.

Additionally, the particular embodiments of the compounds (III) and (III.a), and the derivatives thereof, include structures which meet one or more of the following conditions (i) to (v):
  i) $Y^1$, $R^4$, $R^5$, and $R^6$, are identical or different and are hydrogen, methyl or ethyl; and/or
  ii) $R^1$ is $C_1$-$C_4$-alkyl which is substituted by hydroxyl; and/or
  iii) $R^2$ is $C_1$-$C_6$-alkyl which is substituted by amino, $C_1$-$C_4$-alkylamino, di-($C_1$-$C_4$-alkyl)amino (the alkyl groups being identical or different), $C_3$-$C_6$-cycloalkylamino, or an optionally substituted heterocycle selected from the group of tetrahydrofuranyl, pyrrolidinyl, isoxazolidinyl, pyrazolidinyl, oxazolidinyl, imidazolidinyl, 2,3-dihydrofuranyl, 2,5-dihydrofuranyl, 2,3-dihydropyrrolyl, 2,5-dihydropyrrolyl, 2,3-dihydroisoxazolyl, 4,5-dihydroisoxazolyl, 2,5-dihydroisoxazolyl, 2,5-dihydroisoxazolyl, 2,3-dihydropyrazolyl, 4,5-dihydropyrazolyl, 2,3-dihydrooxazolyl, 4,5-dihydrooxazolyl, 2,5-dihydrooxazolyl, 2,3-dihydroimidazolyl, 4,5-dihydroimidazolyl, 2,5-dihydroimidazolyl, morpholinyl, piperidinyl, 1,2,3,4-tetrahydropyridazinyl, 1,2,3,4-tetrahydropyrimidinyl, 1,2,3,4-tetrahydropyrazinyl, tetrahydropyranyl, 3,4,5,6-tetrahydropyridinyl, 3,4-dihydro-1,3-oxazinyl, 2,3-dihydro-1,4-oxazinyl, and 2,3-dihydro-1,4-oxazinyl, and the optional substituents are 1-3 radicals independently selected from the group of halogen (fluoride, chloride, bromide and iodide), $C_1$-$C_4$-alkyl and $C_1$-$C_4$-alkoxy; and/or
  iv) $R^3$ is $C_1$-$C_6$-alkyl which is optionally substituted by cyclopropyl, cyclopentyl or phenyl; and/or
  v) $R^7$ is hydrogen, $C_1$-$C_6$-alkyl, or benzyl.

Further, the particular embodiments of the compounds (III) and (III.a), and the derivatives thereof, include structures which meet one or more of the following conditions (i) to (v):

i) $Y^1$, $R^4$, $R^5$, and $R^6$, are identical or different and are hydrogen, or methyl; and/or ii) $R^1$ is $C_1$-$C_4$-alkyl which is substituted by hydroxyl; and/or iii) $R^2$ is $C_1$-$C_6$-alkyl which is substituted by amino, $C_1$-$C_4$-alkylamino, di-($C_1$-$C_4$-alkyl)amino (the alkyl groups being identical or different), $C_3$-$C_6$-cycloalkylamino, or an optionally substituted heterocycle selected from the group of pyrrolidinyl, isoxazolidinyl, pyrazolidinyl, oxazolidinyl, imidazolidinyl, 2,3-dihydropyrrolyl, 2,5-dihydropyrrolyl, 2,3-dihydroisoxazolyl, 4,5-dihydroisoxazolyl, 2,5-dihydroisoxazolyl, 2,5-dihydroisoxazolyl, 2,3-dihydropyrazolyl, 4,5-dihydropyrazolyl, 2,3-dihydrooxazolyl, 4,5-dihydrooxazolyl, 2,5-dihydrooxazolyl, 2,3-dihydroimidazolyl, 4,5-dihydroimidazolyl, 2,5-dihydroimidazolyl, morpholinyl, piperidinyl, 1,2,3,4-tetrahydropyridazinyl, 1,2,3,4-tetrahydropyrimidinyl, 1,2,3,4-tetrahydropyrazinyl, 3,4,5,6-tetrahydropyridinyl, 3,4-dihydro-1,3-oxazinyl, 2,3-dihydro-1,4-oxazinyl, and 2,3-dihydro-1,4-oxazinyl, and the optional substituents are 1-3 radicals independently selected from the group of halogen (fluoride, chloride, bromide and iodide), $C_1$-$C_4$-alkyl and $C_1$-$C_4$-alkoxy; and/or iv) $R^3$ is $C_1$-$C_6$-alkyl which is optionally substituted by cyclopropyl, cyclopentyl or phenyl; and/or v) $R^7$ is hydrogen, $C_1$-$C_4$-alkyl, or benzyl.

The compounds (A') can be prepared in manners analogous to conventional peptide synthesis. The compounds (A') are typically prepared using a solid phase synthetic procedure as outlined in Scheme 1.

Scheme 1:

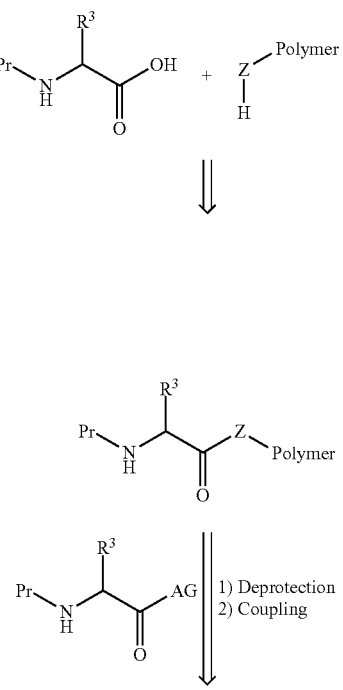

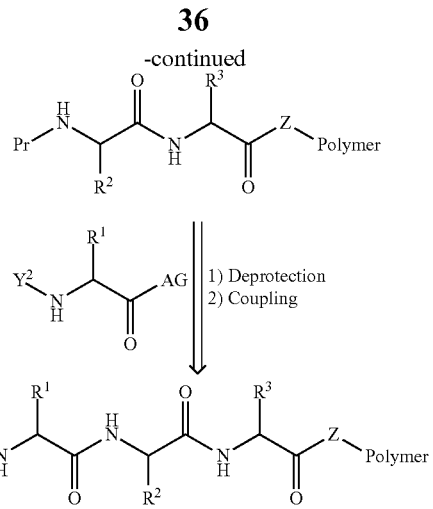

In Scheme 1, Pr is a conventional protecting group, AG is an activating group, $R^1$, $R^2$, $R^3$, and $Y^2$ have the aforementioned meanings, and Z is O or NH.

Suitable protecting groups are known in the art and include carbobenzyloxy (Cbz; removed by hydrogenolysis), p-methoxybenzyl carbonyl (Moz or MeOZ; removed by hydrogenolysis), tert-butyloxycarbonyl (BOC; removed by concentrated strong acid (such as HCl or $CF_3COOH$), or by heating to ±80° C.), 9-fluorenylmethyloxycarbonyl (FMOC; removed by base, such as piperidine), acetyl (Ac; removed by treatment with a base, most often, with aqueous or gaseous ammonia or methylamine), benzoyl (Bz; removed by treatment with a base, most often with aqueous or gaseous ammonia or methylamine), benzyl (Bn; removed by hydrogenolysis), carbamate (removed by acid and mild heating), p-methoxybenzyl (PMB; removed by hydrogenolysis), 3,4-dimethoxybenzyl (DMPM; removed by hydrogenolysis), p-methoxyphenyl (PMP; removed by ammonium cerium(IV) nitrate (CAN)), tosyl (Ts; removed by concentrated acid (HBr, $H_2SO_4$) and strong reducing agents (sodium in liquid ammonia or sodium naphthalenide)) and other sulfonamides (Nosyl and Nps; removed by samarium iodide, tributyltin hydride). In particular embodiments, the protecting groups are: di-t-butly dicarbonate (BOC), fluorenylmethyloxycarbonate (FM), 4-methoxy-2,3,6-trimethylbenzenesulfonate (Mtr), trityl and 2,4,6-trimethoxybenzyl (Tmob).

Suitable activating groups are also known in the art, and include carbodiimides, e.g., dicyclohexylcarbodiimide (DCC) and diisopropylcarbodiimide (DIC), and triazoles, e.g., 1-hydroxy-benzotriazole (HOBt) and 1-hydroxy-7-azabenzotriazole (HOAt). Alternatively, the active ester can be introduced as a uronium or phosphonium salt of a non-nucleophilic anion (tetrafluoroborate or hexafluorophosphate): HBTU (2-(1H-benzotriazol-1-yl)-1,1,3,3-tetramethyluronium hexafluorophosphate), HATU (O-(7-azabenzotriazol-1-yl)-N,N,N',N'-tetramethyluronium hexafluorophosphate), HCTU (1H-benzotriazolium 1-[bis(dimethylamino)methylene]-5-chloro hexafluorophosphate (1-),3-oxide), TBTU (O-(benzotriazol-1-yl)-N,N,N',N'-tetramethyluronium tetrafluoroborate) and PyBOP (benzotriazol-1-yloxytripyrrolidinophosphonium hexafluorophosphate).

Any solid synthetic polymer which bears a reactive group such as —OH or $NH_2$ can be used and such polymers are known to those of ordinary skill in the peptide synthesis art. The OH or $NH_2$ reactive groups are convenient because they react readily with the carboxyl group of an N-α-protected amino acid. A convenient and commercially available polymer is the so-called Rink resin schematically shown below:

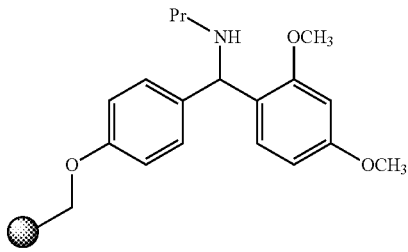

Once the initial N-α-protected amino acid is bonded to the reactive group of the polymer, the amino protecting group can be removed and a second N-α-protected amino acid can be coupled to the attached amino acid. These steps are repeated until the desired compound is obtained. At the end of the synthesis, the desired compound is cleaved from the resin, separated and purified, typically by using some type of automated system such as an HPLC.

Generally, different amino acids consisting of different substituents at a central carbon atom (called the α-carbon) are used. Different amine protecting groups can be used including a BOC or an Fmoc derivative. The choice of the protecting group can vary depending upon the substituent at the α-carbon. For example, when the radical $R^1$, $R^2$ or $R^3$ contains functional groups that can interfere with the formation of the amide bond, such functional groups need to be protected as well and remain protected throughout the synthesis. Therefore, it is important to mask the functional groups of the amino acid side chain.

The compounds (A) are particularly suited to modulate TGF-β activity and for treating diseases associated with a dysregulation of TGF-β, in particular such diseases which are associated with abnormal and increased TGF-β activity. Such diseases include, in particular, fibrotic conditions of organs such as the liver, the lung, the cardiac muscle, the kidney, the skin (e.g., dermal scarring), and the eye (e.g., glaucoma), cancers such as multiple myeloma and hematologic malignancy, as well as bone loss and immune dysfunctions such as rheumatoid arthritis and chronic renal allograft rejection.

Accordingly, in one embodiment, the present disclosure relates to a method of treating a patient suffering from a disease or dysfunction associated with abnormal and increased TGF-β activity, which comprises administering to the patient an effective amount of at least one compound (A). In another embodiment, the present disclosure relates to a method of reducing the activation of TGF-β in a patient adversely affected by abnormal and increased TGF-β activity, which comprises administering to the patient at least one compound (A) in an amount sufficient to reduce or inhibit the activation of latent TGF-β by thrombospondin1 (TSP1).

In these methods, the compounds (A) generally can be administered to the patient either alone or as part of a pharmaceutical composition comprising the compound(s) and a pharmaceutically acceptable carrier. Frequently, the nature of the carrier will depend on the desired administration method and/or the nature of the disease to be treated.

The compositions can be administered to the patients either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Those having ordinary skill in the art will appreciate that the compositions suitable for parenteral injection also are suitable for use in implants and modules. Examples of well-known implants and modules useful in the present invention include:

an implantable micro-infusion pump for dispensing medication at a controlled rate (U.S. Pat. No. 4,487,603);
a therapeutic device for administering medication through the skin (U.S. Pat. No. 4,486,194);
a medication infusion pump for delivering medication at a precise infusion rate (U.S. Pat. No. 4,447,233);
a variable flow implantable infusion apparatus for continuous drug delivery (U.S. Pat. No. 4,447,224);
an osmotic drug delivery system having multi-chamber compartments (U.S. Pat. No. 4,439,196); and
an osmotic drug delivery system (U.S. Pat. No. 4,475,196).
Many other such implants, delivery systems, and modules are well known to those skilled in the art.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the compositions can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds (A) are typically administered to the patient in a therapeutically effective amount, i.e., a total amount of one or more compounds (A) that, when administered to the patient, ameliorates a symptom of the disease.

The compound(s) (A) can be administered to a patient or subject at dosage levels in the range of about 35 mg to about 700 mg per day. For a normal human adult having a body weight of about 70 kilograms, a dosage in the range of about 0.5 mg to about 10 mg per kilogram of body weight per day is preferable. The specific dosage used, however, may vary. For example, the dosage can depend on a number of factors including the requirements of the patient, the severity of the condition being treated, and the pharmacological activity of the compound being used. The determination of optimum dosages for a particular patient is well known to those skilled in the art.

| Table of Abbreviations: | |
|---|---|
| Ac | acetyl (CH$_3$—C(=O)—) |
| CD36 | cluster of differentiation 36 |
| CD47 | cluster of differentiation 47 |
| CD138 | cluster of differentiation 138 |
| ECM | extracellular matrix |
| EGF | epidermal growth factor |
| ELISA | enzyme-linked immuno sorbent assay |
| FGF | fibroblast growth factor |
| IGF-1 | insulin-like growth factor 1 |
| IGFBP5 | insulin-like growth factor-binding protein 5 |
| Ig kappa | immunoglobulin kappa |
| IL-6 | interleukin 6 |
| IL-17 | interleukin 17 |
| i.p. | intraperitoneal |
| KRFK | lysine-arginine-phenylalanine-lysine |
| LAP | latency associated peptide |
| LSKL | leucine-serine-lysine-leucine |
| Mab 133 | monoclonal antibody 133 |
| MM | multiple myeloma |
| MMP | matrix metalloproteinases |
| RANKL | receptor activator of nuclear factor kappa-B ligand |
| Runx2 | Runt-related transcription factor 2 |
| TGF-β | transforming growth factor beta |
| TIMP-1 | TIMP metallopeptidase inhibitor 1 |
| TRAP5b | tartrate-resistant acid phosphatase active isoform b |
| TSP1 | thrombospondin1 |
| TSRs | TSP1 type 1 repeats |
| UUO | tubulointerstitial fibrosis |
| VEGF | vascular endothelial growth factor |
| VLA-4 | integrin α$_4$β$_1$; very vate antigen-4 |

Table of Non-Patent Documents:

Adams, J. C. and J. Lawler (2004). "The thrombospondins." *Int J Biochem Cell Biol* 36(6): 961-968.

Adams, J. C. and J. Lawler (2011). "The thrombospondins." *Cold Spring Harbor perspectives in biology* 3(10): a009712.

Agah, A., T. R. Kyriakides, J. Lawler and P. Bornstein (2002). "The lack of thrombospondin-1 (TSP1) dictates the course of wound healing in double-TSP1/TSP2-null mice." *Am J Pathol* 161(3): 831-839.

Anderson, K. C. and R. D. Carrasco (2011). "Pathogenesis of myeloma." *Annual review of pathology* 6: 249-274.

Belmadani, S., J. Bernal, C. C. Wei, M. A. Pallero, L. Dell'italia, J. E. Murphy-Ullrich and K. H. Berecek (2007). "A thrombospondin-1 antagonist of transforming growth factor-beta activation blocks cardiomyopathy in rats with diabetes and elevated angiotensin II." *Am J Pathol* 171(3): 777-789.

Breitkopf, K., I. Sawitza, J. H. Westhoff, L. Wickert, S. Dooley and A. M. Gressner (2005). "Thrombospondin 1 acts as a strong promoter of transforming growth factor beta effects via two distinct mechanisms in hepatic stellate cells." *Gut* 54(5): 673-681.

Canon, J. A., C. A. Walsh, W. D. Fraser and J. A. Gallagher (1995). "Thrombospondin promotes resorption by osteoclasts in vitro." *Biochem Biophys Res Commun* 213(3): 1017-1025.

-continued

Table of Non-Patent Documents:

Cauchard, J. H., A. Berton, G. Godeau, W. Hornebeck and G. Bellon (2004). "Activation of latent transforming growth factor beta 1 and inhibition of matrix metalloprotease activity by a thrombospondin-like tripeptide linked to elaidic acid." *Biochemical pharmacology* 67(11): 2013-2022.

Chen, Y., A. Leask, D. J. Abraham, L. Kennedy, X. Shi-Wen, C. P. Denton, C. M. Black, L. S. Verjee and M. Eastwood (2011). "Thrombospondin 1 is a key mediator of transforming growth factor beta-mediated cell contractility in systemic sclerosis via a mitogen-activated protein kinase kinase (MEK)/extracellular signal-regulated kinase (ERK)-dependent mechanism." *Fibrogenesis & tissue repair* 4(1): 9.

Chen, Y., X. Wang, D. Weng, L. Tian, L. Lv, S. Tao and J. Chen (2009). "A TSP-1 synthetic peptide inhibits bleomycin-induced lung fibrosis in mice." *Experimental and Toxicologic Pathology* 61(1): 59-65.

Chipev, C. C., R. Simman, G. Hatch, A. E. Katz, D. M. Siegel and M. Simon (2000). "Myofibroblast phenotype and apoptosis in keloid and palmar fibroblasts in vitro." *Cell Death Differ* 7(2): 166-176.

Connolly, E. C., E. F. Saunier, D. Quigley, M. T. Luu, A. De Sapio, B. Hann, J. M. Yingling and R. J. Akhurst (2011). "Outgrowth of drug-resistant carcinomas expressing markers of tumor aggression after long-term TbetaRI/II kinase inhibition with LY2109761." *Cancer research* 71(6): 2339-2349.

Crawford, S. E., V. Stellmach, J. E. Murphy-Ullrich, S. M. Ribeiro, J. Lawler, R. O. Hynes, G. P. Boivin and N. Bouck (1998). "Thrombospondin-1 is a major activator of TGF-beta1 in vivo." *Cell* 93(7): 1159-1170.

Daniel, C., K. Schaub, K. Amann, J. Lawler and C. Hugo (2007). "Thrombospondin-1 is an endogenous activator of TGF-beta in experimental diabetic nephropathy in vivo." *Diabetes* 56(12): 2982-2989.

Daniel, C., Y. Takabatake, M. Mizui, Y. Isaka, H. Kawashi, H. Rupprecht, E. Imai and C. Hugo (2003). "Antisense oligonucleotides against thrombospondin-1 inhibit activation of tgf-beta in fibrotic renal disease in the rat in vivo." *Am J Pathol* 163(3): 1185-1192.

Daniel, C., J. Wiede, H. C. Krutzsch, S. M. Ribeiro, D. D. Roberts, J. E. Murphy-Ullrich and C. Hugo (2004). "Thrombospondin-1 is a major activator of TGF-beta in fibrotic renal disease in the rat in vivo." *Kidney international* 65(2): 459-468.

Derks, R. A., E. Jankowska-Gan, Q. Xu and W. J. Burlingham (2007). "Dendritic cell type determines the mechanism of bystander suppression by adaptive T regulatory cells specific for the minor antigen HA-1." *Journal of immunology* 179(6): 3443-3451.

Diop-Frimpong, B., V. P. Chauhan, S. Krane, Y. Boucher and R. K. Jain (2011). "Losartan inhibits collagen I synthesis and improves the distribution and efficacy of nanotherapeutics in tumors." *Proceedings of the National Academy of Sciences of the United States of America* 108(7): 2909-2914.

DiPietro, L. A., N. N. Nissen, R. L. Gamelli, A. E. Koch, J. M. Pyle and P. J. Polverini (1996). "Thrombospondin 1 synthesis and function in wound repair." *Am J Pathol* 148(6): 1851-1860.

Dong, M. and G. C. Blobe (2006). "Role of transforming growth factor-beta in hematologic malignancies." *Blood* 107(12): 4589-4596.

Flavell, R. A., S. Sanjabi, S. H. Wrzesinski and P. Licona-Limon (2010). "The polarization of immune cells in the tumour environment by TGFbeta." *Nature reviews. Immunology* 10(8): 554-567.

Futagami, Y., S. Sugita, J. Vega, K. Ishida, H. Takase, K. Maruyama, H. Aburatani and M. Mochizuki (2007). "Role of thrombospondin-1 in T cell response to ocular pigment epithelial cells." *J Immunol* 178(11): 6994-7005.

Harpel, J. G., S. Schultz-Cherry, J. E. Murphy-Ullrich and D. B. Rifkin (2001). "Tamoxifen and estrogen effects on TGF-beta formation: role of thrombospondin-1, alphavbeta3, and integrin-associated protein." *Biochemical and biophysical research communications* 284(1): 11-14.

Hayashi, T., T. Hideshima, A. N. Nguyen, O. Munoz, K. Podar, M. Hamasaki, K. Ishitsuka, H. Yasui, P. Richardson, S. Chakravarty, A. Murphy, D. Chauhan, L. S. Higgins and K. C. Anderson (2004). "Transforming growth factor beta receptor I kinase inhibitor down-regulates cytokine secretion and multiple myeloma cell growth in the bone marrow microenvironment." *Clin Cancer Res* 10(22): 7540-7546.

Hugo, C. (2003). "The thrombospondin 1-TGF-beta axis in fibrotic renal disease." *Nephrol Dial Transplant* 18(7): 1241-1245.

Isufi, I., M. Seetharam, L. Zhou, D. Sohal, J. Opalinska, P. Pahanish and A. Verma (2007). "Transforming growth factor-beta signaling in normal and malignant hematopoiesis." *Journal of interferon & cytokine research: the official journal of the International Society for Interferon and Cytokine Research* 27(7): 543-552.

Jou, I. M., A. L. Shiau, S. Y. Chen, C. R. Wang, D. B. Shieh, C. S. Tsai and C. L. Wu (2005). "Thrombospondin 1 as an effective gene therapeutic strategy in collagen-induced arthritis." *Arthritis Rheum* 52(1): 339-344.

K. Bailey DuBose, M. Zayzafoon and J. E. Murphy-Ullrich (2012). "Thrombospondin-1 inhibits osteogenic differentiation of human mesenchymal stem cells through latent TGF-beta activation." *Biochemical and Biophysical Research Communications* 422(3): 488-493.

Kondou, H., S. Mushiake, Y. Etani, Y. Miyoshi, T. Michigami and K. Ozono (2003). "A blocking peptide for transforming growth factor-beta1 activation prevents hepatic fibrosis in vivo." *Journal of hepatology* 39(5): 742-748.

Kukreja, A., S. Radfar, B. H. Sun, K. Insogna and M. V. Dhodapkar (2009). "Dominant role of CD47-thrombospondin-1 interactions in myeloma-induced fusion of human dendritic cells: implications for bone disease." *Blood* 114(16): 3413-3421.

Table of Non-Patent Documents:

Lanz, T. V., Z. Ding, P. P. Ho, J. Luo, A. N. Agrawal, H. Srinagesh, R. Axtell, H. Zhang, M. Platten, T. Wyss-Coray and L. Steinman (2010). "Angiotensin II sustains brain inflammation in mice via TGF-beta." *The Journal of clinical investigation* 120(8): 2782-2794.

Liu, S., L. Shi and S. Wang (2007). "Overexpression of upstream stimulatory factor 2 accelerates diabetic kidney injury." *American journal of physiology. Renal physiology* 293(5): F1727-1735.

Longo, V., O. Brunetti, S. D'Oronzo, F. Dammacco and F. Silvestris (2012). "Therapeutic approaches to myeloma bone disease: An evolving story." *Cancer treatment reviews*.

Lu, A., M. Miao, T. R. Schoeb, A. Agarwal and J. E. Murphy-Ullrich (2011). "Blockade of TSP1-dependent TGF-beta activity reduces renal injury and proteinuria in a murine model of diabetic nephropathy." *The American journal of pathology* 178(6): 2573-2586.

Ludlow, A., K. O. Yee, R. Lipman, R. Bronson, P. Weinreb, X. Huang, D. Sheppard and J. Lawler (2005). "Characterization of integrin beta6 and thrombospondin-1 double-null mice." *J Cell Mol Med* 9(2): 421-437.

Matsumoto, T. and M. Abe (2011). "TGF-beta-related mechanisms of bone destruction in multiple myeloma." *Bone* 48(1): 129-134.

Miao, W. M., W. L. Seng, M. Duquette, P. Lawler, C. Laus and J. Lawler (2001). "Thrombospondin-1 type 1 repeat recombinant proteins inhibit tumor growth through transforming growth factor-beta-dependent and -independent mechanisms." *Cancer Res* 61(21): 7830-7839.

Mimura, Y., H. Ihn, M. Jinnin, Y. Asano, K. Yamane and K. Tamaki (2005). "Constitutive thrombospondin-1 overexpression contributes to autocrine transforming growth factor-beta signaling in cultured scleroderma fibroblasts." *Am J Pathol* 166(5): 1451-1463.

Morishima, Y., A. Nomura, Y. Uchida, Y. Noguchi, T. Sakamoto, Y. Ishii, Y. Goto, K. Masuyama, M. J. Zhang, K. Hirano, M. Mochizuki, M. Ohtsuka and K. Sekizawa (2001). "Triggering the induction of myofibroblast and fibrogenesis by airway epithelial shedding." *American journal of respiratory cell and molecular biology* 24(1): 1-11.

Murphy-Ullrich, J. E. and D. F. Mosher (1985). "Localization of thrombospondin in clots formed in situ." *Blood* 66(5): 1098-1104.

Murphy-Ullrich, J. E. and M. Poczatek (2000). "Activation of latent TGF-beta by thrombospondin-1: mechanisms and physiology." *Cytokine & growth factor reviews* 11(1-2): 59-69.

Myung, S. J., J. H. Yoon, G. Y. Gwak, W. Kim, J. I. Yang, S. H. Lee, J. J. Jong and H. S. Lee (2007). "Bile acid-mediated thrombospondin-1 induction in hepatocytes leads to transforming growth factor-beta-dependent hepatic stellate cell activation." *Biochem Biophys Res Commun* 353(4): 1091-1096.

Naito, T., T. Masaki, D. J. Nikolic-Paterson, C. Tanji, N. Yorioka and N. Kohno (2004). "Angiotensin II induces thrombospondin-1 production in human mesangial cells via p38 MAPK and JNK: a mechanism for activation of latent TGF-beta1." *American journal of physiology. Renal physiology* 286(2): F278-287.

Noonan, K., L. Marchionni, J. Anderson, D. Pardoll, G. D. Roodman and I. Borrello (2010). "A novel role of IL-17-producing lymphocytes in mediating lytic bone disease in multiple myeloma." *Blood* 116(18): 3554-3563.

Nor, J. E., L. Dipietro, J. E. Murphy-Ullrich, R. O. Hynes, J. Lawler and P. J. Polverini (2005). "Activation of Latent TGF-beta1 by Thrombospondin-1 is a Major Component of Wound Repair." *Oral biosciences & medicine*: *OBM* 2(2): 153-161.

Pierson, B. A., K. Gupta, W. S. Hu and J. S. Miller (1996). "Human natural killer cell expansion is regulated by thrombospondin-mediated activation of transforming growth factor-beta 1 and independent accessory cell-derived contact and soluble factors." *Blood* 87(1): 180-189.

Poczatek, M. H., C. Hugo, V. Darley-Usmar and J. E. Murphy-Ullrich (2000). "Glucose stimulation of transforming growth factor-beta bioactivity in mesangial cells is mediated by thrombospondin-1." *Am J Pathol* 157(4): 1353-1363.

Pohlers, D., A. Beyer, D. Koczan, T. Wilhelm, H. J. Thiesen and R. W. Kinne (2007). "Constitutive upregulation of the transforming growth factor-beta pathway in rheumatoid arthritis synovial fibroblasts." *Arthritis research & therapy* 9(3): R59.

Pour, L., H. Svachova, Z. Adam, M. Almasi, L. Buresova, T. Buchler, L. Kovarova, P. Nemec, M. Penka, J. Vorlicek and R. Hajek (2010). "Levels of angiogenic factors in patients with multiple myeloma correlate with treatment response." *Annals of hematology* 89(4): 385-389.

Prabhala, R. H., D. Pelluru, M. Fulciniti, H. K. Prabhala, P. Nanjappa, W. Song, C. Pai, S. Amin, Y. T. Tai, P. G. Richardson, I. M. Ghobrial, S. P. Treon, J. F. Daley, K. C. Anderson, J. L. Kutok, et al. (2010). "Elevated IL-17 produced by TH17 cells promotes myeloma cell growth and inhibits immune function in multiple myeloma." *Blood* 115(26): 5385-5392.

Prud'homme, G. J. (2007). "Pathobiology of transforming growth factor beta in cancer, fibrosis and immunologic disease, and therapeutic considerations." *Laboratory investigation; a journal of technical methods and pathology* 87(11): 1077-1091.

Raugi, G. J., J. E. Olerud and A. M. Gown (1987). "Thrombospondin in early human wound tissue." *J Invest Dermatol* 89(6): 551-554.

Reed, M. J., P. Puolakkainen, T. F. Lane, D. Dickerson, P. Bornstein and E. H. Sage (1993). "Differential expression of SPARC and thrombospondin 1 in wound repair: immunolocalization and in situ hybridization." *J Histochem Cytochem* 41(10): 1467-1477.

Sakai, K., Y. Sumi, H. Muramatsu, K. Hata, T. Muramatsu and M. Ueda (2003). "Thrombospondin-1 promotes fibroblast-mediated collagen gel contraction caused by activation of latent transforming growth factor beta-1." *J Dermatol Sci* 31(2): 99-109.

Sasaki, A., H. Naganuma, E. Satoh, T. Kawataki, K. Amagasaki and H. Nukui (2001). "Participation of thrombospondin-1 in the activation of latent transforming growth factor-beta in malignant glioma cells." *Neurologia medico-chirurgica* 41(5): 253-258; discussion 258-259.

| Table of Non-Patent Documents: |
|---|
| Schultz-Cherry, S. and J. E. Murphy-Ullrich (1993). "Thrombospondin causes activation of latent transforming growth factor-β secreted by endothelial cells by a novel mechanism." *J Cell Biol* 122(4): 923-932. |
| Sweetwyne, M. T. and J. E. Murphy-Ullrich (2012). "Thrombospondin1 in tissue repair and fibrosis: TGF-beta-dependent and independent mechanisms." *Matrix biology: journal of the International Society for Matrix Biology* 31(3): 178-186. |
| Takeuchi, K., M. Abe, M. Hiasa, A. Oda, H. Amou, S. Kido, T. Harada, O. Tanaka, H. Miki, S. Nakamura, A. Nakano, K. Kagawa, K. Yata, S. Ozaki and T. Matsumoto (2010). "Tgf-Beta inhibition restores terminal osteoblast differentiation to suppress myeloma growth." *PloS one* 5(3): e9870. |
| Ueno, A., Y. Miwa, K. Miyoshi, T. Horiguchi, H. Inoue, I. Ruspita, K. Abe, K. Yamashita, E. Hayashi and T. Noma (2006). "Constitutive expression of thrombospondin 1 in MC3T3-E1 osteoblastic cells inhibits mineralization." *J Cell Physiol* 209(2): 322-332. |
| Urashima, M., A. Ogata, D. Chauhan, M. Hatziyanni, M. B. Vidriales, D. A. Dedera, R. L. Schlossman and K. C. Anderson (1996). "Transforming growth factor-beta1: differential effects on multiple myeloma versus normal B cells." *Blood* 87(5): 1928-1938. |
| Wahab, N. A., L. Schaefer, B. S. Weston, O. Yiannikouris, A. Wright, A. Babelova, R. Schaefer and R. M. Mason (2005). "Glomerular expression of thrombospondin-1, transforming growth factor beta and connective tissue growth factor at different stages of diabetic nephropathy and their interdependent roles in mesangial response to diabetic stimuli." *Diabetologia* 48(12): 2650-2660. |
| Wang, S., S. Shiva, M. H. Poczatek, V. Darley-Usmar and J. E. Murphy-Ullrich (2002). "Nitric oxide and cGMP-dependent protein kinase regulation of glucose-mediated thrombospondin 1-dependent transforming growth factor-beta activation in mesangial cells." *J Biol Chem* 277(12): 9880-9888. |
| Wang, S., J. Skorczewski, X. Feng, L. Mei and J. E. Murphy-Ullrich (2004). "Glucose up-regulates thrombospondin 1 gene transcription and transforming growth factor-beta activity through antagonism of cGMP-dependent protein kinase repression via upstream stimulatory factor 2." *J Biol Chem* 279(33): 34311-34322. |
| Xie, X. S., F. Y. Li, H. C. Liu, Y. Deng, Z. Li and J. M. Fan (2010). "LSKL, a peptide antagonist of thrombospondin-1, attenuates renal interstitial fibrosis in rats with unilateral ureteral obstruction." *Archives of pharmacal research* 33(2): 275-284. |
| Yang, K., J. L. Vega, M. Hadzipasic, J. P. Schatzmann Peron, B. Zhu, Y. Carrier, S. Masli, L. V. Rizzo and H. L. Weiner (2009). "Deficiency of thrombospondin-1 reduces Th17 differentiation and attenuates experimental autoimmune encephalomyelitis." *J Autoimmun*. |
| Yang, Y. L., L. Y. Chuang, J. Y. Guh, S. F. Liu, M. Y. Hung, T. N. Liao and Y. L. Huang (2004). "Thrombospondin-1 mediates distal tubule hypertrophy induced by glycated albumin." *The Biochemical journal* 379(Pt 1): 89-97. |
| Yee, K. O., M. Streit, T. Hawighorst, M. Detmar and J. Lawler (2004). "Expression of the type-1 repeats of thrombospondin-1 inhibits tumor growth through activation of transforming growth factor-beta." *Am J Pathol* 165(2): 541-552. |
| Yehualaeshet, T., R. O'Connor, A. Begleiter, J. E. Murphy-Ullrich, R. Silverstein and N. Khalil (2000). "A CD36 synthetic peptide inhibits bleomycin-induced pulmonary inflammation and connective tissue synthesis in the rat." *Am J Respir Cell Mol Biol* 23(2): 204-212. |
| Yehualaeshet, T., R. O'Connor, J. Green-Johnson, S. Mai, R. Silverstein, J. E. Murphy-Ullrich and N. Khalil (1999). "Activation of rat alveolar macrophage-derived latent transforming growth factor beta-1 by plasmin requires interaction with thrombospondin-1 and its cell surface receptor, CD36." *The American journal of pathology* 155(3): 841-851. |
| Yevdokimova, N., N. A. Wahab and R. M. Mason (2001). "Thrombospondin-1 is the key activator of TGF-beta1 in human mesangial cells exposed to high glucose." *J Am Soc Nephrol* 12(4): 703-712. |
| Young, G. D. and J. E. Murphy-Ullrich (2004). "Molecular interactions that confer latency to transforming growth factor-beta." *J Biol Chem* 279(36): 38032-38039. |
| Zamiri, P., S. Mash, N. Kitaichi, A. W. Taylor and J. W. Streilein (2005). "Thrombospondin plays a vital role in the immune privilege of the eye." *Invest Ophthalmol Vis Sci* 46(3): 908-919. |
| Zhou, Y., J. S. Hagood and J. E. Murphy-Ullrich (2004). "Thy-1 expression regulates the ability of rat lung fibroblasts to activate transforming growth factor-beta in response to fibrogenic stimuli." *The American journal of pathology* 165(2): 659-669. |
| Zhou, Y., M. H. Poczatek, K. H. Berecek and J. E. Murphy-Ullrich (2006). "Thrombospondin 1 mediates angiotensin II induction of TGF-beta activation by cardiac and renal cells under both high and low glucose conditions." *Biochem Biophys Res Commun* 339(2): 633-641. |

ILLUSTRATIVE EXAMPLES

A. General Synthesis

The illustrative example compounds were prepared analogous to solid phase peptide synthesis as outlined in Scheme 1 using either pre-formed (pre-activated) species or in situ activated (without pre-activation) amino acids. Commonly used activated esters are the pentafluorophenyl (OPfp) ester and the 3-hydroxy-2,3-dihydro-4-oxo-benzo-triazone (ODhbt) ester. (5-7). In the presence of hydroxybenzonitrile (HOBt) the rate of reaction was very rapid. In addition, coupling reactions were conducted in situ using activating reagents such as O-benzotriazole-N,N,N',N'-tetramethyl-uronium-hexafluoro-phosphate (HBTU), benzotriazol-1-yloxy)tris (dimethylamino)-phosphonium hexafluorophosphate (BOP), or BOP-Cl, or conducting the coupling reaction using carbodiimide, e.g., dicyclohexylcarbodiimide, as activator. The solid polymer was Rink resin.

B. Illustrative Compounds

The illustrative compounds listed in the following table were, or can be, prepared in an analogous manner.

| No. | $R^a$ | $R^1$ | $R^2$ | $R^3$ | $R^4$ | $R^5$ | $R^6$ | $R^7$ |
|---|---|---|---|---|---|---|---|---|
| 1 | $CH_3$ | $CH_2OH$ | $(CH_2)_4NH_2$ | $CH_2CH(CH_3)_2$ | H | H | H | H |
| 2 | $CH_3$ | $CH(CH_3)OH$ | $(CH_2)_4NH_2$ | $CH_2CH(CH_3)_2$ | H | H | H | H |
| 3 | $CH_3$ | $CH_2CH(CH_3)OH$ | $(CH_2)_4NH_2$ | $CH_2CH(CH_3)_2$ | H | H | H | H |
| 4 | $CH_3$ | $CH_2OH$ | $(CH_2)_4NH_2$ | $CH_2CH(CH_3)_2$ | $CH_3$ | H | H | H |
| 5 | $CH_3$ | $CH(CH_3)OH$ | $(CH_2)_4NH_2$ | $CH_2CH(CH_3)_2$ | $CH_3$ | H | H | H |
| 6 | $CH_3$ | $CH_2CH(CH_3)OH$ | $(CH_2)_4NH_2$ | $CH_2CH(CH_3)_2$ | $CH_3$ | H | H | H |
| 7 | $CH_3$ | $CH_2OH$ | $(CH_2)_4NH_2$ | $CH_2CH(CH_3)_2$ | $CH_2CH_3$ | H | H | H |
| 8 | $CH_3$ | $CH(CH_3)OH$ | $(CH_2)_4NH_2$ | $CH_2CH(CH_3)_2$ | $CH_2CH_3$ | H | H | H |
| 9 | $CH_3$ | $CH_2CH(CH_3)OH$ | $(CH_2)_4NH_2$ | $CH_2CH(CH_3)_2$ | $CH_2CH_3$ | H | H | H |
| 10 | $CH_3$ | $CH_2OH$ | $(CH_2)_4NH_2$ | $CH_2CH(CH_3)_2$ | H | $CH_3$ | H | H |
| 11 | $CH_3$ | $CH(CH_3)OH$ | $(CH_2)_4NH_2$ | $CH_2CH(CH_3)_2$ | H | $CH_3$ | H | H |
| 12 | $CH_3$ | $CH_2CH(CH_3)OH$ | $(CH_2)_4NH_2$ | $CH_2CH(CH_3)_2$ | H | CH | H | H |
| 13 | $CH_3$ | $CH_2OH$ | $(CH_2)_4NH_2$ | $CH_2CH(CH_3)_2$ | H | H | H | $CH_3$ |
| 14 | $CH_3$ | $CH(CH_3)OH$ | $(CH_2)_4NH_2$ | $CH_2CH(CH_3)_2$ | H | H | H | $CH_3$ |
| 15 | $CH_3$ | $CH_2CH(CH_3)OH$ | $(CH_2)_4NH_2$ | $CH_2CH(CH_3)_2$ | H | H | H | $CH_3$ |
| 16 | $CH_3$ | $CH(CH_3)OCH_3$ | $(CH_2)_4NH_2$ | $CH_2CH(CH_3)_2$ | H | H | H | H |
| 17 | $CH_3$ | CH(OH)-phenyl | $(CH_2)_4NH_2$ | $CH_2CH(CH_3)_2$ | H | H | H | H |
| 18 | $CH_3$ | 2-OH-c-propyl | $(CH_2)_4NH_2$ | $CH_2CH(CH_3)_2$ | H | H | H | H |
| 19 | c-propyl | $CH_2OH$ | $(CH_2)_4NH_2$ | $CH_2CH(CH_3)_2$ | H | H | H | H |
| 20 | c-propyl | $CH(CH_3)OH$ | $(CH_2)_4NH_2$ | $CH_2CH(CH_3)_2$ | H | H | H | H |
| 21 | c-propyl | $CH_2CH(CH_3)OH$ | $(CH_2)_4NH_2$ | $CH_2CH(CH_3)_2$ | H | H | H | H |
| 22 | $CH_3$ | $CH_2OH$ | $(CH_2)_4N(CH_3)_2$ | $CH_2CH(CH_3)_2$ | H | H | H | H |
| 23 | $CH_3$ | $CH(CH_3)OH$ | $(CH_2)_4N(CH_3)_2$ | $CH_2CH(CH_3)_2$ | H | H | H | H |
| 24 | $CH_3$ | $CH_2CH(CH_3)OH$ | $(CH_2)_4N(CH_3)_2$ | $CH_2CH(CH_3)_2$ | H | H | H | H |
| 25 | $CH_3$ | $CH(CH_3)OCH_3$ | $(CH_2)_4N(CH_3)_2$ | $CH_2CH(CH_3)_2$ | H | H | H | H |
| 26 | $CH_3$ | CH(OH)-phenyl | $(CH_2)_4N(CH_3)_2$ | $CH_2CH(CH_3)_2$ | H | H | H | H |
| 27 | $CH_3$ | 2-OH-c-propyl | $(CH_2)_4N(CH_3)_2$ | $CH_2CH(CH_3)_2$ | H | H | H | H |
| 28 | $CH_3$ | $CH_2OH$ | $(CH_2)_4NH_2$ | c-propyl | H | H | H | H |
| 29 | $CH_3$ | $CH(CH_3)OH$ | $(CH_2)_4NH_2$ | c-propyl | H | H | H | H |
| 30 | $CH_3$ | $CH_2CH(CH_3)OH$ | $(CH_2)_4NH_2$ | c-propyl | H | H | H | H |
| 31 | c-propyl | $CH_2OH$ | $(CH_2)_4NH_2$ | c-propyl | H | H | H | H |
| 32 | c-propyl | $CH(CH_3)OH$ | $(CH_2)_4NH_2$ | c-propyl | H | H | H | H |
| 33 | c-propyl | $CH_2CH(CH_3)OH$ | $(CH_2)_4NH_2$ | c-propyl | H | H | H | H |
| 34 | $CH_3$ | $CH_2OH$ | $(CH_2)_4N(CH_3)_2$ | c-propyl | H | H | H | H |
| 35 | $CH_3$ | $CH(CH_3)OH$ | $(CH_2)_4N(CH_3)_2$ | c-propyl | H | H | H | H |
| 36 | $CH_3$ | $CH_2CH(CH_3)OH$ | $(CH_2)_4N(CH_3)_2$ | c-propyl | H | H | H | H |
| 37 | $CH_3$ | $CH_2OH$ | $(CH_2)_4NH_2$ | $CH_2$-(c-propyl) | H | H | H | H |
| 38 | $CH_3$ | $CH(CH_3)OH$ | $(CH_2)_4NH_2$ | $CH_2$-(c-propyl) | H | H | H | H |
| 39 | $CH_3$ | $CH_2CH(CH_3)OH$ | $(CH_2)_4NH_2$ | $CH_2$-(c-propyl) | H | H | H | H |
| 40 | $CH_3$ | $CH_2OH$ | $(CH_2)_4N(CH_3)_2$ | $CH_2$-(c-propyl) | H | H | H | H |
| 41 | $CH_3$ | $CH(CH_3)OH$ | $(CH_2)_4N(CH_3)_2$ | $CH_2$-(c-propyl) | H | H | H | H |
| 42 | $CH_3$ | $CH_2CH(CH_3)OH$ | $(CH_2)_4N(CH_3)_2$ | $CH_2$-(c-propyl) | H | H | H | H |
| 43 | $CH_3$ | $CH_2OH$ | $(CH_2)_4NH_2$ | $CH_2$-(c-pentyl) | H | H | H | H |
| 44 | $CH_3$ | $CH(CH_3)OH$ | $(CH_2)_4NH_2$ | $CH_2$-(c-pentyl) | H | H | H | H |
| 45 | $CH_3$ | $CH_2CH(CH_3)OH$ | $(CH_2)_4NH_2$ | $CH_2$-(c-pentyl) | H | H | H | H |
| 46 | $CH_3$ | $CH_2OH$ | $(CH_2)_4N(CH_3)_2$ | $CH_2$-(c-pentyl) | H | H | H | H |
| 47 | $CH_3$ | $CH(CH_3)OH$ | $(CH_2)_4N(CH_3)_2$ | $CH_2$-(c-pentyl) | H | H | H | H |
| 48 | $CH_3$ | $CH_2CH(CH_3)OH$ | $(CH_2)_4N(CH_3)_2$ | $CH_2$-(c-pentyl) | H | H | H | H |
| 49 | $CH_3$ | $CH_2OH$ | $(CH_2)_4NH_2$ | $CH_2$-(phenyl) | H | H | H | H |
| 50 | $CH_3$ | $CH(CH_3)OH$ | $(CH_2)_4NH_2$ | $CH_2$-(phenyl) | H | H | H | H |
| 51 | $CH_3$ | $CH_2CH(CH_3)OH$ | $(CH_2)_4NH_2$ | $CH_2$-(phenyl) | H | H | H | H |
| 52 | $CH_3$ | $CH_2OH$ | $(CH_2)_4N(CH_3)_2$ | $CH_2$-(phenyl) | H | H | H | H |
| 53 | $CH_3$ | $CH(CH_3)OH$ | $(CH_2)_4N(CH_3)_2$ | $CH_2$-(phenyl) | H | H | H | H |
| 54 | $CH_3$ | $CH_2CH(CH_3)OH$ | $(CH_2)_4N(CH_3)_2$ | $CH_2$-(phenyl) | H | H | H | H |
| 55 | $CH_3$ | $CH_2OH$ | $(CH_2)_2$-[3-pyrrolidinyl] | $CH_2CH(CH_3)_2$ | H | H | H | H |
| 56 | $CH_3$ | $CH(CH_3)OH$ | $(CH_2)_2$-[3-pyrrolidinyl] | $CH_2CH(CH_3)_2$ | H | H | H | H |
| 57 | $CH_3$ | $CH_2CH(CH_3)OH$ | $(CH_2)_2$-[3-pyrrolidinyl] | $CH_2CH(CH_3)_2$ | H | H | H | H |
| 58 | $CH_3$ | $CH_2OH$ | $(CH_2)_2$-[3-pyrrolidinyl] | c-propyl | H | H | H | H |
| 59 | $CH_3$ | $CH(CH_3)OH$ | $(CH_2)_2$-[3-pyrrolidinyl] | c-propyl | H | H | H | H |
| 60 | $CH_3$ | $CH_2CH(CH_3)OH$ | $(CH_2)_2$-[3-pyrrolidinyl] | c-propyl | H | H | H | H |
| 61 | $CH_3$ | $CH_2OH$ | $(CH_2)_2$-[3-pyrrolidinyl] | $CH_2$-(c-propyl) | H | H | H | H |
| 62 | $CH_3$ | $CH(CH_3)OH$ | $(CH_2)_2$-[3-pyrrolidinyl] | $CH_2$-(c-propyl) | H | H | H | H |
| 63 | $CH_3$ | $CH_2CH(CH_3)OH$ | $(CH_2)_2$-[3-pyrrolidinyl] | $CH_2$-(c-propyl) | H | H | H | H |
| 64 | $CH_3$ | $CH_2OH$ | $(CH_2)_2$-[3-pyrrolidinyl] | $CH_2$-(c-pentyl) | H | H | H | H |
| 65 | $CH_3$ | $CH(CH_3)OH$ | $(CH_2)_2$-[3-pyrrolidinyl] | $CH_2$-(c-pentyl) | H | H | H | H |
| 66 | $CH_3$ | $CH_2CH(CH_3)OH$ | $(CH_2)_2$-[3-pyrrolidinyl] | $CH_2$-(c-pentyl) | H | H | H | H |
| 67 | $CH_3$ | $CH_2OH$ | $(CH_2)_2$-[3-pyrrolidinyl] | $CH_2$-(phenyl) | H | H | H | H |
| 68 | $CH_3$ | $CH(CH_3)OH$ | $(CH_2)_2$-[3-pyrrolidinyl] | $CH_2$-(phenyl) | H | H | H | H |
| 69 | $CH_3$ | $CH_2CH(CH_3)OH$ | $(CH_2)_2$-[3-pyrrolidinyl] | $CH_2$-(phenyl) | H | H | H | H |
| 70 | $CH_3$ | $CH_2OH$ | $(CH_2)_2$-[3-piperidinyl] | $CH_2CH(CH_3)_2$ | H | H | H | H |
| 71 | $CH_3$ | $CH(CH_3)OH$ | $(CH_2)_2$-[3-piperidinyl] | $CH_2CH(CH_3)_2$ | H | H | H | H |
| 72 | $CH_3$ | $CH_2CH(CH_3)OH$ | $(CH_2)_2$-[3-piperidinyl] | $CH_2CH(CH_3)_2$ | H | H | H | H |

-continued

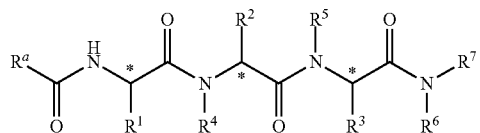

| No. | $R^a$ | $R^1$ | $R^2$ | $R^3$ | $R^4$ | $R^5$ | $R^6$ | $R^7$ |
|---|---|---|---|---|---|---|---|---|
| 73 | $CH_3$ | $CH_2OH$ | $(CH_2)_2$-[3-piperidinyl] | c-propyl | H | H | H | H |
| 74 | $CH_3$ | $CH(CH_3)OH$ | $(CH_2)_2$-[3-piperidinyl] | c-propyl | H | H | H | H |
| 75 | $CH_3$ | $CH_2CH(CH_3)OH$ | $(CH_2)_2$-[3-piperidinyl] | c-propyl | H | H | H | H |
| 76 | $CH_3$ | $CH_2OH$ | $(CH_2)_2$-[3-piperidinyl] | $CH_2$-(c-propyl) | H | H | H | H |
| 77 | $CH_3$ | $CH(CH_3)OH$ | $(CH_2)_2$-[3-piperidinyl] | $CH_2$-(c-propyl) | H | H | H | H |
| 78 | $CH_3$ | $CH_2CH(CH_3OH)$ | $(CH_2)_2$-[3-piperidinyl] | $CH_2$-(c-propyl) | H | H | H | H |
| 79 | $CH_3$ | $CH_2OH$ | $(CH_2)_2$-[3-piperidinyl] | $CH_2$-(c-pentyl) | H | H | H | H |
| 80 | $CH_3$ | $CH(CH_3)OH$ | $(CH_2)_2$-[3-piperidinyl] | $CH_2$-(c-pentyl) | H | H | H | H |
| 81 | $CH_3$ | $CH_2CH(CH_3OH)$ | $(CH_2)_2$-[3-piperidinyl] | $CH_2$-(c-pentyl) | H | H | H | H |
| 82 | $CH_3$ | $CH_2OH$ | $(CH_2)_2$-[3-piperidinyl] | $CH_2$-(phenyl) | H | H | H | H |
| 83 | $CH_3$ | $CH(CH_3)OH$ | $(CH_2)_2$-[3-piperidinyl] | $CH_2$-(phenyl) | H | H | H | H |
| 84 | $CH_3$ | $CH_2CH(CH_3)OH$ | $(CH_2)_2$-[3-piperidinyl] | $CH_2$-(phenyl) | H | H | H | H |
| 85 | $CH_3$ | $CH_2OH$ | $(CH_2)_3$—$CH(CH_3)$—$NH_2$ | $CH_2CH(CH_3)_2$ | H | H | H | H |
| 86 | $CH_3$ | $CH(CH_3)OH$ | $(CH_2)_3$—$CH(CH_3)$—$NH_2$ | $CH_2CH(CH_3)_2$ | H | H | H | H |
| 87 | $CH_3$ | $CH_2CH(CH_3)OH$ | $(CH_2)_3$—$CH(CH_3)$—$NH_2$ | $CH_2CH(CH_3)_2$ | H | H | H | H |
| 88 | $CH_3$ | $CH_2OH$ | $(CH_2)_2$—$CH(OH)$—$CH_2NH_2$ | $CH_2CH(CH_3)_2$ | H | H | H | H |
| 89 | $CH_3$ | $CH_2OH$ | $(CH_2)_2$—$CH(OH)$—$CH_2NH_2$ | $CH_2CH(CH_3)_2$ | H | H | H | H |
| 90 | $CH_3$ | $CH_2CH(CH_3)OH$ | $(CH_2)_2$—$CH(OH)$—$CH_2NH_2$ | $CH_2CH(CH_3)_2$ | H | H | H | H |
| 91 | $CH_3$ | $CH_2OH$ | $(CH_2)_2$—$C(CH_3)_2$—$CH_2NH_2$ | $CH_2CH(CH_3)_2$ | H | H | H | H |
| 92 | $CH_3$ | $CH(CH_3)OH$ | $(CH_2)_2$—$C(CH_3)_2$—$CH_2NH_2$ | $CH_2CH(CH_3)_2$ | H | H | H | H |
| 93 | $CH_3$ | $CH_2CH(CH_3)OH$ | $(CH_2)_2$—$C(CH_3)_2$—$CH_2NH_2$ | $CH_2CH(CH_3)_2$ | H | H | H | H |
| 94 | $CH_3$ | $CH_2OH$ | $(CH_2)_4NH_2$ | $CH_2CH(CH_3)_2$ | H | H | H | H |
| 95 | $CH_3$ | $CH_2OH$ | $(CH_2)_4NH_2$ | $CH_2CH(CH_3)_2$ | H | H | H | H |
| 96 | $CH_3$ | $CH_2OH$ | $(CH_2)_4NH_2$ | $CH_2CH(CH_3)_2$ | H | H | H | H |
| 97 | $CH_3$ | $CH_2OH$ | $(CH_2)_4NH_2$ | $CH_2CH(CH_3)_2$ | H | H | $CH_3$ | $CH_3$ |
| 98 | $CH_3$ | $CH_2OH$ | $(CH_2)_4N(CH_3)$ H | $CH_2CH(CH_3)_2$ | H | H | H | H |
| 99 | $CH_3$ | $CH_2OH$ | $(CH_2)_4N(COCH_3)$ H | $CH_2CH(CH_3)_2$ | H | H | H | H |
| 100 | $CH_3$ | $CH_2OCH_3$ | $(CH_2)_4NH_2$ | $CH_2CH(CH_3)_2$ | H | H | H | H |
| 101 | $C_2H_5$ | $CH_2OH$ | $(CH_2)_4NH_2$ | $CH_2CH(CH_3)_2$ | H | H | H | H | c-propyl = cyclopropyl; c-pentyl = cyclophentyl

The following non-limiting examples of compound structures are presented to further facilitate an understanding of the present disclosure.

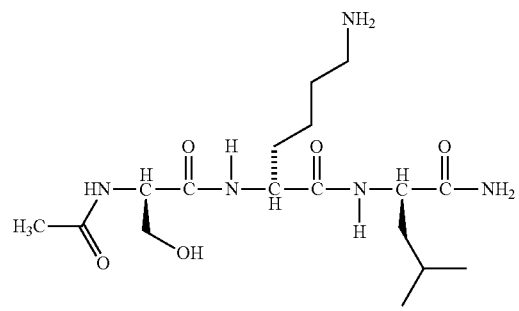

1

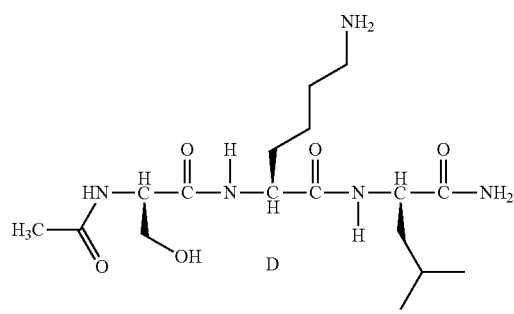

95

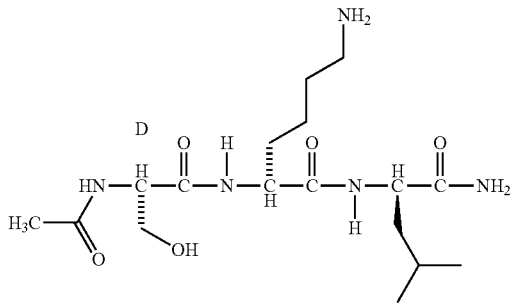

94

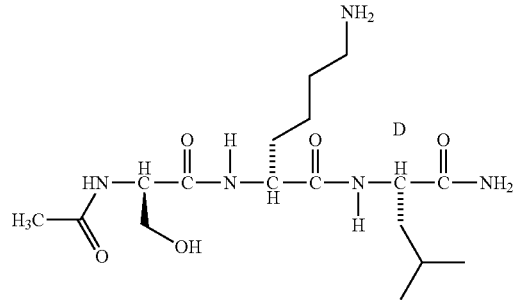

96

13
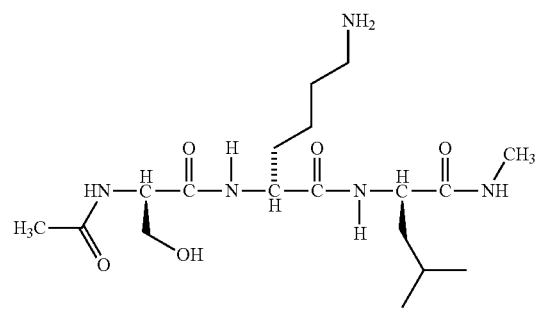
97
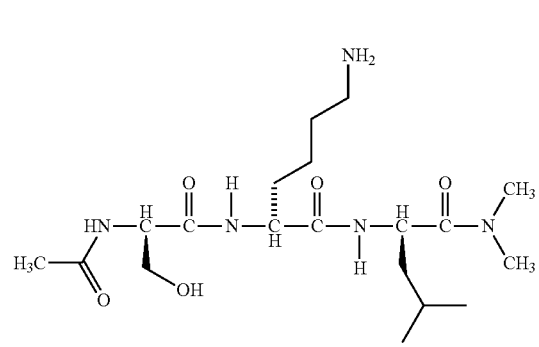
22
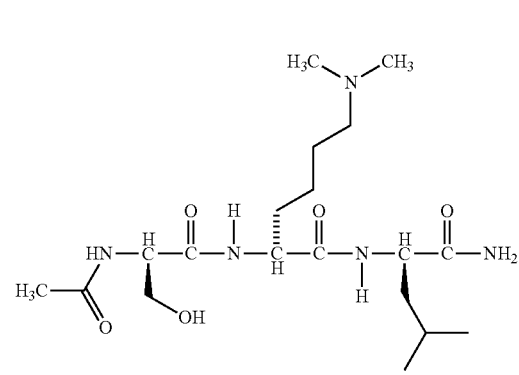
98
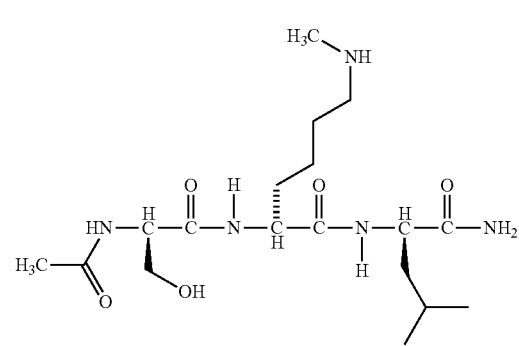
99
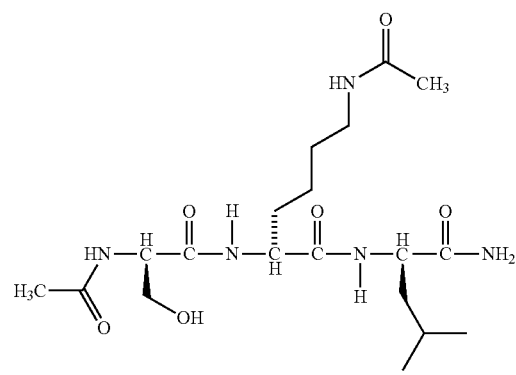
10
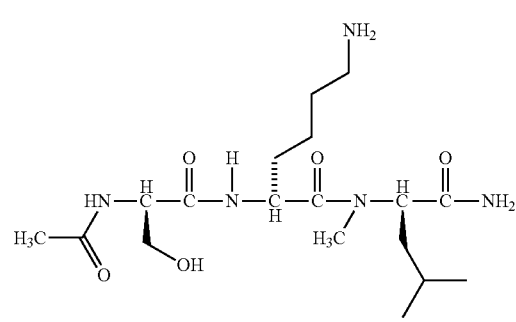
2
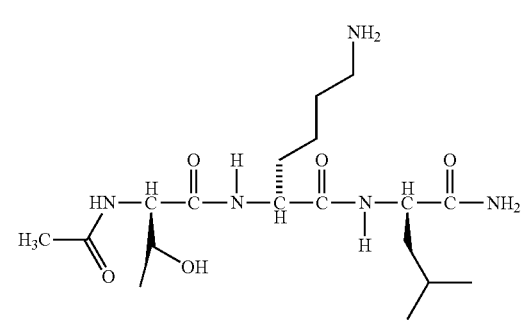
100
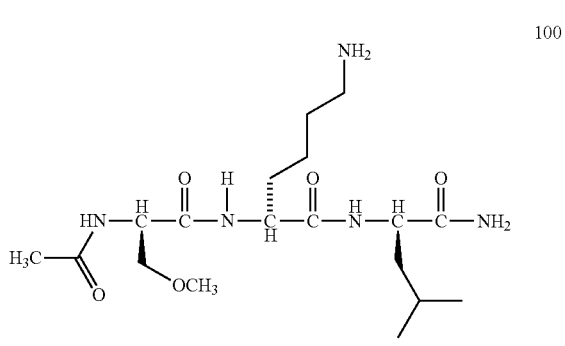

-continued

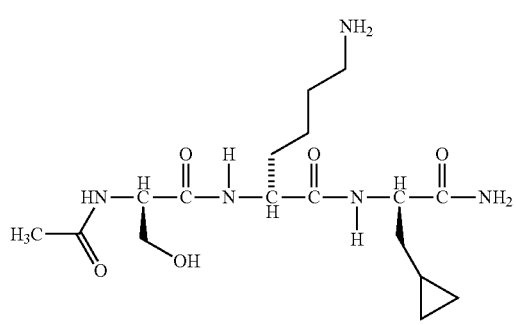

37

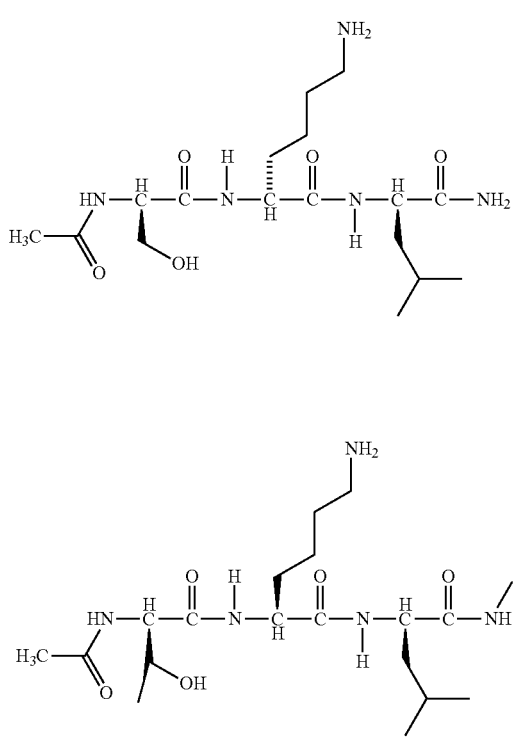

101

14

The Table 1 below shows activity for some selected compounds according to the present invention. The assay for the IC 50 (Activity) data in Table 1 was as follows: Recombinant latent TGF-beta (500 pM) is incubated with TSP1 (48 nM) in the absence or presence of increasing concentrations of the identified compounds (1-100 pM). TGF-beta activity in the samples was measured using an ELISA specific for active TGF-beta (R&D Systems). IC50 values were calculated from the curves.

TABLE 1

| No. | Mol. Formula | Mol. Weight | Mass Spec. | Purity % | Activity |
|---|---|---|---|---|---|
| 96 | $C_{17}H_{33}N_5O_5$ | 387.48 | 387.88 | 95.47 | ++ |
| 13 | $C_{18}H_{35}N_5O_5$ | 401.53 | 401.91 | 96.86 | ++ |
| 95 | $C_{17}H_{33}N_5O_5$ | 387.48 | 388.04 | 96.49 | +++ |
| 14 | $C_{19}H_{37}N_5O_5$ | 415.53 | 416.12 | 98.83 | +++ |
| 94 | $C_{17}H_{33}N_5O_5$ | 387.48 | 387.99 | 99.15 | + |
| 1 | $C_{17}H_{33}N_5O_5$ | 387.48 | 387.86 | 96.01 | +++ |
| 97 | $C_{19}H_{37}N_5O_5$ | 415.55 | 415.97 | 95.57 | + |
| 101 | $C_{18}H_{35}N_5O_5$ | 401.51 | 401.85 | 95.14 | + |
| 98 | $C_{18}H_{35}N_5O_5$ | 401.48 | 401.91 | 95.69 | + |
| 22 | $C_{19}H_{37}N_5O_5$ | 415.48 | 415.91 | 96.77 | + |
| 99 | $C_{19}H_{36}N_5O_6$ | 430.53 | 429.21 | 96.97 | + |
| 10 | $C_{18}H_{35}N_5O_5$ | 401.48 | 401.85 | 95.25 | + |
| 2 | $C_{18}H_{35}N_5O_5$ | 401.51 | 401.91 | 95.95 | ++ |
| 37 | $C_{17}H_{31}N_5O_5$ | 385.47 | 386.41 | 99.58 | ++ |
| 100 | $C_{18}H_{35}N_5O_5$ | 401.48 | 401.91 | 96.05 | + |

+ 100-500 pM,
++ 50-100 pM,
+++ 1-10 pM

The Table 2 below provides an analysis of the systemic SCID-CAG-heparanase model treated with increasing doses of Compound No 1 according to the present invention.

TABLE 2

| Compound No 1 | Saline | 0.3 mg/kg/day | 3.0 mg/kg/day | 30 mg/kg/day |
|---|---|---|---|---|
| Human serum κ (ng/ml) | 5931 +/− 889 | 5134 +/− 696 | 3465 +/− 422* | 2593 +/− 443* |
| Serum TRAcP 5b (U/L) | 4.26 +/− 0.19 | 3.6 +/− 0.28 | 2.8 +/− 0.15* | 2.5 +/− 0.13* |
| IL-6 (pg/ml) | 93.3 +/− 12.9 | 70.2 +/− 4.7 | 40.0 +/− 4.2* | 31.8 +/− 4.0* |
| μCT (tibia) (n = 4) | | | | |
| BV/TV | 0.05 + 0.01 | | | 0.13 +/− 0.01* |
| TbN | 2.55 +/− 0.3 | | | 4.03 +/− 0.28* |
| TbSp | 0.41 +/− 0.05 | | | 0.25 +/− 0.02* |
| TRAP+ OC/mm BS | 4.0 +/− 0.3 | | | 1.0 +/− 0.2* |
| p-Smad 2 IHC in bone marrow | 10,701 +/− 4101 (arbitrary units) | | | 2390 +/− 472* |

Table 2: Analyses of the Systemic SCID-CAG-Heparanase Model Treated with Increasing Doses of Compound No 1

Male SCID mice were injected via tail vein with $1.7 \times 10^6$ CAG-hpse cells and tumors allowed to establish over 2 weeks. Groups were randomized according to serum human kappa levels (n=15/group). Treatments were initiated at 2 weeks and continued for 4 weeks. Mice were treated with either saline or 0.3, 3.0, or 30 mg/kg/day of Compound No 1 peptide delivered by osmotic pumps. Pumps were replaced after 2 weeks and fresh peptide and pumps installed. *p<0.05 vs saline.

The Table 3 below demonstrates pharmacokinetic parameters of compound 1 in plasma following a single intravenous (dose: 1 mg/kg) and oral (dose: 3 mg/kg administration in male Swiss Albino mice.

TABLE 3

Pharmacokinetic parameters of compound 1 in plasma following a single intravenous (Dose: 1 mg/kg) and oral (Dose: 3 mg/kg) administration in male Swiss Albino mice

| Route | Matrix | $T_{max}$ (hr) | $^aC_o/C_{max}$ (ng/mL) | $AUC_{last}$ (hr * ng/mL) | $AUC_{inf}$ (hr * ng/mL) | $T_{1/2}$ (hr) | CL (mL/min/kg) | $V_{ss}$ (L/kg) | % $F^b$ |
|---|---|---|---|---|---|---|---|---|---|
| i.v. | Plasma | — | 1025.73 | 1214.83 | 1375.35 | 10.62 | 12.12 | 6.31 | 24 |
| p.o. | Plasma | 0.50 | 208.24 | 875.12 | 1067.46 | — | — | — | |

What is claimed is:

1. A compound of formula (I)

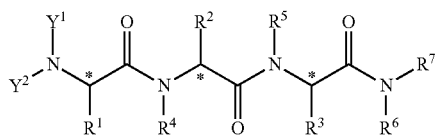

wherein * designates a chiral center of R or S configuration when the carbon atom so marked carries at most one hydrogen substituent, $Y^1$, $R^5$, and $R^6$, are identical or different and are hydrogen, $C_1$-$C_4$-alkyl which is optionally substituted by $C_3$-$C_6$-cycloalkyl or aryl, or are $C_3$-$C_6$-cycloalkyl;

$R^4$ is hydrogen or $C_1$-$C_4$-alkyl which is optionally substituted by $C_3$-$C_6$-cycloalkyl or aryl;

$Y^2$ is hydrogen, $C_1$-$C_4$-alkyl which is optionally substituted by $C_3$-$C_6$-cycloalkyl or aryl, or is $C_3$-$C_6$-cycloalkyl or $COR^a$;

$R^a$ is hydrogen, $C_1$-$C_4$-alkyl, $C_3$-$C_6$-cycloalkyl, or optionally substituted aryl;

$R^1$ is hydrogen, $C_1$-$C_6$-alkyl, $C_1$-$C_4$-alkyl which is substituted by hydroxyl or $OR^b$, or is optionally substituted $C_3$-$C_6$-cycloalkyl or optionally substituted 5- or 6-membered heterocyclyl;

$R^b$ is $C_1$-$C_6$-alkyl, $C_3$-$C_6$-cycloalkyl, or optionally substituted 5- or 6-membered heterocyclyl;

$R^2$ is $C_1$-$C_8$-alkyl which is substituted by $NR^cR^d$;

$R^c$ is hydrogen or $C_1$-$C_4$-alkyl; and $R^d$ is hydrogen, $C_1$-$C_4$-alkyl, $C_3$-$C_6$-cycloalkyl or C(=O) $C_1$-$C_4$-alkyl; or $R^c$ and $R^d$ together with the nitrogen to which they are bonded form an optionally substituted 5- or 6-membered heterocycle;

$R^3$ is optionally substituted $C_1$-$C_6$-alkyl, or optionally substituted $C_3$-$C_6$-cycloalkyl; and $R^7$ is hydrogen, $C_1$-$C_6$-alkyl, $C_1$-$C_4$-alkyl which is substituted by $C_3$-$C_6$-cycloalkyl or aryl, or is optionally substituted $C_3$-$C_6$-cycloalkyl;

or a derivative thereof selected from the group consisting of pharmaceutically acceptable salts, prodrugs, deuterated forms, radio-actively labeled forms, stereo isomers, solvates and combinations thereof.

2. The compound according to claim 1 which is represented by formula (II)

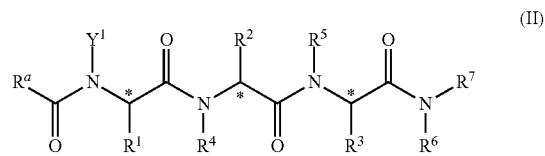

wherein $R^a$ is $C_1$-$C_4$-alkyl, $C_3$-$C_6$-cycloalkyl, or optionally substituted aryl;

or a derivative thereof selected from the group consisting of pharmaceutically acceptable salts, prodrugs, deuterated forms, radio-actively labeled forms, stereo isomers, solvates and combinations thereof.

3. The compound according to claim 1 which is represented by formula (III)

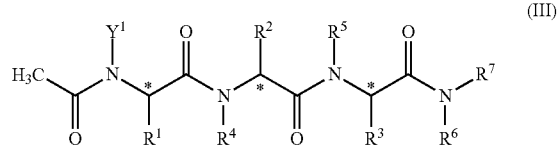

wherein $R^2$ is $C_1$-$C_6$-alkyl which is substituted by $NR^cR^d$;

$R^c$ is hydrogen; and $R^d$ is hydrogen, $C_1$-$C_4$-alkyl, or $C_3$-$C_6$-cycloalkyl; or $R^c$ and $R^d$ together with the nitrogen to which they are bonded form an optionally substituted 5- or 6-membered heterocycle;

or a derivative thereof selected from the group consisting of pharmaceutically acceptable salts, prodrugs, deuterated forms, radio-actively labeled forms, stereo isomers, solvates and combinations thereof.

4. The compound or derivative according to claim 3, wherein $R^1$ is $C_1$-$C_4$-alkyl which is substituted by hydroxyl.

5. The compound or derivative according to claim 3, wherein $R^3$ is $C_1$-$C_6$-alkyl which is optionally substituted by $C_3$-$C_6$-cycloalkyl or aryl, or is $C_3$-$C_6$-cycloalkyl.

6. The compound according to claim 1 being selected from the group consisting of

1

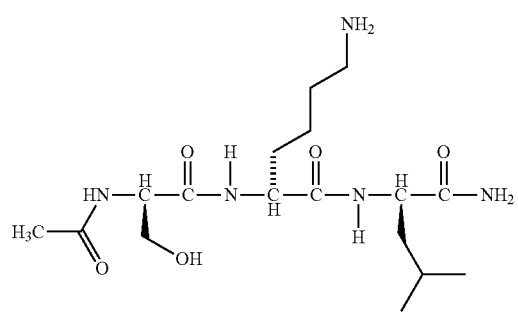

2

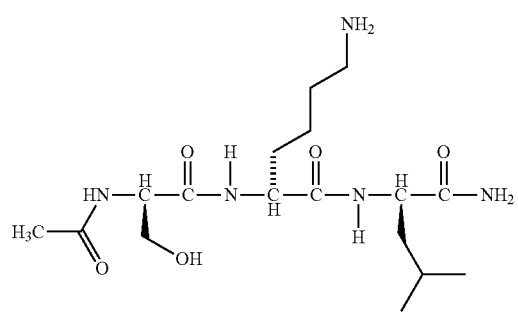

13

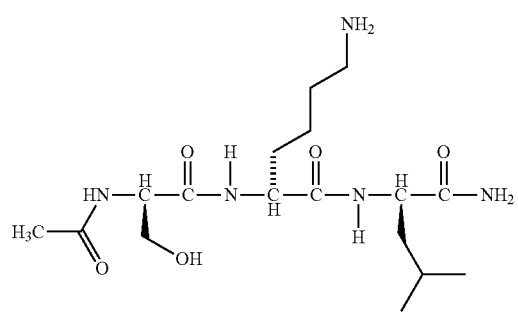

14

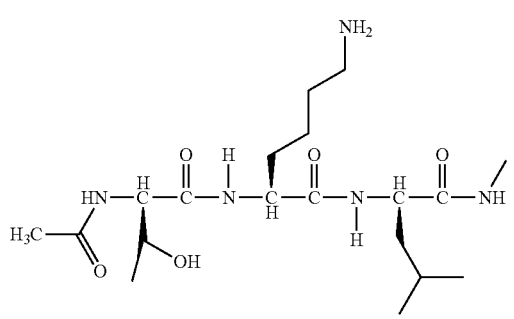

37

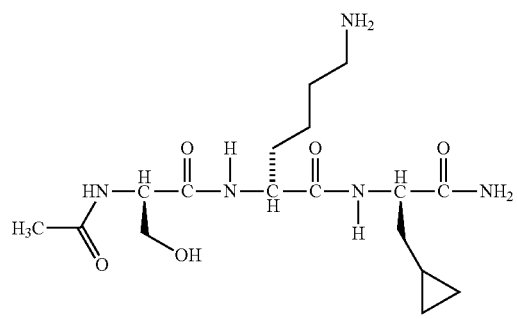

95

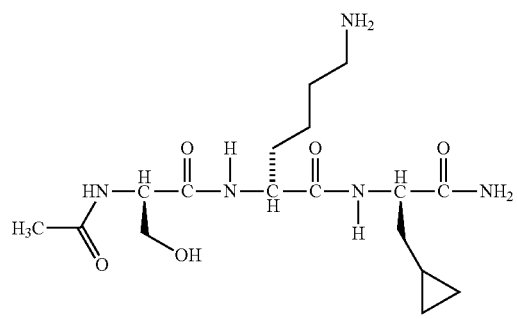

and

96

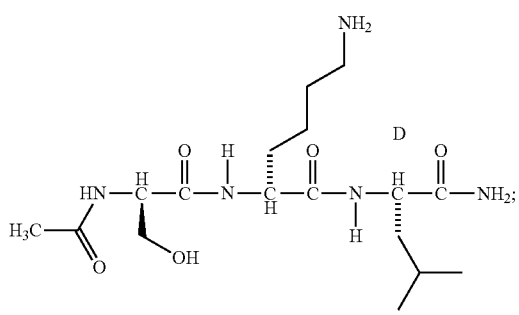

or a derivative thereof selected from the group consisting of pharmaceutically acceptable salts, prodrugs, deuterated forms, radio-actively labeled forms, stereo isomers, solvates and combinations thereof.

7. A pharmaceutical composition comprising a compound or derivative according to claim 1 and a pharmaceutically acceptable carrier.

8. The compound according to claim 1, wherein $Y^1$, $R^4$, $R^5$, and $R^6$ are identical or different and are hydrogen or $C_1$-$C_4$-alkyl.

9. The compound according to claim 1, wherein $Y^1$, $R^4$, $R^5$, and $R^6$ are hydrogen.

10. The compound according to claim 1, wherein $Y^2$ is $COR^a$, and $R^a$ is $C_1$-$C_4$-alkyl.

11. The compound according to claim 1, wherein $R^3$ is unsubstituted $C_1$-$C_6$-alkyl, or is $C_3$-$C_6$-cycloalkyl.

12. The compound according to claim 1, wherein $R^7$ is hydrogen or $C_1$-$C_4$-alkyl.

13. A compound of formula (I)

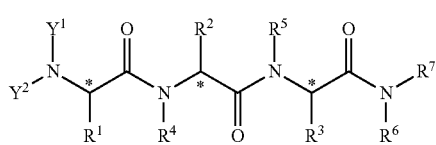

wherein * designates a chiral center of R or S configuration when the carbon atom so marked carries at most one hydrogen substituent, $Y^1$, $R^4$, $R^5$, and $R^6$, are identical or different and are hydrogen, $C_1$-$C_4$-alkyl which is optionally substituted by $C_3$-$C_6$-cycloalkyl or aryl, or are $C_3$-$C_6$-cycloalkyl;

$Y^2$ is hydrogen, $C_1$-$C_4$-alkyl which is optionally substituted by $C_3$-$C_6$-cycloalkyl or aryl, or is $C_3$-$C_6$-cycloalkyl or $COR^a$;

$R^a$ is hydrogen, $C_1$-$C_4$-alkyl, $C_3$-$C_6$-cycloalkyl, or optionally substituted aryl;

$R^1$ is $C_1$-$C_4$-alkyl which is substituted by hydroxyl;

$R^2$ is $C_1$-$C_8$-alkyl which is substituted by $NR^cR^d$;

$R^c$ is hydrogen or $C_1$-$C_4$-alkyl; and $R^d$ is hydrogen, $C_1$-$C_4$-alkyl, $C_3$-$C_6$-cycloalkyl or $C(=O)$ $C_1$-$C_4$-alkyl; or $R^c$ and $R^d$ together with the nitrogen to which they are bonded form an optionally substituted 5- or 6-membered heterocycle;

$R^3$ is optionally substituted $C_1$-$C_6$-alkyl, or optionally substituted $C_3$-$C_6$-cycloalkyl; and $R^7$ is hydrogen, $C_1$-$C_6$-alkyl, $C_1$-$C_4$-alkyl which is substituted by $C_3$-$C_6$-cycloalkyl or aryl, or is optionally substituted $C_3$-$C_6$-cycloalkyl;

or a derivative thereof selected from the group consisting of pharmaceutically acceptable salts, prodrugs, deuterated forms, radio-actively labeled forms, stereo isomers, solvates and combinations thereof.

14. The compound according to claim 13, wherein $Y^1$, $R^4$, $R^5$, and $R^6$, are identical or different and are hydrogen or $C_1$-$C_4$-alkyl.

15. A pharmaceutical composition comprising a compound or derivative according to claim 13 and a pharmaceutically acceptable carrier.

16. The compound of claim 1, wherein $R^2$ is —$(CH_2)_4NH_2$].

17. The compound of claim 1, wherein $R^1$ is $C_1$-$C_4$-alkyl substituted by hydroxyl or $OR^b$.

18. The compound of claim 1, wherein at least one of $R^6$ and $R^7$ is hydrogen and the other of $R^6$ and $R^7$ is hydrogen or $C_1$-$C_4$-alkyl.

* * * * *